United States Patent
Gebeyehu et al.

(10) Patent No.: US 10,538,784 B2
(45) Date of Patent: Jan. 21, 2020

(54) PLANT VIRUS MOVEMENT PROTEINS AND METHODS OF USING THE SAME

(71) Applicant: MOLECULAR TRANSFER, INC., Gaithersburg, MD (US)

(72) Inventors: Gulilat Gebeyehu, Gaithersburg, MD (US); Joel Jessee, Mount Airy, MD (US)

(73) Assignee: MOLECULAR TRANSFER, INC., Gaithersburg, MD (US)

( * ) Notice: Subject to any disclaimer, the term of this patent is extended or adjusted under 35 U.S.C. 154(b) by 0 days.

(21) Appl. No.: 15/446,578

(22) Filed: Mar. 1, 2017

(65) Prior Publication Data

US 2017/0253888 A1 Sep. 7, 2017

Related U.S. Application Data

(60) Provisional application No. 62/303,278, filed on Mar. 3, 2016, provisional application No. 62/302,155, filed on Mar. 1, 2016.

(51) Int. Cl.

| | | |
|---|---|---|
| *C12N 15/85* | (2006.01) | |
| *A61K 48/00* | (2006.01) | |
| *C12N 9/22* | (2006.01) | |
| *C12N 15/11* | (2006.01) | |
| *C12N 15/88* | (2006.01) | |
| *C12N 15/90* | (2006.01) | |

(52) U.S. Cl.
CPC .......... *C12N 15/85* (2013.01); *A61K 48/0041* (2013.01); *C12N 9/22* (2013.01); *C12N 15/11* (2013.01); *C12N 15/88* (2013.01); *C12N 15/907* (2013.01); *C12N 2310/20* (2017.05); *C12N 2810/10* (2013.01); *C12N 2810/65* (2013.01)

(58) Field of Classification Search
CPC .......... A61K 2039/53; A61K 39/39558; A61K 31/713; C07K 16/18; C12N 15/67
See application file for complete search history.

(56) References Cited

U.S. PATENT DOCUMENTS

| | | |
|---|---|---|
| 5,316,948 A | 5/1994 | Pless |
| 5,334,761 A | 8/1994 | Gebeyehu et al. |
| 5,578,475 A | 11/1996 | Jessee |
| 5,627,159 A | 5/1997 | Shih et al. |
| 5,674,908 A | 10/1997 | Haces et al. |
| 5,736,392 A * | 4/1998 | Hawley-Nelson ... A61K 9/1272 435/320.1 |
| 5,834,439 A | 11/1998 | Haces et al. |
| 5,994,109 A | 11/1999 | Woo et al. |
| 6,020,202 A | 2/2000 | Jessee |
| 6,033,884 A | 3/2000 | Woo et al. |
| 6,051,429 A | 4/2000 | Hawley-Nelson et al. |
| 6,075,012 A | 6/2000 | Gebeyehu et al. |
| 6,083,741 A | 7/2000 | Hart et al. |
| 6,110,916 A | 8/2000 | Haces et al. |
| 6,150,168 A | 11/2000 | Woo et al. |
| 6,177,554 B1 | 1/2001 | Woo et al. |
| 6,376,248 B1 | 4/2002 | Hawley-Nelson et al. |
| 6,399,663 B1 | 6/2002 | Haces et al. |
| 6,458,026 B1 | 10/2002 | Hart |
| 6,716,882 B2 | 4/2004 | Haces et al. |
| 7,145,039 B2 | 12/2006 | Chu et al. |
| 7,166,745 B1 | 1/2007 | Chu et al. |
| 7,256,043 B2 | 8/2007 | Hart et al. |
| 7,531,693 B2 | 5/2009 | Gebeyehu et al. |
| 7,598,421 B2 | 10/2009 | Hailes et al. |
| 7,704,969 B2 | 4/2010 | Hart et al. |
| 7,820,624 B2 | 10/2010 | Hart et al. |
| 7,915,230 B2 | 3/2011 | Jessee et al. |
| 8,026,341 B2 | 9/2011 | Hart et al. |
| 8,034,977 B2 | 10/2011 | Gebeyehu et al. |
| 8,785,200 B2 * | 7/2014 | Chu ................... A61K 31/14 435/458 |
| 9,259,475 B2 * | 2/2016 | Jessee .................. A61K 31/195 |
| 9,358,300 B2 * | 6/2016 | Chu ...................... A61K 31/14 |
| 9,765,359 B2 * | 9/2017 | Jessee .................. A61K 31/195 |
| 10,155,780 B2 * | 12/2018 | Gebeyehu ............. C12N 15/88 |
| 2002/0138497 A1 | 9/2002 | Chen et al. |

(Continued)

FOREIGN PATENT DOCUMENTS

| | | |
|---|---|---|
| WO | 0027795 A1 | 5/2000 |
| WO | 03064625 A2 | 8/2003 |

(Continued)

OTHER PUBLICATIONS

Durkin et al. Amino acid sequence and domain structure of entactin. Homology with epidermal growth factor precursor and low density lipoprotein receptor. J Cell Biol. Dec. 1988;107(6 Pt 2):2749-2756. (Year: 1988).*

(Continued)

*Primary Examiner* — Marcela M Cordero Garcia
*Assistant Examiner* — Jai-Hai Lee
(74) *Attorney, Agent, or Firm* — Edell, Shapiro & Finnan LLC

(57) ABSTRACT

Disclosed herein are transfection complexes comprising at least one cell surface ligand; at least one helper lipid component; and a transfection enhancer. Also disclosed are pharmaceutical compositions comprising the disclosed transfection complexes, and a pharmaceutically acceptable carrier. Further, disclosed are methods of transfecting a cell, the method comprising the steps of: obtaining a transfection complex as disclosed; and contacting a cell with the transfection complex.

5 Claims, No Drawings
Specification includes a Sequence Listing.

(56) References Cited

U.S. PATENT DOCUMENTS

| | | | |
|---|---|---|---|
| 2004/0014956 A1 | 1/2004 | Woolf et al. | |
| 2004/0054155 A1 | 3/2004 | Woolf et al. | |
| 2005/0177900 A1 | 8/2005 | Nishiguchi et al. | |
| 2006/0009409 A1 | 1/2006 | Woolf | |
| 2009/0023216 A1 | 1/2009 | Woolf | |
| 2010/0136695 A1 | 6/2010 | Woolf | |
| 2014/0213637 A1* | 7/2014 | Jessee | A61K 31/195 514/44 R |

FOREIGN PATENT DOCUMENTS

| | | | |
|---|---|---|---|
| WO | 03064626 A2 | 8/2003 | |
| WO | 2004063342 A2 | 7/2004 | |
| WO | 2004105697 A2 | 12/2004 | |
| WO | 2007130073 A2 | 11/2007 | |
| WO | 2009039173 A2 | 3/2009 | |
| WO | 2012013326 A2 | 2/2012 | |
| WO | 2012142622 A1 | 10/2012 | |
| WO | 2013113326 A1 | 8/2013 | |
| WO | 2013158127 A1 | 10/2013 | |
| WO | WO2014070687 A2 * | 5/2014 | ............ A61K 48/00 |
| WO | 2017040335 A2 | 3/2017 | |

OTHER PUBLICATIONS

Chen et al. Fusion protein linkers: Property, design and functionality. Advanced Drug Delivery Reviews 65 (2013) 1357-1369. (Year: 2013).*

International Search Report and Written Opinion issued in PCT/US2017/020145 dated Jul. 19, 2017.

Search Report in corresponding European Application No. 17760696.9, dated Oct. 19, 2019.

Chakravartis, S., et al., "The Basement Membrane Glycoprotein Entactin Promotes Cell Attachment and Binds Calcium Ions" The Journal of Biological Chemistry vol. 265(18), pp. 10597-10603 (Jun. 2019).

Lee, K., et al., "Peptide-enhanced mRNA Transfection in Cultured Mouse Cardiac Fibroblasts and Direct Reprogramming Towards Cardiomyocyte-Like Cells", Int J Nanomedicine, vol. 10, pp. 1841-54 (Mar. 2015).

* cited by examiner

SEQUENCE LISTING

<160> NUMBER OF SEQ ID NOS: 585

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Tyr Ser Thr Pro Pro Lys Lys Arg Lys Val Glu Asp Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Ser Thr Pro Pro Lys Thr Arg Arg Arg Pro
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Ser Thr Pro Gly Arg Lys Lys Arg
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Ser Thr Pro Arg Arg Asn Arg Arg Arg Trp
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Asp Glu Val Lys Arg Lys Lys Lys Pro Pro Thr Ser Tyr Gly
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Pro Arg Arg Arg Thr Lys Pro Pro Thr Ser Tyr Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Lys Lys Arg Gly Pro Thr Ser Tyr Gly
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Arg Arg Arg Arg Asn Arg Arg Pro Thr Ser Tyr Gly
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Gly Pro Pro Lys Lys Lys Arg Lys Val Glu Ala Pro Tyr Lys
1               5                   10                  15

Ala

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Ala Ala Lys Arg Val Lys Leu Asp
1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Gln Arg Arg Asn Glu Leu Lys Arg Ser Pro
1               5                   10

```
<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Arg Lys Lys Arg Lys Thr Glu Glu Glu Ser Pro Leu Lys Asp Lys
1               5                   10                  15

Asp Ala Lys Lys Ser Lys Gln Glu
            20

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Leu Arg Arg Asp Ala Gly Gly Arg Gly Gly Val Tyr Glu His Leu
1               5                   10                  15

Gly Gly Ala Pro Arg Arg Arg Lys
            20

<210> SEQ ID NO 15
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Arg Lys Gly Asp Glu Val Asp Gly Val Asp Glu Cys Ala Lys Lys
1               5                   10                  15

Ser Lys Lys

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
```

```
                20                  25                  30

Arg Asn Gln Gly Gly Tyr
        35

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Lys Arg Thr Ala Asp Gly Ser Glu Phe Glu Ser Pro Lys Lys
1               5                   10                  15

Ala Arg Lys Val Glu Ala Tyr Pro Lys Ala Trp
            20                  25

<210> SEQ ID NO 18
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Lys Arg Thr Ala Asp Gly Ser Glu Phe Glu Ser Pro Lys Lys
1               5                   10                  15

Lys Arg Ala Val Glu Ala Tyr Pro Lys Ala Trp
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Lys Arg Thr Ala Asp Gly Ser Glu Phe Glu Ser Pro Lys Lys
1               5                   10                  15

Lys Ala Lys Val Glu Ala Tyr Pro Lys Ala Trp
            20                  25

<210> SEQ ID NO 20
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Lys Arg Thr Ala Asp Gly Ser Glu Phe Glu Ser Pro Lys Lys
1               5                   10                  15

Lys Arg Lys Val Glu Ala Pro Tyr Lys Ala Trp Lys
            20                  25

<210> SEQ ID NO 21
<211> LENGTH: 26
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 21

Gly Gly Lys Arg Thr Ala Asp Gly Ser Glu Phe Glu Ser Pro Lys Lys
1               5                   10                  15

Lys Arg Lys Val Glu Tyr Lys Ala Trp Lys
            20                  25

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Tyr Gly Pro Ala Ala Lys Arg Val Lys Leu Asp Glu Ala Tyr Pro
1               5                   10                  15

Lys Ala Trp Lys
            20

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Lys Arg Thr Ala Asp Gly Ser Glu Phe Glu Pro Ala Ala Lys
1               5                   10                  15

Arg Val Lys Leu Asp Glu Ala Tyr Pro Lys Ala Trp Lys
            20                  25

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Thr Gly Pro Lys Lys Lys Arg Lys Val Gly Gly Gly Gly Tyr Gly
1               5                   10                  15

Pro Lys Lys Lys Arg Leu Val Gly
            20

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Arg Pro Ala Ala Thr Lys Lys Ala Gly Gln Ala Lys Lys Lys Lys
1               5                   10                  15

Leu Glu Ala Tyr Pro Lys Ala Trp Lys
            20                  25
```

```
<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Thr Lys Gly Thr Lys Arg Ser Tyr Glu Gln Met Glu Thr Gly Glu
1               5                   10                  15

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Lys Trp Glu Arg Lys Pro Ile Arg Cys Ala Ser
1               5                   10

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Tyr Gly Lys Arg Thr Ala Asp Ser Gln His Ser Thr Pro Pro Lys
1               5                   10                  15

Lys Lys Arg Lys Val Glu Ala Pro Tyr Lys Ala Trp Lys
                20                  25

<210> SEQ ID NO 29
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Arg Thr Ala Asp Ser Gln His Ser Thr Pro Pro Lys Lys Lys Arg
1               5                   10                  15

Lys Val Glu Ala Pro Tyr Lys Ala Trp Lys
                20                  25

<210> SEQ ID NO 30
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Tyr Gly Pro Pro Lys Lys Arg Lys Val Glu Ala Pro Tyr Lys
1               5                   10                  15

Ala Trp Lys Trp Ala Lys Tyr Pro Ala Met Arg Arg Ala His His Arg
                20                  25                  30
```

Arg Arg Arg Ala Ser His Arg Arg Thr Thr Thr Gly Thr
            35                  40                  45

```
<210> SEQ ID NO 31
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31
```

Gly Tyr Gly Pro Pro Lys Lys Lys Arg Lys Val Glu Ala Pro Tyr Lys
1               5                   10                  15

Ala Trp Lys Arg Gly Ala Arg Arg Tyr Ser Lys Met Lys Arg Arg Arg
            20                  25                  30

Arg Arg Val Ala Arg Arg His Arg Arg Pro
            35                  40

```
<210> SEQ ID NO 32
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

Phe Trp Gly Tyr Gly Tyr Gly Pro Pro Lys Lys Lys Arg Lys Val Glu
1               5                   10                  15

Ala Pro Tyr Lys Ala Trp Lys
            20

```
<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

Gly Lys Pro Ser Ser Asp Asp Glu Ala Thr Ala Asp Ser Gln His Ser
1               5                   10                  15

Thr Pro Pro Lys Lys Lys Glu Arg Lys Val Glu Asp
            20                  25

```
<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

Gly Lys Pro Thr Ala Asp Asp Gln His Ser Thr Pro Pro Lys Lys Lys
1               5                   10                  15

Arg Lys Val Glu Asp
            20

```
<210> SEQ ID NO 35
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Gly Gly Lys Arg Thr Ala Asp Gly Ser Glu Phe Glu Ser Pro Lys Lys
1               5                   10                  15

Ala Arg Lys Val Glu Ala Tyr Pro Lys Ala Lys
            20                  25

<210> SEQ ID NO 36
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Lys Ile Arg Leu Arg Pro Gly Arg Lys Lys Arg Tyr Arg Leu Lys
1               5                   10                  15

His Leu

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Pro Glu Gly Thr Arg Gln Ala Arg Arg Asn Arg Arg Arg Trp Arg
1               5                   10                  15

Lys Arg

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Glu Gly Thr Arg Gln Pro Arg Asn Arg Arg Arg Trp Arg
1               5                   10                  15

Lys Arg

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Val Lys Arg Ser Tyr Gly Ala Ala Arg Gly Asp Asp Arg Arg Arg
1               5                   10                  15

Pro Asn Val Val Ala Pro Tyr Lys Ala Trp
            20                  25

<210> SEQ ID NO 40
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Ser Val Pro Asn Arg Thr Arg Thr Tyr Ile Lys Leu Lys Arg Leu
1               5                   10                  15

Arg Phe Lys Gly Ala Pro Tyr Lys Ala Trp
            20                  25

<210> SEQ ID NO 41
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Met Arg Arg Arg Arg Glu Glu Glu Gly Leu Gln Leu Arg Lys Gln
1               5                   10                  15

Lys Arg Glu Glu Gln Leu Phe Lys Arg Arg Asn
            20                  25

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Glu Ala Ala Leu Ala Glu Ala Leu Ala Glu Ala Leu Ala
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NHCH3

<400> SEQUENCE: 43

Leu Ala Arg Leu Leu Pro Arg Leu Leu Ala Arg Leu
1               5                   10

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Leu Leu Glu Glu Leu Leu Glu Leu Leu Glu Glu Leu Trp Glu Glu
1               5                   10                  15

Leu Leu Glu Gly
```

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Trp Glu Gly Leu Ile Glu Gly Ile Glu Gly Gly Trp Glu Gly Leu
1               5                   10                  15

Ile Glu Gly

<210> SEQ ID NO 46
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Phe Glu Ala Leu Ala Glu Phe Ile Glu Gly Gly Trp Glu Gly
1               5                   10                  15

Leu Ile Glu Gly
            20

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Leu Phe Glu Ala Leu Leu Glu Leu Leu Glu Ser Leu Trp Glu Leu
1               5                   10                  15

Leu Leu Glu Ala
            20

<210> SEQ ID NO 48
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Gly Tyr Cys Leu Glu Lys Trp Met Ile Val Ala Ser Glu Leu Lys
1               5                   10                  15

Cys Phe Gly Asn Thr Ala
            20

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Gly Gly Tyr Cys Leu Thr Arg Trp Met Leu Ile Glu Ala Glu Leu Lys
1               5                   10                  15

Cys Phe Gly Asn Thr Ala Val
            20
```

```
<210> SEQ ID NO 50
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30
```

```
<210> SEQ ID NO 51
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Leu Phe Gly Ala Ile Ala Gly Phe Ile Glu Asn Gly Trp Glu Gly
1               5                   10                  15

Met Ile Asp Gly Trp Tyr Gly
            20
```

```
<210> SEQ ID NO 52
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

```
<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Arg Lys Lys Arg Arg Gln Arg Arg Arg Pro Pro Gln
1               5                   10
```

```
<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 54

Arg Gln Ile Lys Ile Trp Phe Gln Asn Arg Arg Met Lys Trp Lys Lys
1               5                   10                  15

<210> SEQ ID NO 55
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 56
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 57
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Leu Phe Lys Ala Leu Leu Lys Leu Leu Lys Ser Leu Trp Lys Leu
1               5                   10                  15

Leu Leu Lys Ala
            20

<210> SEQ ID NO 58
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Leu Phe Arg Ala Leu Leu Arg Leu Leu Arg Ser Leu Trp Arg Leu
1               5                   10                  15

Leu Leu Arg Ala
            20

<210> SEQ ID NO 59
<211> LENGTH: 20
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 59

Gly Leu Phe Glu Ala Leu Leu Glu Leu Leu Glu Ser Leu Tyr Glu Leu
1               5                   10                  15

Leu Leu Glu Ala
            20

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Phe Glu Ala Leu Glu Glu Leu Trp Glu Ala
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Leu Phe Leu Leu Glu Glu Trp Leu Glu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Leu Phe Leu Leu Glu Glu Trp Leu Glu Lys
1               5                   10

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Leu Phe Glu Ala Leu Leu Glu Leu Leu Glu Ser Leu Trp Glu Leu
1               5                   10                  15

Leu Leu Glu Ala Lys
            20

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: N-term succinyl

<400> SEQUENCE: 64

Gly Leu Phe Lys Leu Leu Glu Glu Trp Leu Glu
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term succinyl

<400> SEQUENCE: 65

Gly Leu Phe Lys Leu Leu Glu Glu Trp Leu Glu Lys
1               5                   10

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Leu Phe Glu Ala Ile Ala Glu Phe Ile Glu Gly Gly Trp Glu Gly
1               5                   10                  15

Leu Ile Glu Gly
            20

<210> SEQ ID NO 67
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Leu Phe Lys Ala Ile Ala Lys Phe Ile Lys Gly Gly Trp Lys Gly
1               5                   10                  15

Leu Ile Lys Gly
            20

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Arg Phe Lys Lys Thr Lys Leu Ile Ala Ser Ile Ala Met Ala Leu
1               5                   10                  15

Cys

<210> SEQ ID NO 69
<211> LENGTH: 30
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 69

Ala Leu Ala Gly Thr Ile Ile Ala Gly Ala Ser Leu Thr Phe Gln Val
1               5                   10                  15

Leu Asp Lys Val Leu Glu Glu Leu Gly Lys Val Ser Arg Lys
            20                  25                  30

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Tyr Ile Cys Arg Arg Ala Arg Gly Asp Asn Pro Asp Asp Arg Cys
1               5                   10                  15

Thr

<210> SEQ ID NO 72
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Leu Phe Glu Ala Ile Ala Glu Phe Ile Glu Gly Gly Trp Glu Gly
1               5                   10                  15

Leu Ile Glu Gly Cys Ala
            20

<210> SEQ ID NO 73
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Phe His Ala Ile Ala His Phe Ile His Gly Gly Trp His Gly
1               5                   10                  15

Leu Ile His Gly Trp Trp Tyr Gly
            20
```

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Arg Arg Arg Gln Arg Arg Lys Lys Arg Gly Gly Asp Ile Met Gly Glu
1               5                   10                  15

Trp Gly Asn Glu Ile Phe Gly Ala Ile Ala Gly Phe Leu Gly
            20                  25                  30

<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Leu Phe Glu Ala Ile Ala Asp Phe Ile Glu Asn Gly Trp Glu Gly
1               5                   10                  15

Met Ile Asp Gly Gly Gly
            20

<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Leu Ala Gly Thr Ile Ile Ala Gly Ala Ser Leu Thr Phe Gln Val
1               5                   10                  15

Leu Asp Lys Val Leu Glu Glu Leu Gly Lys Val Ser Arg Lys Lys
            20                  25                  30

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Arg Phe Lys Lys Thr Lys Leu Ile Ala Ser Ile Ala Met Ala
1               5                   10                  15

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Leu Trp His Leu Leu Leu His Leu Trp Arg Arg Leu Leu Arg Leu
1               5                   10                  15

Leu Arg

<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Lys Ile Met Leu Leu Leu Met Thr Leu Leu Leu Val Ser Leu Pro
1               5                   10                  15

Leu Ala Gln Glu Gln
            20

<210> SEQ ID NO 80
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Leu Phe Glu Ala Leu Leu Glu Leu Leu Glu Ser Leu Trp Glu Leu
1               5                   10                  15

Leu Leu Glu Ala Trp Tyr Gly
            20

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Leu Leu Arg Leu Leu Leu Arg Leu Trp Arg Arg Leu Leu Arg Leu
1               5                   10                  15

Leu Arg

<210> SEQ ID NO 82
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Glu Leu Glu Leu Leu Glu Leu Glu Leu Leu Leu Glu Leu Glu
1               5                   10                  15

Leu Leu Glu Leu Glu Leu Leu Leu Glu Leu
            20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Leu Phe Glu Ala Leu Leu Glu Leu Leu Glu Ser Leu Trp Glu Leu
1               5                   10                  15

Leu Leu Glu Ala Arg Arg Arg Arg Arg Arg
            20                  25

<210> SEQ ID NO 84
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Leu Phe Glu Ala Leu Leu Glu Leu Leu Glu Ser Leu Trp Glu Leu
1               5                   10                  15

Leu Leu Glu Ala Arg Arg Arg Arg Arg Arg
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Leu Phe Glu Ala Leu Leu Glu Leu Leu Glu Ser Leu Trp Glu Leu
1               5                   10                  15

Leu Leu Glu Ala Lys Lys Lys Lys Lys Lys Lys Lys
            20                  25

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Leu Phe Glu Ala Leu Leu Glu Leu Leu Glu Ser Leu Trp Glu Leu
1               5                   10                  15

Leu Leu Glu Ala Lys Lys Lys Lys Lys Lys
            20                  25

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Leu Phe Glu Ala Leu Leu Glu Leu Leu Glu Ser Leu Trp Glu Leu
1               5                   10                  15

Leu Leu Glu Ala Lys Lys
            20

<210> SEQ ID NO 88
<211> LENGTH: 24

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Leu Phe Glu Ala Leu Leu Glu Leu Leu Glu Ser Leu Trp Glu Leu
1               5                   10                  15

Leu Leu Glu Ala Lys Lys Lys Lys
            20

<210> SEQ ID NO 89
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Leu Phe Glu Ala Leu Leu Glu Leu Leu Glu Ser Leu Trp Glu Leu
1               5                   10                  15

Leu Leu Glu Ala Glu Glu
            20

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Leu Phe Glu Ala Leu Leu Glu Leu Leu Glu Ser Leu Trp Glu Leu
1               5                   10                  15

Leu Leu Glu Ala Glu Glu Glu Glu
            20

<210> SEQ ID NO 91
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Leu Phe Glu Ala Leu Leu Glu Leu Leu Glu Ser Leu Trp Glu Leu
1               5                   10                  15

Leu Leu Glu Ala Glu Glu Glu Glu Glu Glu
            20                  25

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Leu Phe Glu Ala Leu Leu Glu Leu Leu Glu Ser Leu Trp Glu Leu
1               5                   10                  15
```

Leu Leu

<210> SEQ ID NO 93
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Pro Leu Ser Ser Ile Phe Ser Arg Ile Gly Asp Pro Arg Gly Ala Arg
1               5                   10                  15

Arg Tyr Ala Lys Met Lys Arg Arg Arg Arg Val Ala Arg Arg His
            20                  25                  30

Arg Arg Arg Pro
        35

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Pro Phe His Tyr Phe Gln Phe Leu Phe Pro Pro Val
1               5                   10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Ser Ser Trp Trp Gln Arg Trp Trp Pro Pro Trp
1               5                   10

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Arg Arg Gln Arg Arg Lys Lys Arg
1               5

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Lys Lys Lys
1

```
<210> SEQ ID NO 98
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Lys Lys Lys Lys Lys
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Lys Lys Lys Lys Lys Lys Lys Lys
1               5

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Lys Lys Lys Lys Lys Lys Lys Lys Lys Lys
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Lys Lys Lys Lys Lys Lys Lys Lys Lys Lys Lys Lys
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Lys Lys Lys Lys Lys Lys Lys Lys Lys Lys Lys Lys Lys Lys Lys
1               5                   10                  15

<210> SEQ ID NO 103
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103
```

```
Lys Lys Lys Lys Lys Lys Lys Lys Lys Lys Lys Lys Lys Lys Lys
1               5                   10                  15

Lys Lys Lys Lys
            20

<210> SEQ ID NO 104
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Lys Lys Lys Lys Lys Lys Lys Lys Lys Lys Lys Lys Lys Lys Lys
1               5                   10                  15

Lys Lys Lys Lys Lys Lys Lys Lys
            20

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Arg Arg Arg
1

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Arg Arg Arg Arg Arg
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Arg Arg Arg Arg Arg Arg Arg
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Arg Arg Arg Arg Arg Arg Arg Arg Arg
1               5                   10
```

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Arg Arg Arg Arg Arg Arg Arg Arg Arg Arg Arg
1               5                   10

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Arg Arg Arg Arg Arg Arg Arg Arg Arg Arg Arg Arg Arg Arg Arg
1               5                   10                  15

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Arg Arg Arg Arg Arg Arg Arg Arg Arg Arg Arg Arg Arg Arg Arg
1               5                   10                  15

Arg Arg Arg Arg
            20

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Arg Arg Arg Arg Arg Arg Arg Arg Arg Arg Arg Arg Arg Arg Arg
1               5                   10                  15

Arg Arg Arg Arg Arg Arg Arg Arg
            20

<210> SEQ ID NO 113
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Tyr Lys Ala
1

<210> SEQ ID NO 114

```
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Lys Lys Lys Lys Lys Lys Lys Lys Trp Lys Gly Gly Gly Gly Ala Cys
1               5                   10                  15

Tyr Gly Leu Pro His Leu Phe Cys Gly
            20                  25

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Tyr Lys Ala Lys Lys Lys Lys Lys Lys Lys Trp Lys
1               5                   10

<210> SEQ ID NO 116
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Lys Thr Pro Lys Lys Ala Lys Lys Pro Lys Thr Pro Lys Lys Ala Lys
1               5                   10                  15

Lys Pro

<210> SEQ ID NO 117
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Lys Ala Lys Lys Pro Ala Ala Thr Arg Lys Ser Ser Lys Asn Pro
1               5                   10                  15

Lys Lys Pro Lys Thr Val Lys Pro Lys Lys Val Ala Lys
            20                  25

<210> SEQ ID NO 118
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Gly Ala Arg Arg Tyr Ser Lys Met Lys Arg Arg Arg Arg Arg Val
1               5                   10                  15

Ala Arg Arg His Arg Arg Arg Pro
            20
```

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Arg Gln Ala Arg Arg Asn Arg Arg Arg Trp Arg Glu Arg Gln
1               5                   10                  15

Arg Gly Ser Gly Ser Gly
            20

<210> SEQ ID NO 120
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Lys Arg Pro Arg Gly Arg Pro Lys Gly Ser Lys Asn Trp Arg Arg
1               5                   10                  15

Arg Lys Arg Arg Ala Ser Arg Arg Ser Pro Arg Arg Arg
            20                  25

<210> SEQ ID NO 121
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Lys Arg Gly Arg Gly Arg Pro Arg Lys Gln Pro Pro Lys Glu Pro Ser
1               5                   10                  15

Glu Val Pro Thr Pro Lys Arg Pro Arg Gly Arg Pro Lys Gly Ser Lys
            20                  25                  30

Asn Lys

<210> SEQ ID NO 122
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Lys Glu Lys Tyr Glu Lys Asp Ile Ala Ala Tyr Arg Ala Lys Gly Lys
1               5                   10                  15

Pro Ala Ala Lys Lys Gly Val Val Lys Ala Glu Lys Ser Lys Lys Lys
            20                  25                  30

Lys

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 123

Tyr Lys Ala Lys Lys Lys Lys Lys Lys Lys Lys Trp Lys
1               5                   10                  15

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Lys Lys Lys Lys Lys Lys Gly Gly Cys
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Tyr Arg Ala Arg Arg Arg Arg Arg Arg Arg Trp Arg
1               5                   10

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Arg Ala Arg Arg Arg Arg Arg Arg Arg Arg Arg Trp Arg
1               5                   10                  15

<210> SEQ ID NO 127
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Lys Gly Asp Pro Lys Lys Pro Arg Gly Lys Met Ser Ser Tyr Ala Phe
1               5                   10                  15

Phe Val Gln Thr Cys Arg Glu Glu His Lys Lys Lys His Pro Asp Ala
            20                  25                  30

Ser Val Asn Phe Ser Glu Phe Ser Lys Lys
        35                  40

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128
```

```
Lys Gln Leu Lys Lys Gln Leu Lys Lys Gln Leu Lys Gln Trp Lys
1               5                   10                  15
```

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Lys Lys Ser Pro Lys Lys Ser Pro Lys Lys Ser Pro Lys Lys Ser Lys
1               5                   10                  15
```

<210> SEQ ID NO 130
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Lys Leu Ser Lys Leu Glu Lys Lys Ser Lys Leu Glu Lys
1               5                   10
```

<210> SEQ ID NO 131
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Lys Leu Ser Lys Leu Glu Lys Lys Leu Ser Lys Leu Glu Lys Lys Ser
1               5                   10                  15

Lys Leu Glu Lys
            20
```

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Lys Ser Leu Lys Lys Ser Leu Lys Lys Ser Leu Lys Lys Ser Lys
1               5                   10                  15
```

<210> SEQ ID NO 133
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

```
Lys Ile Arg Arg Arg Gly Lys Asn Lys Val Ala Ala Arg Thr Cys Arg
1               5                   10                  15

Gln Arg Arg Thr Asp Arg
            20
```

<210> SEQ ID NO 134
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys Ile Arg Arg Arg Gly Lys Asn Lys Val Ala Ala Gln Asn Cys Arg
1               5                   10                  15

Lys Arg Lys Leu Glu Thr
            20

<210> SEQ ID NO 135
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Lys Arg Arg Ile Arg Arg Glu Lys Asn Lys Met Ala Ala Ala Lys Cys
1               5                   10                  15

Arg Asn Arg Arg Arg Glu Leu Thr
            20

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Lys Asp Arg Ser Asn Leu Leu Glu Arg His Thr Arg
1               5                   10

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Arg Pro Ala Ala Thr Lys Lys Ala Gly Gln Ala Lys Lys Lys Leu
1               5                   10                  15

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Arg Arg Arg Arg Arg Arg Glu Glu Glu Glu
1               5                   10

<210> SEQ ID NO 139

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Arg Arg Arg Arg Arg Arg Glu Glu Glu Glu Glu Glu
1               5                   10

<210> SEQ ID NO 140
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Arg Arg Arg Arg Arg Arg Glu Glu Glu Glu Glu Glu Glu Glu
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Arg Arg Arg Arg Arg Arg Arg Glu Glu Glu Glu
1               5                   10

<210> SEQ ID NO 142
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Arg Arg Arg Arg Arg Arg Arg Arg Glu Glu Glu Glu Glu Glu
1               5                   10

<210> SEQ ID NO 143
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Arg Arg Arg Arg Arg Arg Arg Arg Glu Glu Glu Glu Glu Glu Glu Glu
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144
```

Arg Arg Arg Arg Arg Arg Arg Arg Arg Arg Arg Glu Glu Glu Glu
1               5                   10                  15

<210> SEQ ID NO 145
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Arg Arg Arg Arg Arg Arg Arg Arg Arg Arg Arg Glu Glu Glu Glu
1               5                   10                  15

Glu Glu

<210> SEQ ID NO 146
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Arg Arg Arg Arg Arg Arg Arg Arg Arg Arg Glu Glu Glu Glu
1               5                   10                  15

Glu Glu

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Lys Leu Ser Lys Leu Glu Lys Lys
1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Lys Leu Glu Lys
1               5

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Lys Leu Ser Lys Leu Glu Lys Lys Leu Ser Lys Leu Glu Lys Lys
1               5                   10                  15

<210> SEQ ID NO 150

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Pro Lys Lys Lys Arg Lys Val Gly Gly Gly Arg Gly Asp Ser Pro
1               5                   10                  15

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Pro His Lys Ser Met Pro Cys Gly
1               5

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Ala Cys Leu Gln His Lys Ser Met Pro Cys Gly
1               5                   10

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Gly Leu Pro His Leu Phe Cys Gly
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Glu Arg Ser Met Asn Phe Cys Gly
1               5

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155
```

```
Asp His Tyr Ser Leu Tyr Glu Asp Leu Glu Arg Gly Thr Asp Lys
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Ser Leu Pro Arg Thr Ser Gly Ala Gln Arg Ala Ser Thr Thr Arg
1               5                   10                  15

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Lys Leu Gln Thr Lys Tyr Gly Leu Pro His Lys Val Glu Phe Cys
1               5                   10                  15

Gly

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Thr Arg Ile Ser Glu Ser Gln Ala Lys Pro Gly Asp
1               5                   10

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Val Phe Phe Asp Tyr
1               5

<210> SEQ ID NO 160
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Gly Gly Asn Gly Pro Thr Thr Phe Asp Cys Ser Gly Tyr Thr Lys
1               5                   10                  15

Tyr Val Phe Ala Lys
            20
```

```
<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ile Asn Ile Gly Thr Thr Gly Trp Gly Asp His Tyr Ser Leu Tyr
1               5                   10                  15

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Tyr Asp Asn Ile His Gly
1               5

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Gly Trp Gly Lys Phe Leu Val Gly Phe Gly Arg Val
1               5                   10

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ile Gly Tyr Pro Leu Pro
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Thr Thr His Trp Gly Phe Thr Leu
1               5

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166
```

```
His Leu Gln Ile Gln Pro Tyr Pro Gln Ile Ser Gly
1               5                   10

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Leu Asn Ile Val Ser Val Asn Gly
1               5

<210> SEQ ID NO 168
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Gly His
1

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Asp Asn Arg Ile Arg Leu Gln Ala Lys Ala Ala
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Lys Ile Lys Met Val Ile Ser Trp Lys Gly
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Leu Pro Trp Tyr Ser Tyr Leu Tyr Ala Val Ser Ala
1               5                   10

<210> SEQ ID NO 172
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 172

Trp Asn Leu Pro Trp Tyr Tyr Ser Val Ser Pro Thr
1               5                   10

<210> SEQ ID NO 173
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Trp Asn Leu
1

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Pro Trp Tyr Tyr Ser Val Ser Pro Thr
1               5

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Ser Trp Glu Ser Tyr Lys Ser Gly Gly Gly Thr Arg Leu
1               5                   10

<210> SEQ ID NO 176
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Arg Asp Trp Ser Ser Gln His Pro Gly Arg Cys Asn Gly Glu Thr His
1               5                   10                  15

Leu Lys

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Leu Pro Thr Leu Thr Leu
```

<210> SEQ ID NO 178
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Val Ile Cys Thr Gly Gly Asp Tyr Ser Phe Ala Leu Pro Val Gly Gln
1               5                   10                  15

Trp Pro Val Met Thr
            20

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Lys Pro Ser Tyr Gln Phe Gly Gly His Asn Ser Val Asp Phe Glu
1               5                   10                  15

Glu Asp Thr Leu Pro Lys Val
            20

<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ala Arg Arg Arg Lys Arg Ala Ser Ala Thr Gln Leu Tyr Gln Thr
1               5                   10                  15

Cys Lys Ala Ser Gly Thr Cys Pro Pro Asp
            20                  25

<210> SEQ ID NO 181
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Gly Asp Tyr Ser Phe Ala Leu Pro Val Gly Gln Trp Pro Trp Met
1               5                   10                  15

Thr Gly

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

```
Cys Thr Gly Gly Asp Tyr Ser Phe Ala Leu Pro Val Gly Gln Trp Pro
1               5                   10                  15

Trp

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Phe Tyr Tyr Asp Tyr Asp Phe Phe Phe Asp Tyr Trp Gly Gln Gly
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

His Leu Arg Arg Leu Arg Arg Arg Leu Leu Arg Glu Ala Glu Gly
1               5                   10                  15

<210> SEQ ID NO 185
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Tyr Tyr Cys Ala Ala Trp Asp Asp Ser Leu Asn Gly Tyr Ser Val
1               5                   10                  15

Phe

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Tyr Tyr Cys Leu Gln Ser Met Glu Asp Pro Tyr Thr Phe Gly Gly
1               5                   10                  15

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Tyr Tyr Cys Ala Arg Ser Asp Gly Asn Tyr Gly Tyr Tyr Ala Leu
1               5                   10                  15

Asp Tyr Asp Tyr
```

```
<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ala Arg Ser Pro Ser Tyr Tyr Arg Tyr Asp Tyr
1               5                   10

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Pro Tyr Tyr Ala Met Asp Tyr Asp
1               5

<210> SEQ ID NO 190
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Tyr Tyr Cys Gln Gln Arg Ser Ser Tyr Pro Tyr Thr Glu Gly Gly Ala
1               5                   10                  15

Tyr Pro Lys Ala Trp Lys
            20

<210> SEQ ID NO 191
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Tyr Tyr Cys Gln Arg Tyr Asp Ser Asp Trp Ser Phe Gly Gln Gly Thr
1               5                   10                  15

Lys Leu

<210> SEQ ID NO 192
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Tyr Tyr Cys Ala Arg Ser Gly Tyr Tyr Ala Met Asp Tyr Trp Gly Gln
1               5                   10                  15

Gly Thr
```

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Arg Val Arg Arg Gly Ala Cys Arg Gly Asp Cys Leu Gly
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Val Arg Arg Gly Ala Cys Arg Tyr Asp Cys Leu Gly
1               5                   10

<210> SEQ ID NO 195
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Tyr Tyr Cys Ala Lys Gly Thr His Trp Gly Phe Trp Ser Gly Tyr Phe
1               5                   10                  15

Asp Tyr Trp Gly Gln Gly Thr
            20

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Arg Glu Asn Tyr His Gly Cys Thr Thr His Trp Gly Phe Thr Leu
1               5                   10                  15

Cys

<210> SEQ ID NO 197
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Val Gln Ala Thr Gln Ser Asn Gln His Thr Pro Arg Gly Gly Gly Ser
1               5                   10                  15

Lys

<210> SEQ ID NO 198

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Asp Pro Arg Ala Pro Gly Ser
1               5

<210> SEQ ID NO 199
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Tyr Tyr Cys Gln Gln Arg Ser Ser Tyr Pro Tyr Thr Phe Gly Gly
1               5                   10                  15

<210> SEQ ID NO 200
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ala Ala Arg Ser Pro Ser Tyr Tyr Arg Tyr Asp Tyr Gly Pro Tyr Tyr
1               5                   10                  15

Ala Met Asp Tyr Asp
            20

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Pro Lys Leu Thr Gly Ile Leu Ile Ser Ile Leu Ser Leu Phe Val
1               5                   10                  15

Glu Ser

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Lys Tyr Ile Leu Arg Trp Arg Pro Lys Asn Ser
1               5                   10

<210> SEQ ID NO 203
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 203

Ile Lys Val Ala Val
1               5

<210> SEQ ID NO 204
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Thr Pro Pro Arg Ala Gln Ile Thr Gly Tyr Arg Leu Thr Val Gly
1               5                   10                  15

Leu Thr Arg Arg
            20

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Ala Ser Ile Lys Val Ala Val Ser Ala Asp Arg
1               5                   10

<210> SEQ ID NO 206
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Lys Leu Asp Ala Pro Thr
1               5

<210> SEQ ID NO 207
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Asn Arg Trp His Ser Ile Tyr Ile Thr Arg Phe Gly
1               5                   10

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Pro His Ser Arg Asn
```

```
<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Ser Phe His Phe Asp Gly Ser Gly Tyr Ala Met
1               5                   10

<210> SEQ ID NO 210
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Gly Asp Ser
1

<210> SEQ ID NO 211
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ile Ala Phe Gln Arg Asn
1               5

<210> SEQ ID NO 212
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Arg Gly Asp Ser Pro
1               5

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Thr Trp Tyr Lys Ile Ala Phe Gln Arg Arg Lys
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 214

Glu Asp Gly Ile His Glu Leu
1               5

<210> SEQ ID NO 215
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Leu Val Arg Asn Arg Arg Val Ile Thr Ile Gln
1               5                   10

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Tyr Arg Val Arg Val Thr Pro Lys Glu Lys Thr Gly Pro Met Lys Glu
1               5                   10                  15

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Leu Gln Val Gln Leu Ser Arg
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Pro Pro Arg Arg Ala Arg Val Thr
1               5

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Arg Lys Arg Leu Gln Val Gln Leu Ser Ile Arg Thr
1               5                   10

<210> SEQ ID NO 220
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ala Thr Glu Thr Thr Ile Thr Ile Ser
1               5

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asn Ala Pro Phe Pro Lys Leu Ser Trp Thr Ile Gln
1               5                   10

<210> SEQ ID NO 222
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Val Ser Pro Pro Arg Arg Ala Arg Val Thr Asp Ala Thr Glu Thr Thr
1               5                   10                  15

Ile Thr Ile Ser Trp Arg Thr Lys Thr Glu Thr Ile Thr Gly Gly
            20                  25                  30

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Trp Thr Ile Gln Thr Thr Val Asp Arg Gly Leu Leu
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Lys Pro Asp Val Arg Ser Tyr Thr Ile Thr Gly
1               5                   10

<210> SEQ ID NO 225
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 225

Asp Thr Ile Asn Asn Gly Arg Asp His Met Ile Leu Ile
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ala Asn Gly Gln Thr Pro Ile Gln Arg Tyr Ile Lys
1               5                   10

<210> SEQ ID NO 227
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Met Ile Leu Ile Ser Ile Gly Lys Ser Gln Lys Arg Met
1               5                   10

<210> SEQ ID NO 228
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Pro Arg Ala Arg Ile Thr Gly Tyr Ile Ile Lys Tyr Glu Lys Pro Gly
1               5                   10                  15

Ser Pro Pro Arg Glu Val Val Pro Arg Pro Arg Pro Gly Val
            20                  25                  30

<210> SEQ ID NO 229
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Pro Pro Phe Leu Met Leu Leu Lys Gly Ser Thr Arg
1               5                   10

<210> SEQ ID NO 230
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Gln Pro Pro Arg Ala Arg Ile
1               5

<210> SEQ ID NO 231
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Asn Gln Arg Leu Ala Ser Phe Ser Asn Ala Gln Gln Ser
1               5                   10

<210> SEQ ID NO 232
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Trp Gln Pro Pro Arg Ala Arg Ile Thr Gly Tyr Ile Ile Lys Tyr Glu
1               5                   10                  15

Lys Pro Gly

<210> SEQ ID NO 233
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ile Ser Asn Val Phe Val Gln Arg Met Ser Gln Ser Pro Glu Val Leu
1               5                   10                  15

Asp

<210> SEQ ID NO 234
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Tyr Glu Lys Pro Gly Ser Pro Pro Arg Glu Val Val Pro Arg Pro Arg
1               5                   10                  15

Pro Gly Val

<210> SEQ ID NO 235
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Lys Ala Arg Ser Phe Asn Val Asn Gln Leu Leu Gln Asp
1               5                   10

<210> SEQ ID NO 236
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Lys Asn Asn Gln Lys Ser Glu Pro Leu Ile Gly Arg Lys Lys Thr
1               5                   10                  15

<210> SEQ ID NO 237
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Lys Asn Ser Phe Met Ala Leu Tyr Leu Ser Lys Gly
1               5                   10

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Glu Ile Leu Asp Val Pro Ser Thr
1               5

<210> SEQ ID NO 239
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Lys Asn Ser Phe Met Ala Leu Tyr Leu Ser Lys Gly Arg Leu Val Phe
1               5                   10                  15

Ala Leu Gly

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Ile Asp Ala Pro Ser
1               5

<210> SEQ ID NO 241
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241
```

```
Arg Asp Ser Phe Val Ala Leu Tyr Leu Ser Glu Gly His Val Ile Phe
1               5                   10                  15

Ala Gly Leu Gly
            20

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val Val Ile Asp Ala Ser Thr Ala Ile Asp Ala Pro Ser Asn Leu
1               5                   10                  15

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Lys Pro Arg Leu Gln Phe Ser Leu Asp Ile Gln Thr
1               5                   10

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Leu Asp Val Pro Ser
1               5

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Asp Gly Gln Trp His Ser Val Thr Val Ser Ile Lys
1               5                   10

<210> SEQ ID NO 246
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Arg Glu Asp Val
1

<210> SEQ ID NO 247
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Phe Val Leu Tyr Leu Gly Ser Lys Asn Ala Lys Lys
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Pro His Ser Arg Asn Arg Gly Asp Ser Pro
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Leu Ala Ile Lys Asn Asp Asn Leu Val Tyr Val Tyr
1               5                   10

<210> SEQ ID NO 250
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Leu Trp Val Thr Val Arg Ser Gln Gln Arg Gly Leu Phe
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Ala Tyr Phe Ser Ile Val Lys Ile Glu Arg Val Gly
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252
```

```
Gly Thr Asn Asn Trp Trp Gln Ser Pro Ser Ile Gln Asn
1               5                   10
```

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

```
Asp Val Ile Ser Leu Tyr Asn Phe Lys His Ile Tyr
1               5                   10
```

<210> SEQ ID NO 254
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

```
Trp Val Thr Val Thr Leu Asp Leu Arg Gln Val Phe Gln
1               5                   10
```

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

```
Phe Phe Asp Gly Ser Ser Tyr Ala Val Val Arg Asp
1               5                   10
```

<210> SEQ ID NO 256
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

```
Arg Gln Val Phe Gln Val Ala Tyr Ile Ile Ile Lys Ala
1               5                   10
```

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

```
Leu His Val Phe Tyr Asp Phe Gly Phe Gly Phe Ser Asn Gly
1               5                   10
```

<210> SEQ ID NO 258
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 258

Leu Thr Arg Tyr Lys Ile Thr Pro Arg Gly Pro Pro Thr
1               5                   10

<210> SEQ ID NO 259
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Leu Lys Lys Ala Gln Ile Asn Asp Ala Lys Tyr Arg Glu Ile Ser Ile
1               5                   10                  15

Ile Tyr His Asn
            20

<210> SEQ ID NO 260
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Leu Leu Glu Phe Thr Ser Ala Arg Tyr Ile Arg Leu
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Arg Ala Tyr Phe Asn Gly Gln Ser Phe Ile Ala Ser
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Tyr Ile Arg Leu Arg Leu Gln Arg Ile Arg Thr Leu
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ser Arg Leu Arg Gly Lys Asn Pro Thr Lys Gly Lys
```

```
                        1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Arg Arg Tyr Tyr Tyr Ser Ile Lys Asp Ile Ser Val
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Leu His Lys Lys Gly Lys Asn Ser Ser Lys Pro Lys
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Ile Asn Asn Thr Ala Val Asn Gln Arg Leu Thr
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Arg Leu Lys Thr Arg Ser Ser His Gly Met Ile Phe
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Gly Phe Leu Lys Tyr Thr Val Ser Tyr Asp Ile
1               5                   10

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 269

Gly Glu Lys Ser Gln Phe Ser Ile Arg Leu Lys Thr
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Arg Asp Gln Leu Met Thr Val Leu Ala Asn Val Thr
1               5                   10

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Thr Leu Phe Leu Ala His Gly Arg Leu Val Phe Met
1               5                   10

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Ala Asn Val Thr His Leu Leu Ile Arg Ala Asn Tyr
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Leu Val Phe Met Phe Asn Val Gly His Lys Lys Leu
1               5                   10

<210> SEQ ID NO 274
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ala Gly Thr Phe Ala Leu Arg Gly Asp Asn Pro Gln Gly
1               5                   10

<210> SEQ ID NO 275

-continued

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Thr Leu Phe Leu Ala His Gly Arg Leu Val Phe Met Phe Asn Val Gly
1               5                   10                  15

His Lys Lys Leu
            20

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Val Leu Ile Lys Gly Gly Arg Ala Arg Lys His Val
1               5                   10

<210> SEQ ID NO 277
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Asp Phe Met Thr Leu Phe Leu Ala His Gly Arg Leu Val Phe Met Gly
1               5                   10                  15

Asn Val Gly

<210> SEQ ID NO 278
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Leu Ser Asn Ile Asp Tyr Leu Ile Lys Ala Ser
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

His Lys Lys Leu Lys Ile Arg Ser Gln Glu Lys Tyr
1               5                   10

<210> SEQ ID NO 280
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 280

Leu Gln Gln Ser Arg Ile Ala Asn Ile Ser Met Glu
1               5                   10

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gly Ala Ala Trp Lys Ile Lys Gly Pro Ile Tyr Leu
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asn Leu Leu Leu Leu Leu Val Lys Ala Asn Leu Lys
1               5                   10

<210> SEQ ID NO 283
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Val Ile Arg Asp Ser Asn Val Val Gln Leu Asp Val
1               5                   10

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

His Arg Asp Glu Leu Leu Leu Trp Ala Arg Lys Ile
1               5                   10

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gly Leu Ile Tyr Tyr Val Ala His Gln Asn Gln Met
1               5                   10
```

```
<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Lys Arg Arg Ala Arg Asp Leu Val His Arg Ala Glu
1               5                   10

<210> SEQ ID NO 287
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asp Tyr Ala Thr Leu Gln Leu Gln Glu Gly Arg Leu His Phe Met Phe
1               5                   10                  15

Asp Leu Gly

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Gln Phe Gln Glu Ser Val Asp Asn Ile Thr Lys
1               5                   10

<210> SEQ ID NO 289
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Lys Lys Gly Ser Tyr Asn Asn Ile Val Val His Val
1               5                   10

<210> SEQ ID NO 290
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Pro Gly Gly Met Arg Glu Lys Gly Arg Lys Ala Arg
1               5                   10

<210> SEQ ID NO 291
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 291

Ala Asp Asn Leu Leu Phe Tyr Leu Gly Ser Ala Lys
1               5                   10

<210> SEQ ID NO 292
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Met Glu Met Gln Ala Asn Leu Leu Leu Asp Arg Leu
1               5                   10

<210> SEQ ID NO 293
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Ser Ala Lys Phe Ile Asp Phe Leu Ala Ile Glu
1               5                   10

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Leu Ser Glu Ile Lys Leu Leu Ile Ser Ala Arg
1               5                   10

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Lys Val Ser Phe Leu Trp Trp Val Gly Ser Gly Val
1               5                   10

<210> SEQ ID NO 296
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Arg Asp Phe Thr Lys Ala Thr Asn Ile Arg Leu Arg Phe Leu Arg
1               5                   10                  15

<210> SEQ ID NO 297
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ser Tyr Trp Tyr Arg Ile Glu Ala Ser Arg Thr Gly
1               5                   10

<210> SEQ ID NO 298
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ile Ser Thr Val Met Phe Lys Phe Arg Thr Phe Ser
1               5                   10

<210> SEQ ID NO 299
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Tyr Phe Asp Gly Thr Gly Phe Ala Lys Ala Val Gly
1               5                   10

<210> SEQ ID NO 300
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Lys Gln Ala Asn Ile Ser Ile Val Asp Ile Asp Ser Asn
1               5                   10

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Asn Gly Gln Trp His Lys Val Thr Ala Lys Lys Ile
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Phe Ser Thr Arg Asn Glu Ser Gly Ile Ile Leu Leu
```

```
1               5                   10

<210> SEQ ID NO 303
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ala Lys Lys Ile Lys Asn Arg Leu Glu Leu Val Val
1               5                   10

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Arg Arg Gln Thr Thr Gln Ala Tyr Tyr Ala Ile Phe
1               5                   10

<210> SEQ ID NO 305
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Phe Pro Gly Gly Leu Asn Gln Phe Gly Leu Thr Thr Asn
1               5                   10

<210> SEQ ID NO 306
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Tyr Ala Ile Phe Leu Asn Lys Gly Arg Leu Glu Val
1               5                   10

<210> SEQ ID NO 307
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Asn Gln Phe Gly Leu Thr Thr Asn Ile Arg Phe Arg Gly
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 308

Lys Asn Arg Leu Thr Ile Glu Leu Glu Val Arg Thr
1               5                   10

<210> SEQ ID NO 309
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ile Arg Ser Leu Lys Leu Thr Lys Gly Thr Gly Lys Pro
1               5                   10

<210> SEQ ID NO 310
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Gly Leu Leu Phe Tyr Met Ala Arg Ile Asn His Ala
1               5                   10

<210> SEQ ID NO 311
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ala Lys Ala Leu Glu Leu Arg Gly Val Gln Pro Val Ser
1               5                   10

<210> SEQ ID NO 312
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Val Gln Leu Arg Asn Gly Phe Pro Tyr Phe Ser Tyr
1               5                   10

<210> SEQ ID NO 313
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Gly Gln Leu Phe His Val Ala Tyr Ile Leu Ile Lys Phe
1               5                   10

<210> SEQ ID NO 314

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

His Lys Ile Lys Ile Val Arg Val Lys Gln Glu Gly
1               5                   10

<210> SEQ ID NO 315
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asn Val Leu Ser Leu Tyr Asn Phe Lys Thr Thr Phe
1               5                   10

<210> SEQ ID NO 316
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Asp Phe Gly Thr Val Gln Leu Arg Asn Gly Phe Pro Phe Phe Ser Tyr
1               5                   10                  15

Asp Leu Gly

<210> SEQ ID NO 317
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ser Gln Arg Ile Tyr Gln Phe Ala Lys Leu Asn Tyr Thr
1               5                   10

<210> SEQ ID NO 318
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Asn Ile Arg Leu Arg Phe Leu Arg Thr Asn Thr Leu
1               5                   10

<210> SEQ ID NO 319
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 319

Glu Val Asn Val Thr Leu Asp Leu Gly Gln Val Phe His
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Lys Asn Thr Gly Asp His Phe Val Leu Tyr Met
1               5                   10

<210> SEQ ID NO 321
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gly Gln Val Phe His Val Ala Tyr Val Leu Ile Lys Phe
1               5                   10

<210> SEQ ID NO 322
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Val Val Ser Leu Tyr Asn Phe Glu Gln Thr Phe Met Leu
1               5                   10

<210> SEQ ID NO 323
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

His Gln Gln Asp Leu Gly Thr Ala Gly Ser Cys Leu Arg Lys Phe Ser
1               5                   10                  15

Thr Met Phe Leu Phe
            20

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Arg Phe Asp Gln Glu Leu Arg Leu Val Ser Tyr Asn
1               5                   10
```

<210> SEQ ID NO 325
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

His Gln Gln Asp Leu Gly Thr Ala Gly Ser Cys Leu Arg Lys Phe Ser
1               5                   10                  15

Thr Met Phe Leu Phe Cys Asn Ile
            20

<210> SEQ ID NO 326
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Arg Leu Val Ser Tyr Ser Gly Val Leu Phe Phe Leu Lys
1               5                   10

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Val Ala Glu Ile Asp Gly Ile Glu Leu
1               5

<210> SEQ ID NO 328
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Asn Trp Arg His Ile Ser Tyr Ile Thr Arg Phe Gly
1               5                   10

<210> SEQ ID NO 329
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Ile Ile Phe Phe Leu
1               5

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 330

Lys Arg Leu Gln Val Gln Leu Arg Ser Ile Arg Thr
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ala Ser Lys Ala Ile Gln Val Phe Leu Leu Gly Gly
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Thr Trp Tyr Lys Ile Ala Phe Gln Arg Asn Arg Lys
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Val Leu Val Arg Val Glu Arg Ala Thr Val Phe Ser
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gln Val Phe Gln Val Ala Tyr Ile Ile Ile Lys Ala
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Thr Val Phe Ser Val Asp Gln Asp Asn Met Leu Glu
1               5                   10

<210> SEQ ID NO 336
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Glu Phe Tyr Phe Asp Leu Arg Leu Lys Gly Asp Lys
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Leu Arg Gly Pro Gln Arg Val Phe Asp Leu His
1               5                   10

<210> SEQ ID NO 338
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Thr Pro Gly Pro Gln Gly Ile Ala
1               5

<210> SEQ ID NO 339
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Phe Asp Leu His Gln Asn Met Gly Ser Val Asn
1               5                   10

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Gln Arg Asp Val Val
1               5

<210> SEQ ID NO 341
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341
```

Leu Arg Ala His Ala Val Asp Val Asn Gly
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Thr Ala Gly Ser Cys Leu Arg Lys Phe Ser Thr Met
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Leu Phe Ser His Ala Val Ser Ser Asn Gly
1               5                   10

<210> SEQ ID NO 344
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Lys Gly His Arg Gly Phe
1               5

<210> SEQ ID NO 345
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Thr Ala Gly Ser Cys Leu Arg Lys Phe Ser Thr Met Phe Leu Phe
1               5                   10                  15

<210> SEQ ID NO 346
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Thr Ala Gly Ser Cys Leu Arg Lys Phe Ser Thr Met Phe Leu Phe Cys
1               5                   10                  15

Asn Ile

<210> SEQ ID NO 347
<211> LENGTH: 15
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 347

Asp Leu Gly Thr Ala Gly Ser Cys Leu Arg Lys Phe Ser Thr Met
1               5                   10                  15

<210> SEQ ID NO 348
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

His Gln Gln Asp Leu Gly Thr Ala Gly Ser Cys Leu Arg Lys Phe Ser
1               5                   10                  15

Thr Met

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Arg Asn Ile Ala Glu Ile Ile Lys Asp Ile
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ser Ile Gly Phe Arg Gly Asp Gly Gln Thr Cys
1               5                   10

<210> SEQ ID NO 351
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Leu Asn Arg Gln Glu Leu Phe Pro Phe Gly
1               5                   10

<210> SEQ ID NO 352
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

```
Arg Ile Gln Asn Leu Leu Lys Ile Thr Asn Leu Arg Ile Lys Phe Val
1               5                   10                  15
Lys

<210> SEQ ID NO 353
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Lys Lys Gln Arg Phe Arg His Arg Asn Arg Lys Gly Tyr Arg Ser Gln
1               5                   10                  15

<210> SEQ ID NO 354
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ser Ile Asn Asn Thr Ala Val Met Gln Arg Leu Thr
1               5                   10

<210> SEQ ID NO 355
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Phe Arg His Arg Asn Arg Lys Gly Tyr
1               5

<210> SEQ ID NO 356
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Arg Tyr Arg Val Arg Val Thr Pro Lys Glu Lys Thr Gly Pro Met Lys
1               5                   10                  15
Glu

<210> SEQ ID NO 357
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Ser Glu Thr Thr Val Lys Tyr Ile Phe Arg Leu His Glu
1               5                   10

<210> SEQ ID NO 358
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly His Arg Gly Pro Thr Gly Arg Pro Gly Lys Arg Gly Lys Gln Gly
1               5                   10                  15

Gln Lys Gly Asp Ser
            20

<210> SEQ ID NO 359
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Lys Ala Phe Asp Ile Thr Tyr Val Arg Leu Lys Phe
1               5                   10

<210> SEQ ID NO 360
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Gly Asp Leu Gly Arg Pro Gly Arg Lys Gly Arg Pro Gly Pro Pro
1               5                   10                  15

<210> SEQ ID NO 361
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Tyr Ile Gly Ser Arg
1               5

<210> SEQ ID NO 362
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Gly Glu Phe Tyr Phe Asp Leu Arg Leu Lys Gly Asp Lys
1               5                   10

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 363

Leu Ala Gly Ser Cys Leu Ala Arg Phe Ser Thr Met
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Leu Ala Leu Phe Leu Ser Asn Gly His Phe Val Ala
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ile Ser Arg Cys Gln Val Cys Met Lys Lys Arg His
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Pro Gly Arg Trp His Lys Val Ser Val Arg Trp Glu
1               5                   10

<210> SEQ ID NO 367
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Thr Asp Ile Pro Pro Cys Pro His Gly Trp Ile Ser Leu Trp Lys
1               5                   10                  15

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Val Arg Trp Gly Met Gln Gln Ile Gln Leu Val Val
1               5                   10

<210> SEQ ID NO 369
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Thr Ala Ile Pro Ser Cys Pro Glu Gly Thr Val Pro Leu Tyr Ser
1               5                   10                  15

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Lys Met Pro Tyr Val Ser Leu Glu Leu Glu Met Arg
1               5                   10

<210> SEQ ID NO 371
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Gly Pro Ala Gly Lys Asp Gly Glu Ala Gly Ala Gln Gly
1               5                   10

<210> SEQ ID NO 372
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Val Leu Leu Gln Ala Asn Asp Gly Ala Gly Glu Phe
1               5                   10

<210> SEQ ID NO 373
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Gly Leu Pro Gly Glu Arg
1               5

<210> SEQ ID NO 374
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Asp Gly Arg Trp His Arg Val Ala Val Ile Met Gly
```

```
1               5                   10
```

<210> SEQ ID NO 375
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

```
Leu Ala Gly Ser Cys Leu Pro Val Phe Ser Thr Leu
1               5                   10
```

<210> SEQ ID NO 376
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

```
Ala Pro Val Asn Val Thr Ala Ser Val Gln Ile Gln
1               5                   10
```

<210> SEQ ID NO 377
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

```
Thr Ala Gly Ser Cys Leu Arg Arg Phe Ser Thr Met
1               5                   10
```

<210> SEQ ID NO 378
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

```
Lys Gln Gly Lys Ala Leu Thr Gln Arg His Ala Lys
1               5                   10
```

<210> SEQ ID NO 379
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

```
Thr Ala Gly Ser Cys Leu Arg Lys Phe
1               5
```

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 380

Arg Tyr Val Val Leu Pro Arg
1               5

<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Thr Ala Gly Ser Cys Leu
1               5

<210> SEQ ID NO 382
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ser Pro Tyr Thr Phe Ile Asp Ser Leu Val Leu Met Pro Tyr
1               5                   10

<210> SEQ ID NO 383
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Thr Ala Gly
1

<210> SEQ ID NO 384
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Pro Asp Ser Gly Arg
1               5

<210> SEQ ID NO 385
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Gln Gln Asn Leu Gly Ser Val Asn Val Ser Thr Gly
1               5                   10

<210> SEQ ID NO 386

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ser Arg Ala Thr Ala Gln Lys Val Ser Arg Arg Ser
1               5                   10

<210> SEQ ID NO 387
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Asp Pro Gly Tyr Ile Gly Ser Arg
1               5

<210> SEQ ID NO 388
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Ser Leu Ser Ser His Leu Glu Phe Val Gly Ile
1               5                   10

<210> SEQ ID NO 389
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Val Ile Leu Gln Gln Ser Ala Ala Asp Ile Ala Arg
1               5                   10

<210> SEQ ID NO 390
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Arg Asn Arg Leu His Leu Ser Met Leu Val Arg Pro
1               5                   10

<210> SEQ ID NO 391
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391
```

```
Lys Asp Ile Ser Glu Lys Val Ala Val Tyr Ser Thr
1               5                   10

<210> SEQ ID NO 392
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Pro Met Ser Gly Arg Ser Pro Ser Leu Val Leu Lys
1               5                   10

<210> SEQ ID NO 393
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Leu Gly Thr Ile Pro Gly
1               5

<210> SEQ ID NO 394
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Phe Gly Val Leu Ala Leu Trp Gly Thr Arg Val
1               5                   10

<210> SEQ ID NO 395
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Thr Asp Ile Arg Val Thr Leu Asn Arg Leu Asn Thr Phe
1               5                   10

<210> SEQ ID NO 396
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Ile Glu Asn Val Val Thr Thr Phe Ala Pro Asn Arg
1               5                   10

<210> SEQ ID NO 397
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 397

Ala Phe Ser Thr Leu Glu Gly Arg Pro Ser Ala Tyr
1               5                   10

<210> SEQ ID NO 398
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Leu Glu Ala Glu Phe His Phe Thr His Leu Ile Met
1               5                   10

<210> SEQ ID NO 399
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Thr Ser Ala Glu Ala Tyr Asn Leu Leu Leu Arg Thr
1               5                   10

<210> SEQ ID NO 400
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

His Leu Ile Met Thr Phe Lys Thr Phe Arg Pro Ala
1               5                   10

<210> SEQ ID NO 401
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Leu Asn Arg Arg Tyr Glu Gln Ala Arg Asn Ile Ser
1               5                   10

<210> SEQ ID NO 402
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Lys Thr Trp Gly Val Tyr Arg Tyr Phe Ala Tyr Asp
1               5                   10
```

-continued

```
<210> SEQ ID NO 403
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ser Leu Leu Ser Gln Leu Asn Asn Leu Leu Asp Gln
1               5                   10

<210> SEQ ID NO 404
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Thr Asn Leu Arg Ile Lys Phe Val Lys Leu His Thr
1               5                   10

<210> SEQ ID NO 405
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Arg Asp Ile Ala Glu Ile Ile Lys Asp Ile
1               5                   10

<210> SEQ ID NO 406
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Lys Arg Leu Val Thr Gly Gln Arg
1               5

<210> SEQ ID NO 407
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Ser His Ala Val Ser Ser
1               5

<210> SEQ ID NO 408
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408
```

```
Gly Pro Gly Val Val Val Glu Arg Gln Tyr Ile
1               5                   10
```

<210> SEQ ID NO 409
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

```
Ala Asp Thr Pro Pro Val
1               5
```

<210> SEQ ID NO 410
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

```
Asn Glu Pro Lys Val Leu Lys Ser Tyr Tyr Tyr Ala Ile
1               5                   10
```

<210> SEQ ID NO 411
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

```
Leu Arg Ala His Ala Val Asp Ile Asn Gly
1               5                   10
```

<210> SEQ ID NO 412
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

```
Tyr Tyr Ala Ile Ser Asp Phe Ala Val Gly Gly Arg
1               5                   10
```

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

```
Asp Ser Ile Thr Lys Tyr Phe Gln Met Ser Leu Glu
1               5                   10
```

<210> SEQ ID NO 414
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 414

Leu Pro Phe Phe Asn Asp Arg Pro Trp Arg Arg Ala Thr
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Tyr Thr Ala Leu Ile Ile Ala Thr Asp Asn
1               5                   10

<210> SEQ ID NO 416
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Phe Asp Pro Glu Leu Tyr Arg Ser Thr Gly His Gly Gly His
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Val Ile Thr Val Lys Asp Ile Asn Asp Asn
1               5                   10

<210> SEQ ID NO 418
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Thr Asn Ala Val Gly Tyr Ser Val Tyr Asp Ile Ser
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Gly Leu Asp Arg Glu Ser Tyr Pro Tyr Tyr
1               5                   10
```

<210> SEQ ID NO 420
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Ala Pro Val Lys Phe Leu Gly Asn Gln Val Leu Ser Tyr
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Met Lys Val Ser Ala Thr Asp Ala Asp Asp
1               5                   10

<210> SEQ ID NO 422
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Ser Phe Ser Phe Arg Val Asp Arg Arg Asp Thr Arg
1               5                   10

<210> SEQ ID NO 423
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Pro Gln Val Thr Arg Gly Asp Val Phe Thr Met Pro
1               5                   10

<210> SEQ ID NO 424
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Thr Trp Ser Lys Val Gly Gly His Leu Arg Pro Gly Ile Val Gln Ser
1               5                   10                  15

Gly

<210> SEQ ID NO 425
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

Lys Glu Ala Glu Arg Glu Val Thr Asp Leu Leu Arg
1               5                   10

<210> SEQ ID NO 426
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Arg Gly Asp Val
1

<210> SEQ ID NO 427
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ala Ala Glu Pro Leu Lys Asn Ile Gly Ile Leu Phe
1               5                   10

<210> SEQ ID NO 428
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Phe Ala Leu Trp Asp Ala Ile Ile Gly Glu Leu
1               5                   10

<210> SEQ ID NO 429
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Val Gly Val Ala Pro Gly
1               5

<210> SEQ ID NO 430
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Leu Trp Pro Leu Leu Ala Val Leu Ala Ala Val Ala
1               5                   10

<210> SEQ ID NO 431

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Pro Gly Val Gly Val
1               5

<210> SEQ ID NO 432
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Val Phe Asp Asn Phe Val Leu Lys
1               5

<210> SEQ ID NO 433
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Thr Ser Ile Lys Ile Arg Gly Thr Tyr Ser Glu Arg
1               5                   10

<210> SEQ ID NO 434
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Thr Thr Ser Trp Ser Gln Cys Ser Lys Ser
1               5                   10

<210> SEQ ID NO 435
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Asp Pro Glu Thr Gly Val
1               5

<210> SEQ ID NO 436
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436
```

```
Lys Arg Ser Arg
1

<210> SEQ ID NO 437
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Gln Gly Ala Asp Thr Pro Pro Val Gly Val
1               5                   10

<210> SEQ ID NO 438
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Ser Val Val Tyr Gly Leu Arg
1               5

<210> SEQ ID NO 439
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Pro Leu Asp Arg Glu Ala Ile Ala Lys Tyr
1               5                   10

<210> SEQ ID NO 440
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Asp Gly Arg Gly Asp Ser Val Ala Tyr Gly
1               5                   10

<210> SEQ ID NO 441
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

His Ala Val Asp Ile
1               5

<210> SEQ ID NO 442
<211> LENGTH: 10
<212> TYPE: PRT
<213> ORGANISM: Artificial Sequence
<220> FEATURE:
```

<223> OTHER INFORMATION: Description of Artificial Sequence: Synthetic
       peptide

<400> SEQUENCE: 442

Leu Ala Leu Glu Arg Lys Asp His Ser Gly
1               5                   10

<210> SEQ ID NO 443
<211> LENGTH: 5
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 443

Asp Gln Asn Asp Asn
1               5

<210> SEQ ID NO 444
<211> LENGTH: 19
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 444

Tyr Ser Met Lys Lys Thr Thr Met Lys Ile Ile Pro Phe Asn Arg Leu
1               5                   10                  15

Thr Ile Gly

<210> SEQ ID NO 445
<211> LENGTH: 10
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 445

Gln Asp Pro Glu Leu Pro Asp Lys Asn Met
1               5                   10

<210> SEQ ID NO 446
<211> LENGTH: 4
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 446

Arg Gly Asp Phe
1

<210> SEQ ID NO 447
<211> LENGTH: 10
<212> TYPE: PRT
<213> ORGANISM: Artificial Sequence
<220> FEATURE:
<223> OTHER INFORMATION: Description of Artificial Sequence: Synthetic
       peptide

<400> SEQUENCE: 447

Leu Val Val Gln Ala Ala Asp Leu Gln Gly
1               5                   10

<210> SEQ ID NO 448
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gly Val Tyr Tyr Gln Gly Gly Thr Tyr Ser Lys Ala Ser
1               5                   10

<210> SEQ ID NO 449
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Asn Asp Asp Gly Gly Gln Phe Val Val Thr
1               5                   10

<210> SEQ ID NO 450
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Thr Ala Gly Ser Cys Leu Arg Lys Phe Ser Cys Leu
1               5                   10

<210> SEQ ID NO 451
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Tyr Ile Leu His Val Ala Val Thr Asn
1               5

<210> SEQ ID NO 452
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Cys Asn Tyr Tyr Ser Asn Ser Tyr Ser Phe Trp Leu Ala Ser Leu Asn
1               5                   10                  15

Pro Glu Arg

<210> SEQ ID NO 453
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 453

Thr Tyr Arg Ile Trp Arg Asp Thr Ala Asn
1               5                   10

<210> SEQ ID NO 454
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 454

Thr Gly Leu Ser Cys Leu Gln Arg Phe Thr Thr Met
1               5                   10

<210> SEQ ID NO 455
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Gly Phe Thr Cys Glu Cys Ser Ile Gly Phe Arg Gly Asp Gly Gln Thr
1               5                   10                  15

Cys Tyr Gly Ile Val Phe Trp Ser Glu Val
            20                  25

<210> SEQ ID NO 456
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

His His Leu Gly Gly Ala Lys Gln Ala Gly Asp Val
1               5                   10

<210> SEQ ID NO 457
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Ser Cys Leu Pro Gly Phe Ser Gly Asp Gly Arg Ala Cys Arg Asp Val
1               5                   10                  15

Asp Glu Cys Gly His
            20

<210> SEQ ID NO 458
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 458

Met Ala Pro Arg Pro Ser Leu Ala Lys Lys Gln Arg Phe Arg His Arg
1               5                   10                  15

Asn Arg Lys Gly Tyr Arg Ser Gln Arg Gly His Ser Arg Gly
            20                  25                  30

<210> SEQ ID NO 459
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Lys Lys Gln Lys Phe Arg His Arg Asn Arg Lys Gly Tyr Arg Ser Gln
1               5                   10                  15

<210> SEQ ID NO 460
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Lys Lys Gln Lys Phe Lys His Arg Asn Arg Lys Gly Tyr Arg Ser
1               5                   10                  15

<210> SEQ ID NO 461
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Lys Lys Gln Lys Phe Arg Arg Arg Asn Arg Lys Gly Tyr Arg Ser His
1               5                   10                  15

<210> SEQ ID NO 462
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Thr Ala Ile Pro Pro Cys Pro His Gly Trp Ile Ser Leu Trp Lys
1               5                   10                  15

<210> SEQ ID NO 463
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Lys Lys Gln Lys Ser Arg His Arg Ser Arg Lys Arg Tyr Arg Ser
1               5                   10                  15
```

```
<210> SEQ ID NO 464
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Lys Lys Gln Lys Ser Arg Arg Arg Ser Arg Lys Gly Tyr Arg Ser
1               5                   10                  15

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Ile Ser Arg Cys Thr Val Cys
1               5

<210> SEQ ID NO 466
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 466

Ile Ser Arg Cys Gln Val Cys Met Lys Arg Arg His
1               5                   10

<210> SEQ ID NO 467
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Val Ser Arg Cys Thr Val Cys
1               5

<210> SEQ ID NO 468
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 468

Thr Asp Ile Pro Pro Cys Pro Gln Gly Trp Ile Ser Leu Trp Lys
1               5                   10                  15

<210> SEQ ID NO 469
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469
```

-continued

```
Thr Val Lys Ala Gly Glu Leu Glu Lys Ile Ile Ser Arg Cys Gln Val
1               5                   10                  15

Met Lys Lys Arg His
            20

<210> SEQ ID NO 470
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Thr Asp Ile Pro Ser Cys Pro His Gly Trp Ile Ser Leu Trp Lys
1               5                   10                  15

<210> SEQ ID NO 471
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 471

Thr Asp Ile Pro Pro Cys Pro Ala Gly Trp Ile Ser Leu Trp Lys
1               5                   10                  15

<210> SEQ ID NO 472
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Thr Glu Ile Pro Pro Cys Pro Gln Gly Trp Ile Ser Leu Trp Lys
1               5                   10                  15

<210> SEQ ID NO 473
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Thr Asp Val Pro Pro Cys Pro Gln Gly Trp Ile Ser Leu Trp Lys
1               5                   10                  15

<210> SEQ ID NO 474
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Arg Leu Val Ser Tyr Asn Gly Ile Leu Phe Phe Leu Lys
1               5                   10

<210> SEQ ID NO 475
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 475

Arg Leu Val Ser Tyr Ser Gly Val Ile Phe Phe Leu Lys
1               5                   10

<210> SEQ ID NO 476
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Arg Leu Val Ser Tyr Asn Gly Ile Leu Phe Phe Leu
1               5                   10

<210> SEQ ID NO 477
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Arg Leu Val Ser Tyr Ser Gly Ile Ile Phe Phe Leu Lys
1               5                   10

<210> SEQ ID NO 478
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Arg Phe Glu Gln Glu Leu Arg Leu Val Ser Tyr Ser Gly Val Leu Phe
1               5                   10                  15

Phe Leu Lys Gln
            20

<210> SEQ ID NO 479
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Arg Leu Val Ser Tyr Asn Gly Ile Ile Phe Phe Leu Lys
1               5                   10

<210> SEQ ID NO 480
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 480

Asp Pro Ala Phe Lys Ile Glu Asp Pro Tyr Ser Pro Arg Ile Gln Asn
1               5                   10                  15

Leu Leu Lys Ile Thr Asn Leu Arg Ile Lys Phe Val Lys Leu
            20                  25                  30

<210> SEQ ID NO 481
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Thr Lys Arg Phe Glu Gln Glu Leu Arg Leu Val Ser Tyr Ser Gly Val
1               5                   10                  15

Leu Phe Phe Leu
            20

<210> SEQ ID NO 482
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gly Gly Arg Leu Lys Tyr Ser Val Ala Phe
1               5                   10

<210> SEQ ID NO 483
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Gly Gly Phe Leu Arg Tyr Thr Val Ser Tyr Asp Ile
1               5                   10

<210> SEQ ID NO 484
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Gly Phe Leu Lys Tyr Thr Val Ser Tyr Asp Val
1               5                   10

<210> SEQ ID NO 485
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485
```

```
Leu Gly Asn Lys Leu Thr Ala Phe Gly Gly Phe Leu Lys Tyr Thr Val
1               5                   10                  15

Ser Tyr Asp Ile Pro Val
            20
```

<210> SEQ ID NO 486
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

```
Gly Gly Tyr Leu Lys Tyr Thr Val Ser Tyr Asp Ile
1               5                   10
```

<210> SEQ ID NO 487
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

```
Gly Glu Ile Phe Phe Asp Met Arg Leu Lys Gly Asp Lys
1               5                   10
```

<210> SEQ ID NO 488
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

```
Gly Glu Ile Tyr Phe Asp Leu Arg Leu Lys Gly Asp Lys
1               5                   10
```

<210> SEQ ID NO 489
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

```
Gly Glu Ile Tyr Leu Asp Met Arg Leu Lys Gly Asp Lys
1               5                   10
```

<210> SEQ ID NO 490
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

```
Ile Gly Gln Pro Gly Ala Lys Gly Glu Pro Gly Glu Phe Tyr Phe Asp
1               5                   10                  15

Leu Arg Leu Lys Gly Asp Lys Gly Asp Pro Gly Phe Pro Gly
            20                  25                  30
```

```
<210> SEQ ID NO 491
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Gly Glu Val Phe Phe Asp Met Arg Leu Lys Gly Asp Lys
1               5                   10

<210> SEQ ID NO 492
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Leu Ala Gly Ser Cys Leu Pro Ile Phe Ser Thr Leu
1               5                   10

<210> SEQ ID NO 493
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Ala His Asn Gln Asp Leu Gly Leu Ala Gly Ser Cys Leu Ala Arg Phe
1               5                   10                  15

Ser Thr Met Pro Phe Leu Tyr Cys Asn Pro Gly Asp Ile Cys
            20                  25                  30

<210> SEQ ID NO 494
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Gln Glu Lys Ala His Asn Gln Asp Leu Gly Leu Ala Gly Ser Cys Leu
1               5                   10                  15

Pro Val Phe Ser Thr Leu Pro Phe Ala Tyr Cys Asn Ile His
            20                  25                  30

<210> SEQ ID NO 495
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Leu Ala Gly Ser Cys Leu Pro Val Phe Ser Thr Met
1               5                   10

<210> SEQ ID NO 496
<211> LENGTH: 30
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Gly Asn Lys Arg Ala His Gly Gln Asp Leu Gly Thr Ala Gly Ser Cys
1               5                   10                  15

Leu Arg Arg Phe Ser Thr Met Pro Phe Met Phe Cys Asn Ile
            20                  25                  30

<210> SEQ ID NO 497
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Arg Ala His Gly Gln Asp Leu Gly Thr Ala Gly Ser Cys Leu Arg Arg
1               5                   10                  15

Phe Ser Thr Met Pro
            20

<210> SEQ ID NO 498
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Arg Lys Arg Leu Gln Val Gln Leu Asn Ile Arg Thr
1               5                   10

<210> SEQ ID NO 499
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 499

His Leu Val Leu Pro Leu Gln Gln Ser Asp Val Arg Lys Arg Leu Gln
1               5                   10                  15

Val Gln Leu Ser Ile Arg Thr Phe Ala Ser Ser Gly Leu Ile
            20                  25                  30

<210> SEQ ID NO 500
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 500

Arg Lys Arg Leu Ser Val Gln Leu Arg Ile Arg Thr
1               5                   10

<210> SEQ ID NO 501
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Asp Leu Gly Thr Ala Gly Ser Cys Leu Arg Arg Phe Ser Thr Met
1               5                   10                  15

<210> SEQ ID NO 502
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Arg Asn Ile Ala Glu Ile Ile Lys Asp Ile
1               5                   10

<210> SEQ ID NO 503
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 503

Thr Ala Gly Ser Cys Leu Arg Lys Phe Ser Thr Met Arg Arg Arg
1               5                   10                  15

Arg Arg Arg Arg Arg Arg Arg Arg
            20

<210> SEQ ID NO 504
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Phe Thr Leu Thr Gly Leu Leu Gly Thr Leu Val Thr Met Gly Leu Leu
1               5                   10                  15

Thr

<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Ala Pro Tyr Lys Ala Trp Lys
1               5

<210> SEQ ID NO 506
<211> LENGTH: 23
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 506

Ser Thr Ser Lys Thr Asn Arg Gly Asp Asp Ser Asn Trp Ser Lys Arg
1               5                   10                  15

Val Thr Asn Asn Lys Pro Ser
            20

<210> SEQ ID NO 507
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ser Thr Ser Lys Arg Lys Arg Gly Asp Asp Ser Asn Trp Ser Lys Arg
1               5                   10                  15

Val Thr Lys Lys Lys Pro Ser
            20

<210> SEQ ID NO 508
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Ser Thr Ser Lys Arg Lys Arg Gly Asp Asp Ser Asn Trp Ser Lys Arg
1               5                   10                  15

Val Ser Lys Lys Lys Pro Ser
            20

<210> SEQ ID NO 509
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Ser Thr Ser Lys Arg Lys Arg Gly Asp Asp Ala Asn Trp Ser Lys Arg
1               5                   10                  15

Val Thr Lys Lys Lys Pro Ser
            20

<210> SEQ ID NO 510
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Pro Leu Ala Gly Ser Lys Arg Lys Arg Ala Asp Glu Val Ala Trp Ser
1               5                   10                  15

Lys Arg Gly Thr Lys Lys Lys Pro Glu Arg
            20                  25

```
<210> SEQ ID NO 511
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Pro Leu Ala Gly Ser Lys Arg Lys Arg Ala Asp Glu Val Ala Trp Ser
1               5                   10                  15

Lys Arg Gly Thr Lys Lys Lys Pro Glu Arg Thr Ser Ala Ala Arg Ala
                20                  25                  30

Gly Pro Ser Arg Arg Ile Arg
            35

<210> SEQ ID NO 512
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Ser Thr Ser Lys Arg Lys Arg Gly Asp Asp Ala Asn Trp Ser Lys Arg
1               5                   10                  15

Thr Thr Lys Lys Lys Pro Ser Ser
                20

<210> SEQ ID NO 513
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Ser Thr Ser Lys Arg Lys Arg Gly Asp Asp Ala Asn Trp Ser Lys Arg
1               5                   10                  15

Thr Thr Lys Lys Lys Pro Ser Ser Ala Gly Leu Lys Arg Ala Gly Ser
                20                  25                  30

Lys Ala Asp Arg Pro Ser Leu
            35

<210> SEQ ID NO 514
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Pro Thr Thr Ala Gly Lys Arg Lys Arg Ser Asp Asp Ala Ala Trp Ser
1               5                   10                  15

Lys Arg Ala Arg Pro Lys Ala Gly Arg Thr
                20                  25

<210> SEQ ID NO 515
<211> LENGTH: 39
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 515

Pro Thr Thr Ala Gly Lys Arg Lys Arg Ser Asp Asp Ala Ala Trp Ser
1               5                   10                  15

Lys Arg Ala Arg Pro Lys Ala Gly Arg Thr Ser Ala Ala Arg Pro Gly
            20                  25                  30

Thr Ser Val Arg Arg Ile Arg
        35

<210> SEQ ID NO 516
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Ser Ser Ser Leu Gly Lys Arg Lys Arg Ser Asp Glu Gly Ala Trp Ser
1               5                   10                  15

Lys Gly Lys Ser Lys Lys Lys Ala Met Arg
            20                  25

<210> SEQ ID NO 517
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 517

Ser Ser Ser Leu Gly Lys Arg Lys Arg Ser Asp Glu Gly Ala Trp Ser
1               5                   10                  15

Lys Gly Lys Ser Lys Lys Lys Ala Met Arg Gly Ser Ser Ser Arg Arg
            20                  25                  30

Pro Gly Pro Val Arg Gly Pro
        35

<210> SEQ ID NO 518
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Pro Thr Thr Ala Gly Lys Arg Lys Arg Thr Asp Asp Ala Ala Trp Ser
1               5                   10                  15

Lys Arg Ala Arg Pro Lys Ala Gly Arg
            20                  25

<210> SEQ ID NO 519
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

```
Pro Thr Thr Ala Gly Lys Arg Lys Arg Thr Asp Asp Ala Ala Trp Ser
 1               5                  10                  15

Lys Arg Ala Arg Pro Lys Ala Gly Arg Thr Ser Ala Ala Arg Pro Gly
            20                  25                  30

Thr Ala Val Arg Arg Val Arg
        35
```

<210> SEQ ID NO 520
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

```
Pro Ala Thr Ala Gly Lys Arg Lys Arg Ser Asp Ala Ala Trp Ser
 1               5                  10                  15

Lys Arg Ala Arg Pro Lys Ala Gly Arg Thr Ser Ala Ala Arg
            20                  25                  30
```

<210> SEQ ID NO 521
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

```
Pro Ala Thr Ala Gly Lys Arg Lys Arg Ser Asp Ala Ala Trp Ser
 1               5                  10                  15

Lys Arg Ala Arg Pro Lys Ala Gly Arg Thr Ser Ala Ala Arg Pro Gly
            20                  25                  30

Thr Ser Val Arg Arg Ile Arg
        35
```

<210> SEQ ID NO 522
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

```
Ser Ser Ser Leu Gly Lys Arg Lys Arg Ser Asn Gly Gly Asp Trp Ser
 1               5                  10                  15

Lys Arg Ser Ala Lys Lys Lys Pro Ala
            20                  25
```

<210> SEQ ID NO 523
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

```
Ser Ser Ser Leu Gly Lys Arg Lys Arg Ser Asn Gly Gly Asp Trp Ser
 1               5                  10                  15

Lys Arg Ser Ala Lys Lys Lys Pro Ala Gly Thr Pro Ser Arg Arg Ala
            20                  25                  30
```

```
Gly Pro Gly Arg Gly Pro Arg
        35

<210> SEQ ID NO 524
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Ser Ser Ser Leu Gly Lys Arg Lys Arg Ser Asp Glu Gly Ala Trp Ser
1               5                   10                  15

Lys Gly Lys Ser Lys Lys Lys Ala Met Arg
            20                  25

<210> SEQ ID NO 525
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Ser Ser Ser Leu Gly Lys Arg Lys Arg Ser Asp Glu Gly Ala Trp Ser
1               5                   10                  15

Lys Gly Lys Ser Lys Lys Lys Ala Met Arg Gly Ser Ser Ser Arg Arg
            20                  25                  30

Pro Gly Pro Val Arg Gly Pro
        35

<210> SEQ ID NO 526
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Ser Thr Ser Lys Arg Lys Arg Gly Asp Asp Ala Asn Trp Asn Lys Arg
1               5                   10                  15

Pro Thr Lys Lys Lys Pro Ser Ser
            20

<210> SEQ ID NO 527
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 527

Ser Thr Ser Lys Arg Lys Arg Gly Asp Asp Ala Asn Trp Asn Lys Arg
1               5                   10                  15

Pro Thr Lys Lys Lys Pro Ser Ser Ala Gly Leu Lys Lys Ala Gly Ser
            20                  25                  30

Lys Ala Glu Arg Pro Ser Leu
        35
```

```
<210> SEQ ID NO 528
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Ser Gly Ala Leu Lys Arg Lys Arg Ser Asp Glu Val Ala Trp Ser Arg
1               5                   10                  15

Arg Arg Pro Val Lys Lys Pro Val
            20

<210> SEQ ID NO 529
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Ser Gly Ala Leu Lys Arg Lys Arg Ser Asp Glu Val Ala Trp Ser Arg
1               5                   10                  15

Arg Arg Pro Val Lys Lys Pro Val Arg Arg Ala Pro Pro Pro Arg Ala
            20                  25                  30

Gly Pro Ser Val Arg Arg Gly
        35

<210> SEQ ID NO 530
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Ser Gly Ala Leu Lys Arg Lys Arg Ser Asp Glu Val Ala Trp Ser Arg
1               5                   10                  15

Arg Lys Pro Ala Lys Lys Pro Ala Arg
            20                  25

<210> SEQ ID NO 531
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Ser Gly Ala Leu Lys Arg Lys Arg Ser Asp Glu Val Ala Trp Ser Arg
1               5                   10                  15

Arg Lys Pro Ala Lys Lys Pro Ala Arg Gln Pro Pro Pro Arg Ala
            20                  25                  30

Gly Pro Ser Val Arg Arg Gly
        35

<210> SEQ ID NO 532
<211> LENGTH: 25
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 532

Ala Gly Ala Leu Lys Arg Lys Arg Ser Asp Glu Val Ala Trp Ser Arg
1               5                   10                  15

Arg Lys Pro Ala Lys Lys Pro Ala Arg
            20                  25

<210> SEQ ID NO 533
<211> LENGTH: 39
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 533

Ala Gly Ala Leu Lys Arg Lys Arg Ser Asp Glu Val Ala Trp Ser Arg
1               5                   10                  15

Arg Lys Pro Ala Lys Lys Pro Ala Arg Ala Pro Pro Arg Ala Gly
            20                  25                  30

Pro Ser Val Arg Arg Gly Leu
        35

<210> SEQ ID NO 534
<211> LENGTH: 243
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 534

Ser Thr Ser Lys Arg Lys Arg Gly Asp Asp Ser Asn Trp Ser Lys Arg
1               5                   10                  15

Val Thr Lys Lys Lys Pro Ser Ser Ala Gly Leu Lys Arg Ala Gly Ser
            20                  25                  30

Lys Ala Asp Arg Pro Ser Leu Gln Ile Gln Thr Leu Gln His Ala Gly
        35                  40                  45

Thr Thr Met Ile Thr Val Pro Ser Gly Gly Val Cys Asp Leu Ile Asn
    50                  55                  60

Thr Tyr Ala Arg Gly Ser Asp Glu Gly Asn Arg His Thr Ser Glu Thr
65                  70                  75                  80

Leu Thr Tyr Lys Ile Ala Ile Asp Tyr His Phe Val Ala Asp Ala Ala
                85                  90                  95

Ala Cys Arg Tyr Ser Asn Thr Gly Thr Gly Val Met Trp Leu Val Tyr
            100                 105                 110

Asp Thr Thr Pro Gly Gly Gln Ala Pro Thr Pro Gln Thr Ile Phe Ser
        115                 120                 125

Tyr Pro Asp Thr Leu Lys Ala Trp Pro Ala Thr Trp Lys Val Ser Arg
    130                 135                 140

Glu Leu Cys His Arg Phe Val Val Lys Arg Arg Trp Leu Phe Asn Met
145                 150                 155                 160

Glu Thr Asp Gly Arg Ile Gly Ser Asp Ile Pro Pro Ser Asn Ala Ser
                165                 170                 175

Trp Lys Pro Cys Lys Arg Asn Ile Tyr Phe His Lys Phe Thr Ser Gly
            180                 185                 190

Leu Gly Val Arg Thr Gln Trp Lys Asn Val Thr Asp Gly Gly Val Gly

```
                195                 200                 205

Ala Ile Gln Arg Gly Ala Leu Tyr Met Val Ile Ala Pro Gly Asn Gly
    210                 215                 220

Leu Thr Phe Thr Ala His Gly Gln Thr Arg Leu Tyr Phe Lys Ser Val
225                 230                 235                 240

Gly Asn Gln

<210> SEQ ID NO 535
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 535

Asp Pro Gln Asn Ala Leu Tyr Tyr Gln Pro Arg Val Pro Thr Ala Ala
1               5                   10                  15

Pro Thr Ser Gly Gly Val Pro Trp Ser Arg Val Gly Glu Val Ala Ile
            20                  25                  30

Leu Ser Phe Val Ala Leu Ile Cys Phe Tyr Leu Leu Tyr Leu Trp Val
        35                  40                  45

Leu Arg Asp Leu Ile Leu Val Leu Lys Ala Arg Gln Gly Arg Ser Thr
    50                  55                  60

Glu Glu Leu Ile Phe Gly Gly Gln Ala Val Asp Arg Ser Asn Pro Ile
65                  70                  75                  80

Pro Asn Ile Pro Ala Pro Pro Ser Gln Gly Asn Pro Gly Pro Phe Val
                85                  90                  95

Pro Gly Thr Gly
            100

<210> SEQ ID NO 536
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 536

Gly Ser Gln Leu Val Pro Pro Ser Ala Phe Asn Tyr Ile Glu Ser
1               5                   10                  15

Gln Arg Asp Glu Phe Gln Leu Ser His Asp Leu Thr Glu Ile Val Leu
            20                  25                  30

Gln Phe Pro Ser Thr Ala Ser Gln Ile Thr Ala Arg Leu Ser Arg Ser
        35                  40                  45

Cys Met Lys Ile Asp His Cys Val Ile Glu Tyr Arg Gln Gln Val Pro
    50                  55                  60

Ile Asn Ala Ser Gly Thr Val Ile Val Glu Ile His Asp Lys Arg Met
65                  70                  75                  80

Thr Asp Asn Glu Ser Leu Gln Ala Ser Trp Thr Phe Pro Ile Arg Cys
                85                  90                  95

Asn Ile Asp Leu His Tyr Phe Ser Ser Phe Phe Ser Leu Lys Asp
            100                 105                 110

Pro Ile Pro Trp Lys Leu Tyr Tyr Arg Val Ser Asp Ser Asn Val His
        115                 120                 125

Gln Met Thr His Phe Ala Lys Phe Lys Gly Lys Leu Lys Leu Ser Ser
    130                 135                 140
```

```
Ala Lys His Ser Val Asp Ile Pro Phe Arg Ala Pro Thr Val Lys Ile
145                 150                 155                 160

Leu Ala Lys Gln Phe Ser Glu Lys Asp Ile Asp Phe Trp His Val Gly
            165                 170                 175

Tyr Gly Lys Trp Glu Arg Arg Leu Val Lys Ser Ala Ser Ser Ser Arg
        180                 185                 190

Phe Gly Leu Arg Gly Pro Ile Glu Ile Asn Pro Gly Glu Ser Trp Ala
    195                 200                 205

Thr Lys Ser Ala Ile Val Thr Pro Asn Arg Asn Ala Asp Leu Asp Ile
210                 215                 220

Glu Glu Glu Leu Leu Pro Tyr Arg Glu Leu Asn Arg Leu Gly Thr Asn
225                 230                 235                 240

Ile Leu Asp Pro Gly Glu Ser Ala Ser Ile Val Gly Ile Gln Arg Ser
                245                 250                 255

Gln Ser Asn Ile Thr Met Ser Met Ser Gln Leu Asn Glu Leu Val Arg
            260                 265                 270

Ser Thr Val His Glu Cys Ile Lys Thr Ser Cys Ile Pro Ser Thr Pro
        275                 280                 285

Lys Ser Leu Ser
    290

<210> SEQ ID NO 537
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Arg Thr Gly Val Lys Arg Ser Tyr Gly Ala Ala Arg Gly Asp Asp Arg
1               5                   10                  15

Arg Arg Pro Asn Val Val
            20

<210> SEQ ID NO 538
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Ser Tyr Val Lys Thr Val Pro Asn Arg Thr Arg Thr Tyr Ile Lys Leu
1               5                   10                  15

Arg Val Arg

<210> SEQ ID NO 539
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Met Tyr Ser Thr Ser Asn Arg Arg Gly Arg Ser Gln Thr Gln Arg Gly
1               5                   10                  15

Ser His Val Arg Arg Thr Gly Val Lys Arg Ser Tyr Gly Ala Ala Arg
```

```
                    20                  25                  30
Gly Asp Asp Arg Arg Pro Asn Val Val Ser Lys Thr Gln Val Glu
            35                  40                  45
Pro Arg Met Thr Ile Gln Arg Val Gln Glu Asn Gln Phe Gly Pro Glu
 50                  55                  60
Phe Val Leu Ser Gln Asn Ser Ala Leu Ser Thr Phe Val Thr Tyr Pro
 65                  70                  75                  80
Ser Tyr Val Lys Thr Val Pro Asn Arg Thr Arg Thr Tyr Ile Lys Leu
                 85                  90                  95
Lys Arg Val Arg Phe Lys Gly Thr Leu Lys Ile Glu Arg Gly Gln Gly
                100                 105                 110
Asp Thr Ile Met Asp Gly Pro Ser Ser Asn Ile Glu Gly Val Phe Ser
                115                 120                 125
Met Val Ile Val Val Asp Arg Lys Pro His Val Ser Gln Ser Gly Arg
            130                 135                 140
Leu His Thr Phe Asp Glu Leu Phe Gly Ala Arg Ile His Cys His Gly
145                 150                 155                 160
Asn Leu Ser Val Val Pro Ala Leu Lys Asp Arg Tyr Tyr Ile Arg His
                165                 170                 175
Val Thr Lys Arg Val Ser Leu Glu Lys Asp Thr Leu Leu Ile Asp
            180                 185                 190
Leu His Gly Thr Thr Gln Leu Ser Asn Lys Arg Tyr Asn Cys Trp Ala
            195                 200                 205
Ser Phe Ser Asp Leu Glu Arg Asp Cys Asn Gly Val Tyr Gly Asn Ile
        210                 215                 220
Thr Lys Asn Ala Leu Leu Val Tyr Tyr Cys Trp Leu Ser Asp Ala Gln
225                 230                 235                 240
Ser Lys Ala Ser Thr Tyr Val Ser Phe Glu Leu Asp Tyr Leu Gly
                245                 250                 255

<210> SEQ ID NO 540
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 540

Arg Arg Arg Arg Arg Arg Arg Arg Arg Arg Val Asp Tyr Gly
 1               5                  10                  15
Lys Trp Glu Arg Lys Pro Ile Arg Cys Ala Ser Met Ser Arg
                20                  25                  30

<210> SEQ ID NO 541
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Arg Arg Arg Arg Arg Arg Arg Arg Arg Arg Gly Lys Trp Glu
 1               5                  10                  15

Arg Lys Pro Ile Arg Cys Ala Ser
                20
```

```
<210> SEQ ID NO 542
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Lys Lys Lys Lys Lys Lys Lys Lys Lys Lys Lys Lys Lys Lys Lys Lys
1               5                   10                  15

Gly Lys Trp Glu Arg Lys Pro Ile Arg Cys Ala Ser
            20                  25

<210> SEQ ID NO 543
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543

Arg Arg Arg Arg Arg Arg Arg Arg Arg Arg Arg Val Asp Phe Ser
1               5                   10                  15

His Val Asp Tyr Gly Lys Trp Glu Arg Lys Pro Ile Arg Cys Ala Ser
            20                  25                  30

Met Ser Arg Leu Gly Leu Arg Gly
            35                  40

<210> SEQ ID NO 544
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Gly Val Lys Arg Ser Tyr Gly Ala Ala Arg Gly Asp Asp Arg Arg
1               5                   10                  15

Pro Asn Val Val Ala Pro Tyr Lys Ala Trp Arg Arg Arg Arg Arg
            20                  25                  30

Arg Arg Arg Arg Arg Arg
            35

<210> SEQ ID NO 545
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 545

Lys Ser Val Pro Asn Arg Thr Arg Thr Tyr Ile Lys Leu Lys Arg Leu
1               5                   10                  15

Arg Phe Lys Gly Ala Pro Tyr Lys Ala Trp Arg Arg Arg Arg Arg Arg
            20                  25                  30

Arg Arg Arg Arg Arg Arg
            35

<210> SEQ ID NO 546
<211> LENGTH: 34
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 546

Arg Thr Gly Val Lys Arg Ser Tyr Gly Ala Ala Arg Gly Asp Asp Arg
1               5                   10                  15

Arg Arg Pro Asn Val Val Arg Arg Arg Arg Arg Arg Arg Arg
            20                  25                  30

Arg Arg

<210> SEQ ID NO 547
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Ser Tyr Val Lys Thr Val Pro Asn Arg Thr Arg Thr Tyr Ile Lys Gly
1               5                   10                  15

Gly Gly Gly Gly Arg Arg Arg Arg Arg Arg Arg Arg Arg Arg Arg Arg
            20                  25                  30

<210> SEQ ID NO 548
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Val Asp Ile Pro Phe Arg Ala Pro Thr Ile Lys Ile Leu Ser Lys Gln
1               5                   10                  15

Phe Thr Glu Asp Asp Ile Asp Phe Trp His Val Gly Tyr Gly Lys Trp
            20                  25                  30

Glu Arg Lys Leu Val Arg Pro Ala Ser Leu Ser Gly Arg Arg Gly Leu
        35                  40                  45

Arg Arg
    50

<210> SEQ ID NO 549
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Ile Asp Phe Trp His Val Gly Tyr Gly Lys Trp Glu Arg Lys Leu Val
1               5                   10                  15

Arg Pro Ala Ser Leu Ser Gly Arg Arg Gly Leu Arg Arg
            20                  25

<210> SEQ ID NO 550
<211> LENGTH: 31
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 550

Ile Asp Phe Trp Ser Val Glu Lys Gly Glu Thr Arg Arg Leu Leu
1               5                   10                  15

Asn Pro Thr Pro His Ala His Ser Pro Arg Pro Ile Ala His Arg
            20                  25                  30

<210> SEQ ID NO 551
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Ile Asp Phe Ser His Val Gly Tyr Gly Lys Trp Glu Arg Lys Met Ile
1               5                   10                  15

Arg Ser Ala Ser Ile Ser Arg Leu Gly Leu His Asn
            20                  25

<210> SEQ ID NO 552
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Val Asp Phe Ser His Val Gly Tyr Gly Lys Trp Glu Arg Lys Leu Ile
1               5                   10                  15

Arg Ser Ala Ser Thr Val Lys Tyr Gly Leu Pro Ser
            20                  25

<210> SEQ ID NO 553
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Ile Asp Phe Ser His Val Asp Tyr Gly Lys Val Glu Arg Lys Leu Val
1               5                   10                  15

Lys Cys Glu Ser Ser Ser Arg Leu Gly Leu His Ser
            20                  25

<210> SEQ ID NO 554
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Ile Asp Phe Trp Ser Val Gly Arg Lys Ala Gln Gln Arg Lys Leu Val
1               5                   10                  15

Gln Gly Pro Ser Leu Ile Gly Ser Arg Ser Met Arg Tyr
            20                  25

<210> SEQ ID NO 555
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 555

Ile Asp Phe Trp Ser Val Gly Ser Lys Pro Gln Thr Arg Arg Leu Val
1               5                   10                  15

Asp Gly Ser Arg Leu Ile Gly His Ser Ser Arg Ser Leu Arg Val
            20                  25                  30

<210> SEQ ID NO 556
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Ile Asp Phe Trp Ser Val Glu Arg Gly Glu Thr Arg Arg Arg Leu Leu
1               5                   10                  15

Asn Pro Thr Pro Ser Ala Gly Ser Asn Arg Ala Leu Ser Lys Arg
            20                  25                  30

<210> SEQ ID NO 557
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Val Asp Phe Trp Ser Val Gly Lys Pro Lys Pro Ile Arg Arg Leu Ile
1               5                   10                  15

Gln Asn Asp Pro Gly Thr Asp Tyr Asp Thr Gly Pro Lys Tyr Arg
            20                  25                  30

<210> SEQ ID NO 558
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Val Asp Phe Trp Ser Val Glu Lys Pro Lys Pro Ile Arg Arg Leu Leu
1               5                   10                  15

Asn Pro Gly Pro Asn Gln Gly Pro Tyr Pro Asn Thr Gly His Arg
            20                  25                  30

<210> SEQ ID NO 559
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Val Asp Phe Ser His Val Asp Tyr Gly Lys Trp Glu Arg Lys Leu Ile
1               5                   10                  15

Arg Ser Ala Ser Thr Ser Arg Tyr Gly Leu Arg Ser
            20                  25

<210> SEQ ID NO 560
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Val Asp Phe Ser His Val Asp Tyr Gly Lys Trp Glu Arg Lys Thr Leu
1               5                   10                  15

Arg Ser Arg Ser Leu Ser Arg Ile Gly Leu Thr Gly
            20                  25

<210> SEQ ID NO 561
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Ile Asp Phe Trp His Val Gly Tyr Gly Lys Trp Glu Arg Arg Leu Val
1               5                   10                  15

Lys Ser Ala Ser Ser Ser Arg Phe Gly Ile Arg Gly
            20                  25

<210> SEQ ID NO 562
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Val Asp Phe Phe His Val Asp Tyr Gly Arg Trp Glu Arg Lys His Ile
1               5                   10                  15

Arg Cys Ala Ser Met Ser Arg Val Gly Leu Arg Gly
            20                  25

<210> SEQ ID NO 563
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Gly Thr Phe Gln His Val Asp Tyr Gly Lys Trp Glu Arg Lys Pro Ile
1               5                   10                  15

Arg Cys Gln Ser Met Ser Arg Val Gly Tyr Arg Arg
            20                  25

<210> SEQ ID NO 564
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 564

Val Gly Tyr Gly Lys Trp Glu Arg Lys Leu Val Arg Pro Ala Ser Leu
1               5                   10                  15

Ser

<210> SEQ ID NO 565
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Val Glu Lys Gly Glu Thr Arg Arg Arg Leu Leu Asn Pro Thr Pro His
1               5                   10                  15

Ala

<210> SEQ ID NO 566
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Val Gly Tyr Gly Lys Trp Glu Arg Lys Leu Ile Arg Ser Ala Ser Thr
1               5                   10                  15

Val

<210> SEQ ID NO 567
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Val Glu Lys Pro Lys Pro Ile Arg Arg Leu Leu Asn Pro Gly Pro Asn
1               5                   10                  15

Gln

<210> SEQ ID NO 568
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Val Asp Tyr Gly Lys Trp Glu Arg Lys Leu Ile Arg Ser Ala Ser Thr
1               5                   10                  15

Ser

<210> SEQ ID NO 569
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 569

Val Asp Tyr Gly Lys Trp Glu Arg Lys Thr Leu Arg Ser Arg Ser Leu
1               5                   10                  15
Ser

<210> SEQ ID NO 570
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Val Gly Tyr Gly Lys Trp Glu Arg Arg Leu Val Lys Ser Ala Ser Ser
1               5                   10                  15
Ser

<210> SEQ ID NO 571
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Val Asp Tyr Gly Arg Trp Glu Arg Lys His Ile Arg Cys Ala Ser Met
1               5                   10                  15
Ser

<210> SEQ ID NO 572
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Val Glu Arg Pro Lys Pro Ile Arg Arg Leu Leu Thr Pro Thr Pro Gly
1               5                   10                  15
Cys

<210> SEQ ID NO 573
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Pro Phe Arg Ala Pro Thr Ile Lys Ile Leu Ser Lys Gln Phe Thr Glu
1               5                   10                  15

Asp Asp Ile Asp Phe Trp His Val Gly Tyr Gly Lys Trp Glu Arg Lys
                20                  25                  30

Leu Val Arg Pro Ala Ser Leu Ser Gly Arg Arg Gly Leu Arg Arg
            35                  40                  45
```

<210> SEQ ID NO 574
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 574

Pro Phe Arg Ala Pro Thr Val Lys Ile Leu Ser Lys Gln Phe Thr Asp
1               5                   10                  15

Lys Asp Ile Asp Phe Ser His Val Gly Tyr Gly Lys Trp Glu Arg Lys
            20                  25                  30

Met Ile Arg Ser Ala Ser Ile Ser Arg Leu Gly Leu
        35                  40

<210> SEQ ID NO 575
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 575

Asp Ile Ala Phe Arg Ala Pro Thr Val Lys Ile Leu Ser Lys Gln Phe
1               5                   10                  15

Thr Asp Arg Asp Val Asp Phe Ser His Val Gly Tyr Gly Lys Trp Glu
            20                  25                  30

Arg Lys Leu Ile Arg Ser Ala Ser Thr Val Lys Tyr Gly Leu
        35                  40                  45

<210> SEQ ID NO 576
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 576

Asp Ile Arg Phe Lys Pro Pro Thr Ile Asn Ile Leu Ser Lys Asp Tyr
1               5                   10                  15

Thr Ala Asp Cys Val Asp Phe Trp Ser Val Glu Lys Pro Lys Pro Ile
            20                  25                  30

Arg Arg Leu Leu Asn Pro Gly Pro Asn Gln Gly Pro Tyr Pro Asn Thr
        35                  40                  45

Gly

<210> SEQ ID NO 577
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 577

Asp Ile Pro Phe Arg Ala Pro Thr Val Lys Ile His Ser Lys Gln Phe
1               5                   10                  15

Ser His Arg Asp Val Asp Phe Ser His Val Asp Tyr Gly Lys Trp Glu
            20                  25                  30

```
Arg Lys Thr Leu Arg Ser Arg Ser Leu Ser Arg Ile Gly Leu
        35                  40                  45
```

<210> SEQ ID NO 578
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 578

```
Asp Ile Pro Phe Arg Ala Pro Thr Val Lys Ile Leu Ala Lys Gln Phe
1               5                   10                  15

Ser Glu Lys Asp Ile Asp Phe Trp His Val Gly Tyr Gly Lys Trp Glu
            20                  25                  30

Arg Arg Leu Val Lys Ser Ala Ser Ser Arg Phe Gly Ile
        35                  40                  45
```

<210> SEQ ID NO 579
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

```
Asp Ile Pro Phe Arg Ala Pro Thr Val Lys Ile Leu Ser Lys Gln Phe
1               5                   10                  15

Thr Asp Lys Asp Val Asp Phe Phe His Val Asp Tyr Gly Arg Trp Glu
            20                  25                  30

Arg Lys His Ile Arg Cys Ala Ser Met Ser Arg Val Gly Leu
        35                  40                  45
```

<210> SEQ ID NO 580
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580

```
Asp Ile Lys Tyr Lys Pro Pro Thr Ile Lys Ile Leu Ser Lys Asp Tyr
1               5                   10                  15

Thr Ala Asp Cys Val Asp Phe Trp Ser Val Glu Arg Pro Lys Pro Ile
            20                  25                  30

Arg Arg Leu Leu Thr Pro Thr Pro Gly Cys Gly
        35                  40
```

<210> SEQ ID NO 581
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 581

```
Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
```

```
                    20                  25                  30

Gly Gly Val Lys Lys Pro His Arg Tyr Arg Pro Gly Thr Val Ala
            35                  40                  45

<210> SEQ ID NO 582
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 582

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile

<210> SEQ ID NO 583
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 8 to 20 residues

<400> SEQUENCE: 583

Lys Lys Lys Lys Lys Lys Lys Lys Lys Lys Lys Lys Lys Lys Lys Lys
1               5                   10                  15

Lys Lys Lys Lys
            20

<210> SEQ ID NO 584
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 8 to 20 residues

<400> SEQUENCE: 584

Arg Arg Arg Arg Arg Arg Arg Arg Arg Arg Arg Arg Arg Arg Arg Arg
1               5                   10                  15

Arg Arg Arg Arg
            20

<210> SEQ ID NO 585
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(6)
<223> OTHER INFORMATION: This region may encompass 1-6 residues
<220> FEATURE:
```

```
<221> NAME/KEY: MISC_FEATURE
<222> LOCATION: (7)..(12)
<223> OTHER INFORMATION: This region may encompass 1-6 residues
<220> FEATURE:
<221> NAME/KEY: MISC_FEATURE
<222> LOCATION: (13)..(18)
<223> OTHER INFORMATION: This region may encompass 1-6 residues
<220> FEATURE:
<221> NAME/KEY: MISC_FEATURE
<222> LOCATION: (19)..(24)
<223> OTHER INFORMATION: This region may encompass 1-6 residues
<220> FEATURE:
<221> NAME/KEY: MISC_FEATURE
<222> LOCATION: (25)..(30)
<223> OTHER INFORMATION: This region may encompass 1-6 residues
<220> FEATURE:
<221> NAME/KEY: MISC_FEATURE
<222> LOCATION: (31)..(36)
<223> OTHER INFORMATION: This region may encompass 1-6 residues
<220> FEATURE:
<221> NAME/KEY: MISC_FEATURE
<222> LOCATION: (37)..(42)
<223> OTHER INFORMATION: This region may encompass 1-6 residues
<220> FEATURE:
<221> NAME/KEY: MISC_FEATURE
<222> LOCATION: (43)..(48)
<223> OTHER INFORMATION: This region may encompass 1-6 residues
<220> FEATURE:
<221> NAME/KEY: MISC_FEATURE
<222> LOCATION: (49)..(54)
<223> OTHER INFORMATION: This region may encompass 1-6 residues
<220> FEATURE:
<221> NAME/KEY: MISC_FEATURE
<222> LOCATION: (55)..(60)
<223> OTHER INFORMATION: This region may encompass 1-6 residues
<220> FEATURE:
<221> NAME/KEY: MISC_FEATURE
<222> LOCATION: (61)..(66)
<223> OTHER INFORMATION: This region may encompass 1-6 residues
<220> FEATURE:
<221> NAME/KEY: MISC_FEATURE
<222> LOCATION: (67)..(72)
<223> OTHER INFORMATION: This region may encompass 1-6 residues
<220> FEATURE:
<221> NAME/KEY: MISC_FEATURE
<222> LOCATION: (73)..(78)
<223> OTHER INFORMATION: This region may encompass 1-6 residues
<220> FEATURE:
<221> NAME/KEY: MISC_FEATURE
<222> LOCATION: (79)..(84)
<223> OTHER INFORMATION: This region may encompass 1-6 residues
<220> FEATURE:
<221> NAME/KEY: MISC_FEATURE
<222> LOCATION: (85)..(90)
<223> OTHER INFORMATION: This region may encompass 1-6 residues
<220> FEATURE:
<221> NAME/KEY: MISC_FEATURE
<222> LOCATION: (91)..(96)
<223> OTHER INFORMATION: This region may encompass 1-6 residues
<220> FEATURE:
<221> NAME/KEY: MISC_FEATURE
<222> LOCATION: (97)..(102)
<223> OTHER INFORMATION: This region may encompass 1-6 residues
<220> FEATURE:
<221> NAME/KEY: MISC_FEATURE
<222> LOCATION: (103)..(108)
<223> OTHER INFORMATION: This region may encompass 1-6 residues
<220> FEATURE:
<221> NAME/KEY: MISC_FEATURE
<222> LOCATION: (109)..(114)
<223> OTHER INFORMATION: This region may encompass 1-6 residues
<220> FEATURE:
<221> NAME/KEY: MISC_FEATURE
<222> LOCATION: (115)..(120)
<223> OTHER INFORMATION: This region may encompass 1-6 residues
<220> FEATURE:
<221> NAME/KEY: MISC_FEATURE
<222> LOCATION: (121)..(126)
<223> OTHER INFORMATION: This region may encompass 1-6 residues
```

```
<220> FEATURE:
<221> NAME/KEY: MISC_FEATURE
<222> LOCATION: (127)..(132)
<223> OTHER INFORMATION: This region may encompass 1-6 residues
<220> FEATURE:
<221> NAME/KEY: MISC_FEATURE
<222> LOCATION: (133)..(138)
<223> OTHER INFORMATION: This region may encompass 1-6 residues
<220> FEATURE:
<221> NAME/KEY: MISC_FEATURE
<222> LOCATION: (139)..(144)
<223> OTHER INFORMATION: This region may encompass 1-6 residues
<220> FEATURE:
<221> NAME/KEY: MISC_FEATURE
<222> LOCATION: (145)..(150)
<223> OTHER INFORMATION: This region may encompass 1-6 residues
<220> FEATURE:
<221> NAME/KEY: MISC_FEATURE
<222> LOCATION: (151)..(156)
<223> OTHER INFORMATION: This region may encompass 1-6 residues
<220> FEATURE:
<221> NAME/KEY: MISC_FEATURE
<222> LOCATION: (157)..(162)
<223> OTHER INFORMATION: This region may encompass 1-6 residues
<220> FEATURE:
<221> NAME/KEY: MISC_FEATURE
<222> LOCATION: (163)..(168)
<223> OTHER INFORMATION: This region may encompass 1-6 residues
<220> FEATURE:
<221> NAME/KEY: MISC_FEATURE
<222> LOCATION: (169)..(174)
<223> OTHER INFORMATION: This region may encompass 1-6 residues
<220> FEATURE:
<221> NAME/KEY: MISC_FEATURE
<222> LOCATION: (175)..(180)
<223> OTHER INFORMATION: This region may encompass 1-6 residues
<220> FEATURE:
<221> NAME/KEY: MISC_FEATURE
<222> LOCATION: (181)..(186)
<223> OTHER INFORMATION: This region may encompass 1-6 residues
<220> FEATURE:
<221> NAME/KEY: MISC_FEATURE
<222> LOCATION: (187)..(192)
<223> OTHER INFORMATION: This region may encompass 1-6 residues
<220> FEATURE:
<221> NAME/KEY: MISC_FEATURE
<222> LOCATION: (193)..(198)
<223> OTHER INFORMATION: This region may encompass 1-6 residues
<220> FEATURE:
<221> NAME/KEY: MISC_FEATURE
<222> LOCATION: (199)..(204)
<223> OTHER INFORMATION: This region may encompass 1-6 residues
<220> FEATURE:
<221> NAME/KEY: MISC_FEATURE
<222> LOCATION: (205)..(210)
<223> OTHER INFORMATION: This region may encompass 1-6 residues
<220> FEATURE:
<221> NAME/KEY: MISC_FEATURE
<222> LOCATION: (211)..(216)
<223> OTHER INFORMATION: This region may encompass 1-6 residues
<220> FEATURE:
<221> NAME/KEY: MISC_FEATURE
<222> LOCATION: (217)..(222)
<223> OTHER INFORMATION: This region may encompass 1-6 residues
<220> FEATURE:
<221> NAME/KEY: MISC_FEATURE
<222> LOCATION: (223)..(228)
<223> OTHER INFORMATION: This region may encompass 1-6 residues
<220> FEATURE:
<221> NAME/KEY: MISC_FEATURE
<222> LOCATION: (229)..(234)
<223> OTHER INFORMATION: This region may encompass 1-6 residues
<220> FEATURE:
<221> NAME/KEY: MISC_FEATURE
<222> LOCATION: (235)..(240)
<223> OTHER INFORMATION: This region may encompass 1-6 residues
<220> FEATURE:
<221> NAME/KEY: MISC_FEATURE
<222> LOCATION: (1)..(240)
```

<223> OTHER INFORMATION: This sequence may encompass 3-20 "(Gly)i(Ser)j"
repeating units wherein i ranges from 1 to 6 and j ranges from 1
to 6 and some positions may be absent
<220> FEATURE:
<223> OTHER INFORMATION: See specification as filed for detailed
description of substitutions and preferred embodiments

<400> SEQUENCE: 585

```
Gly Gly Gly Gly Gly Gly Ser Ser Ser Ser Ser Ser Gly Gly Gly Gly
1               5                   10                  15

Gly Gly Ser Ser Ser Ser Ser Gly Gly Gly Gly Gly Ser Ser
            20                  25                  30

Ser Ser Ser Ser Gly Gly Gly Gly Gly Gly Ser Ser Ser Ser Ser Ser
            35                  40                  45

Gly Gly Gly Gly Gly Gly Ser Ser Ser Ser Ser Ser Gly Gly Gly Gly
        50                  55                  60

Gly Gly Ser Ser Ser Ser Ser Gly Gly Gly Gly Gly Gly Ser Ser
65                  70                  75                  80

Ser Ser Ser Ser Gly Gly Gly Gly Gly Gly Ser Ser Ser Ser Ser Ser
                85                  90                  95

Gly Gly Gly Gly Gly Ser Ser Ser Ser Ser Ser Gly Gly Gly Gly
            100                 105                 110

Gly Gly Ser Ser Ser Ser Ser Gly Gly Gly Gly Gly Gly Ser Ser
        115                 120                 125

Ser Ser Ser Ser Gly Gly Gly Gly Gly Gly Ser Ser Ser Ser Ser Ser
        130                 135                 140

Gly Gly Gly Gly Gly Gly Ser Ser Ser Ser Ser Gly Gly Gly Gly
145                 150                 155                 160

Gly Gly Ser Ser Ser Ser Ser Gly Gly Gly Gly Gly Gly Ser Ser
            165                 170                 175

Ser Ser Ser Ser Gly Gly Gly Gly Gly Gly Ser Ser Ser Ser Ser Ser
            180                 185                 190

Gly Gly Gly Gly Gly Gly Ser Ser Ser Ser Ser Ser Gly Gly Gly Gly
        195                 200                 205

Gly Gly Ser Ser Ser Ser Ser Gly Gly Gly Gly Gly Gly Ser Ser
    210                 215                 220

Ser Ser Ser Ser Gly Gly Gly Gly Gly Gly Ser Ser Ser Ser Ser Ser
225                 230                 235                 240
```

PLANT VIRUS MOVEMENT PROTEINS AND METHODS OF USING THE SAME

RELATED APPLICATIONS

The present application claims priority to the U.S. Provisional Application Ser. No. 62/302,155, filed on Mar. 1, 2016, by Jessee et al., and entitled "PLANT VIRUS MOVEMENT PROTEINS AND METHODS OF USING THE SAME," and U.S. Provisional Application Ser. No. 62/303,278, filed on Mar. 3, 2016, by Jessee et al., and entitled "PLANT VIRUS MOVEMENT PROTEINS AND METHODS OF USING THE SAME." The entire disclosure of both of these applications is hereby incorporated by reference herein in their entirety.

SEQUENCE STATEMENT

The Sequence Listing associated with this application is filed in electronic format via EFS-Web and is hereby incorporated by reference into the specification in its entirety. The name of the text file containing the Sequence Listing is LT01229_SL.txt. The size of the text file is 182 kilobytes, and the text file was created on Mar. 1, 2017.

FIELD OF THE INVENTION

The present invention is in the field of transfection complexes suitable for the delivery of one or more biologically active agents to a cell and methods and kits for using the same.

BACKGROUND OF THE DISCLOSURE

Lipid aggregates such as liposomes or cationic polymers can facilitate introduction of macromolecules, such as DNA, RNA, and proteins, into living cells. Aggregates comprising cationic lipid components can be used to effect delivery of large anionic molecules, such as nucleic acids, into certain types of cells.

The use of cationic lipids has become increasingly popular since their introduction over 25 years ago. Several cationic lipids have been described in the literature and some of these are commercially available. DOTMA (N-[1-(2,3-dioleyloxy)propyl]-N,N,N-trimethylammonium chloride; IUPAC: 1,2-di-O-octadecenyl-3-trimethyl-ammonium propane (chloride salt); CAS Number: 104872-42-6) was the first cationic lipid to be synthesized for the purpose of nucleic acid transfection. DOTMA can be formulated alone or can be combined with DOPE (dioleoylphosphatidylethanolamine) into a liposome, and such liposomes can be used to deliver plasmids into some cells. Other classes of lipids subsequently have been synthesized by various groups. For example, DOGS (5-carboxyspermylglycinedioctadecylamide) was the first polycationic lipid to be prepared and other polycationic lipids have since been prepared. The lipid DOSPA (2,3-dioleyloxy-N-[2(spermine-carboxamido)ethyl]-N,N-dimethyl-1-propanaminium) has been described as an effective delivery agent.

In other examples, cholesterol-based cationic lipids, such as DC-Chol (N,N-dimethyl-N-ethylcarboxamidocholesterol) have been prepared and used for transfection. Also, 1,4-bis(3-N-oleylamino-propyl)piperazine was prepared and combined with histone H1 to generate a delivery reagent that was reported to be less toxic than other reagents. Some examples of commercially available lipids include Lipofectin® (DOTMA:DOPE) (Thermo-Fisher, Carlsbad, Calif.), LipofectAmine™ (DOSPA:DOPE) (Thermo-Fisher), LipofectAmine2000™ (Thermo-Fisher), Lipofectamine 3000 (Therom-Fisher), Fugene®, Transfectam® (DOGS), ViaFect (Promega), DNA-In, GeneIn (MTI-GlobalStem) Effectene®, and DC-Chol. Further examples are PEI polymers and dendrimers such as jetPEI (PolyPlus), and Superfect (Qiagen). None of these reagents can be used universally for all cells. This is perhaps not surprising in light of the variation in composition of the membranes of different types of cells as well as the barriers that can restrict entry of extracellular material into cells. Moreover, the mechanism by which cationic lipids deliver nucleic acids into cells is not clearly understood. The reagents are less efficient than viral delivery methods and are toxic to cells, although the degree of toxicity varies from reagent to reagent.

However, transfection agents, including cationic lipids, anionic lipids, cationic polymers, exosomes, and virasomes, are not universally effective in all cell types. Effectiveness of transfection of different cells depends on the particular transfection agent composition. In general, polycationic lipids are more efficient than monocationic lipids in transfecting eukaryotic cells. In many cases, cationic lipids alone are not effective or are only partially effective for transfection so helper lipids or transfection enhancers can be used in combination with cationic lipids.

Many biological materials are taken up by cells via receptor-mediated endocytosis, in which a surface ligand binds to a cell-surface receptor, leading to clustering of ligand-bound receptors, and formation of coated pits followed by internalization of the ligands into endosomes. Both enveloped viruses, like influenza virus and alphaviruses, and non-enveloped viruses, like Adenovirus, infect cells via endocytotic mechanisms. Enhancement of dendrimer-mediated transfection of some cells by chloroquine (a lysosomotropic agent) suggests that endocytosis is involved in at least some transfections.

Introduction of foreign DNA sequences into eukaryotic cells mediated by viral infection is generally orders of magnitude more efficient than transfection with anionic lipids, cationic lipid, PEI, peptides, or dendrimer transfection agents. Viral infection of all the cells in a culture requires fewer than 10 virus particles per cell. Although the detailed mechanism of fusion is not fully understood and varies among viruses, viral fusion typically involves specific fusogenic agents, such as viral proteins, viral spike glycoproteins and peptides of viral spike glycoproteins. Cell binding and internalization also can be enhanced, accelerated or made selective with peptides that bind cell receptors. For example, the penton-base protein of the Adenovirus coat contains the peptide motif RGD (Arg-Gly-Asp) which mediates virus binding to integrins and viral internalization via receptor-mediated endocytosis.

The efficiency of cationic lipid transfections has been shown to be enhanced by the addition of whole virus particles to the transfection mixture. Certain viral components may also enhance the efficiency of cationic lipid-mediated transfection. For example, it has been suggested that "Lipofectin™"-mediated transfections may be enhanced 3-4-fold by adding influenza virus hemagglutinin peptides to the transfection mixture. Antibodies have been shown to enhance cationic lipid transfections and transferrin-poly lysine or asialoglycoprotein polylysine have been shown to enhance cationic lipid transfection.

Nevertheless, these methods do not work for all cell types, require relatively complex protocols and are inconvenient. It is apparent, therefore, that new and improved methods for introducing macromolecules, and particularly nucleic acids, into cell, are greatly to be desired. In particular, improved methods for introducing nucleic acids into a wider variety of cells, and particularly into primary cells, are greatly to be desired.

SUMMARY OF THE INVENTION

Disclosed herein are transfection complexes comprising at least one cell surface ligand or a plant virus movement protein or peptide fragments; at least one helper lipid component; and a transfection enhancer. Also disclosed are pharmaceutical compositions comprising the disclosed transfection complexes, and a pharmaceutically acceptable carrier. Further, disclosed are methods of transfecting a cell, the method comprising the steps of: obtaining a transfection complex as disclosed; and contacting a cell with the transfection complex.

DETAILED DESCRIPTION OF THE EMBODIMENTS

Definitions and Abbreviations

It is to be understood that the present invention is not limited to particular devices or biological systems, which may, of course, vary. It is also to be understood that, as used in this specification and the appended claims, the singular forms "a", "an", and "the" include singular and plural referents unless the content clearly dictates otherwise. Thus, for example, reference to "a lipid" includes one or more lipids. It is to be yet further understood that any terminology used herein is for the purpose of describing particular embodiments only, and is not intended to be limiting.

Unless stated otherwise, the following terms, definitions, and abbreviations as used herein are intended to have the following meanings:

As used herein, the term "labeled" is intended to mean that a compound has at least one element, isotope, or chemical compound attached to enable the detection of the compound by using a radioactive or heavy isotope label, or an immune label such as an antibody or antigen or a label derived from a colored, luminescent, phosphorescent, or fluorescent dye. Photoaffinity labeling employing, for example, o-, m- and p-azidobenzoyls, substituted with one or more halogen moieties, including, but not limited to 4-azido-2,3,5,6-tetrafluorobenzoic acid, is utilized for the direct elucidation of intermolecular interactions in biological systems.

The terms "subject" and "animal" are synonymous and, as used herein, refer to humans as well as non-human animals, including, for example, mammals (e.g., a rodent, a mouse, a rat, a rabbit, a monkey, a dog, a cat, a primate, or a pig), birds, reptiles, amphibians, and fish.

The term "cell" generally refers to eukaryotic cells of any type and from any source. Types of eukaryotic cells include epithelial, fibroblastic, neuronal, hematopoietic cells and the like from primary cells, tumor cells or immortalized cell lines. Sources of such cells include any animal such as human, canine, mouse, hamster, cat, bovine, porcine, monkey, ape, sheep, fish, insect, fungus, and any plant including crop plants, algae, ornamentals and trees.

"Delivery" is used to denote a process by which a desired compound is transferred to a target cell such that the desired compound is ultimately located inside the target cell or in, or on, the target cell membrane. In many uses of the compounds of the invention, the desired compound is not readily taken up by the target cell and delivery via lipid aggregates or transfection complexes a means for delivering the desired compound to the appropriate cellular compartment within a cell. In certain uses, especially under in vivo conditions, delivery to a specific target cell type is preferable and can be facilitated by transfection complexes comprising surface ligands of the invention.

Drug refers to any therapeutic or prophylactic agent other than food which is used in the prevention, diagnosis, alleviation, treatment, or cure of disease in man or animal.

"Kit" refers to transfection or protein expression kits which include one or more of the compounds of the present invention or mixtures thereof. Such kits may comprise a carrying means being compartmentalized to receive in close confinement one or more container means such as vials, test tubes and the like. Each of such container means comprises components or a mixture of components needed to perform transfection. Such kits may include one or more components selected from nucleic acids (preferably one or more vectors), cells, one or more compounds of the present invention, lipid-aggregate forming compounds, transfection enhancers, biologically active substances, etc.

The term "associated with", when used in the context of molecular interactions, refers to two entities linked by a direct or indirect covalent or non-covalent interaction, such as hydrogen bonding, van der Waals interactions, hydrophobic interactions, magnetic interactions, electrostatic interactions, etc.

The term "biocompatible," as used herein refers to compounds that are not toxic to cells. Compounds are biocompatible if their addition to cells in vitro results in less than or equal to 20% cell death, and their administration in vivo does not induce inflammation or other such adverse effects.

The term "biodegradable," as used herein, refers to compounds that, when introduced into cells, are broken down into components that the cells can either reuse or dispose of without significant toxic effect on the cells (i.e., fewer than about 20% of the cells are killed when the components are added to cells in vitro). The components do not induce inflammation or other adverse effects in vivo. The chemical reactions relied upon to break down the biodegradable compounds are typically uncatalyzed. The term "effective amount," as used herein with respect to an active agent, refers to the amount necessary to elicit the desired biological response. The effective amount of an agent or device may vary depending on such factors as the desired biological endpoint, the agent to be delivered, the composition of the encapsulating matrix, the target tissue, etc. Delivery of an "effective amount of a molecule" is the delivery of the molecule into a cell in sufficient amounts so that the molecule elicits a biological response, for example, modulating the expression of one or more genes in the cell. In specific embodiments, an effective amount of a molecule is delivered to a cell such that an amelioration or improvement in a disease, condition, or disorder related to the cell can be obtained. Delivery of an "effective amount of siRNA" or an "effective amount or RNAi" is the delivery of siRNA or other RNAi into a cell in sufficient amounts to cause a reduction in expression of the target gene in the cell.

The terms "biologically active agent", "bioactive agents" or the like, generally refers to a composition, complex, compound or molecule which has a biological effect or that modifies, causes, promotes, enhances, blocks or reduces a biological effect, or that enhances or limits the production or activity of, reacts with and/or binds to a second molecules which has a biological effect. The second molecule can, but need not be, an endogenous molecule (e.g., a molecule, such as a protein or nucleic acid, normally present in the target cell). A biological effect may be, but is not limited to, one that stimulates or causes an immunoreactive response; one that impacts a biological process in a cell, tissue or organism (e.g., in an animal); one that imparts a biological process in a pathogen or parasite; one that generates or causes to generate a detectable signal; one that regulates the expression of a protein or polypeptide; one that stops or inhibits the expression of a protein or polypeptide; or one that causes or enhances the expression of a protein or polypeptide. Biologically active compositions, complexes, compounds or molecules may be used in investigative, therapeutic, prophylactic and diagnostic methods and compositions. Bioactive agents may include but are not limited to, pharmaceuticals, cell metabolites, proteins, nutrients (vitamins, amino acids, lipids, nucleotides, and carbohydrates), and exosomes.

The term "cationic lipid" refers to any cationic lipids which may be used for transfection and which under physiological conditions possess at least one positive charge. While it is to be understood that certain of the cell surface ligands that form the basis of the present disclosure can be formulated with cationic lipids the cationic lipids can be considered helper lipids.

The term "lysosomotropic agent" is any compound or molecule which inhibit lysosomal function that prevents or slows the acidification of the lysosomal compartment.

The term "nucleic acid binding moiety" as used herein refers to a compound or molecule capable binding to nucleic acid. In some embodiments, the binding molecule is capable of noncovalently binding to nucleic acid, while in other embodiments, the binding molecule links covalently to a cell binding adhesion sequence, a plant virus movement protein or peptide fragments, a nuclear localization sequence, transfection enhancer, and/or a fusion agent. The binding molecule can include but is not limited to spermine, spermine derivative, spermidine, histones or fragments thereof, protamines or fragments thereof, HMG proteins or fragments thereof, poly-lysine, poly-arginine, poly-histidine, polyamines and cationic peptides, nucleic acid intercalaters, protein nucleic acid sequences or aptamers. In addition, this includes but is not limited to analogs or derivatives of the above compounds. Non limiting examples are the cationic peptides that are repeats of lysine or arginine, for example a sequence having between 8-20 lysine residues (K8-K20) (SEQ ID NO:583) or between 8-20 arginine residues (R8-R20) (SEQ ID NO:584).

"Target cell" or "target tissue" refers to any cell or tissue to which a desired compound is delivered, using a lipid aggregate or transfection complex as carrier for the desired compound.

Transfection is used herein to mean the delivery of any nucleic acid, protein, peptide, lipid, cell nutrient, pharmaceutical agent, molecule or other macromolecule to a target cell or tissue in vitro or in vivo (i.e., in an animal, a plant or a human), such that the nucleic acid, protein or other macromolecule is expressed in, confers a phenotype to, causes enhanced growth, expression of a protein, or has a biological function in the cell.

The term "expressible nucleic acid" includes both DNA and RNA without regard to molecular weight, and the term "expression" means any manifestation of the functional presence of the nucleic acid within the cell including, without limitation, both transient expression and stable expression.

The term "fusion agent" as used herein refers to any chemical or molecules capable breaking down an endosomal membrane or cell membrane and freeing the transfection agent into the cytoplasm of the cell. This term includes but is not limited to viruses, synthetic compounds, proteins, fusion peptides, cell penetration peptides or proteins, or derivatives thereof. As a result of the presence of the fusion agent the membrane can undergo lysis, fusion, or rearrangement or all three.

The term "fusion peptide" refers to any peptide grouping which penetrates a membrane such that the structural organization and integrity of the membrane is lost. Fusion peptides are fusion agents.

The term "transfection agent" as used herein generally refers to composition capable of delivering molecules to cells. Transfection agents can be organic such as lipid, carbohydrate, cationic polymers, dendrimers, peptide or protein based or combination of those depending cell type or tissue that one targets. Transfection agents can also be in-organic such as calcium salts. They included cationic lipids, anionic lipids, cationic peptides, cationic proteins, polycationic virus hybrids, cationic polymers, exosomes, and combinations of the above. Transfection agent as used herein may optionally include at least one or more of the transfection compounds optionally in combination with one or more helper lipids, one or more pegylated lipids, one or more lipids from exosomes, complete lipid mixtures form exosomes, optionally one or more targeting moieties, optionally one or more cell surface ligands, optionally one or more nuclear localization sequences, optionally one or more fusion agents, optionally one or more condensing agents, optionally one or more cell penetration agents, optionally one or more plant movement proteins or peptide fragments, optionally one or more exosomes and optionally one or more lysosomotropic agents.

The term "transfection enhancer" as used herein refers to a compound when added to a transfection agent increases the efficiency of transfection (i.e., increases the percent of cells transfected), increases the level of expression of a transfection agent, or reduces the requirement for the amount of nucleic acid or protein required to give a biological response, or any combination of the enhancements above. In some embodiments, the transfection enhancer also helps deliver molecules that help downregulate expression such as siRNA, LNA's and the like.

The term "surface ligand" or "cell surface ligand" refers to a chemical or structure which will bind to a surface receptor of a cell. The term "cell surface receptor" as used herein refers to any specific chemical grouping on the surface of a cell to which the surface ligand can attach, contact or associate with. A surface ligand is a targeting moiety. Furthermore, surface ligands include anything which is capable of binding to the cell and centering the cell through cytosis (e.g., endocytosis, potocytosis, and pinocytosis).

The term "transfection complex", as used herein generally refers to a composition formulated for the delivery of a biologically active agent, such as a nucleic acid, a protein, a macromolecule, cell nutrient, bioactive molecule or the like, to a cell or to a tissue in vivo or in vitro. Transfection complexes as used herein may include at least one or more of the transfection compounds or agents in combination with the biologically active compound to be delivered, optionally in combination with; one or more helper lipids, one or more pegylated lipids, one or more targeting moieties, one or more nuclear localization sequences, one or more fusion agents, one or more condensing agents, one or more cell penetration agents, one or one or more plant movement proteins or peptide fragments, complete exosomes, total lipid extracts isolated from exosomes, one or more exosome lipids, one more exosome protein components and one or more lysosomotropic agents in addition to the bioactive agent that is to be delivered. For the purposes described herein, the term "transfection complex" may be thought of as a lipoplex or a lipid aggregate contacted with a bioactive agent. Thus, in some instances in the following disclosure, terms such as lipoplex, lipid aggregate and the like may be used to make reference a transfection complex that lacks the one or more bioactive agents or "payloads".

The term "helper lipid", as used herein, generally refers to a lipid that is suitable for use in the preparation and formation of transfection complexes disclosed herein. Suitable helper lipids may include, though are not limited to DOPE, DPhPE, saturated and unsaturated DPPE, saturated and unsaturated DMPE, DOPC, Lyso-PE (1-acyl-2-hydroxy-sn-glycero-3-phosphoethanolamine), Lyso-PC (1-acyl-3-hydroxy-sn-glycero-3-phosphocholine), 3-alkyloxy-2-hydroxy-1-acetamidopropane, 4-alkyloxy-3-hydroxy-1-acetamidopropane, 5-alkyloxy-4-hydroxy-1-acetamidopropane, cholesterols, cholesterol derivatives, sterols, including phytosterols, zoosterols and hopanoids, or any of the neutral or cationic lipids that are known to allow or to facilitate the introduction of exogenous bioactive molecules to the interior of a cell or of a tissue. In some embodiments, more than one helper lipid may be used in the formulation of the transfection complexes described herein. Exemplary though non-limiting neutral or cationic lipids contemplated for use in the preparation of the presently disclosed transfection complexes may include one or more lipids selected from the following: N-(2-bromoethyl)-N,N-dimethyl-2,3-bis(9-octadecenyloxy)-propanaminimunbromide (BMOP), dipalmitoylphosphatidylethanolamine 5-carboxyspermylamide (DDPES), DSPC, dioleoylphosphatidylethanolamine (DOPE), formulation of cetyltrimethylammonium bromide (CATB) and DOPE (CTAB:DOPE), 1-palmitoyl-2-oleoyl-sn-glycero-3-phosphocholine (POPC), DMG, 1,2-dimyristloxyaminopropane (DMAP), dimyristoylphospatidylethanolamine (DMPE), DOMG, DMA, Dioleoylphosphatidylcholine (DOPC), dimyristoylphosphatidylcholine (DMPC), Dipalmitoylethylphosphatidylcholine (DPEPC), dioleoydimethylammonium chloride (DODAC), 1,3-di-oleoyloxy-2-(6-carboxyspermyl)-propylamid (DOSPER), N-[1-(2,3-dioleyloxy)propyl]-N,N,N-trimethyl-ammoniumchloride (DOTMA), N-[1-(2,3-dipalmitoeyloxy)propyl]-N,N,N-trimethylammoniumchloride (DPTMA), didoceyl methylammonium bromide (DDAB), N-[1-(2,3-dioleoyloxy)propyl]-N,N,N-trimethyl-ammonium methylsulfate (DOTAP), DOTAP.Cl, 3,β-N,(N',N'-dimethylaminoethane)-carbamoyl]cholesterol (DC-chol), 2-(sperminecarboxamido)ethyl)-N,N-dimethyl-lammonium trifluoroacetate (DOSPA), O,O'-ditetradecanoyl-N-(alphatrimethylammonioacetyl) diethanolamine chloride (DC-6-14), dicaproylphosphtidylethanolamine (DCPE), dilauryl oxypropyl-3-dimethylhydroxy ethylammonium bromide (DLRIE), 1,2-dioleoyl-3-dimethylammonium-propane (DODAP), Ethyl-PC, 2,3-dioleoyloxy-N-[2-(sperminecarboxamidoethyl]-N,N-di-met-hyl-1-propanaminium trifluoroacetate (DOSPA), dioctadecylamidoglycyl carboxyspermine (DOGS), N-[1-(2,3dimyristyloxy)propyl]-N,N-dimethyl-N-(2-hydroxyethyl) ammonium bromide (DMRIE), Dioleoylethyl-phosphocholine (DOEPC), N-[1-(2,3-dioleoyloxy)propyl]-N-[1-(2-hydroxyethyl)]-N,Ndimethylammonium iodide (DOHME), N-(3-aminopropyl)-N,N-dimethyl-2,3-bis(dodecyloxy)-1-propaniminium bromide/dioleylphosphatidylethanolamine (GAP-DLRIE: DOPE), dipalmitoylphospha-tidylcholine (DPPC), 1,2-dioleoyl-sn-glycero-3-[phospho-rac-(3-lysyl(1-glycerol)).Cl (DOPG), N-lauroylsarcosine, (R)-(+)-limonene, lecithins (and derivatives thereof); phosphotidylethanolamine (and derivatives thereof); phosphatidylethanolamines, dioleoyl-phosphatidylethanolamine), diphytanoylphosphatidylethanolamine (DPhPE), dipalmitoylphosphatidylethanolamine (DPPE), dipalmiteoylphosphatidylethanolamine, 3-β-[1-ornithinamidecarbamoyl]-cholesterol (0-Chol), palmitoyloleoylphosphatidyl-ethanolamine (POPE); distearoylphosphatidylethanolamine; phosphotidylcholine; phosphatidylcholines, dipalmitoylphosphatidylcholine (DPPC) palmitoyloleoyl-phosphatidylcholine (POPC); distearoylphosphatidylcholine; phosphatidylglycerol; piperazine-based cationic lipids, a phosphatidylglycerol, dioleoyl-phosphatidylglycerol (DOPG), dipalmitoylphosphatidyl-glycerol (DPPG), distearoylphosphatidylglycerol; phosphatidylserine (and derivatives thereof); phosphatidylserines, dioleoyl- or dipalmitoylphosphatidylserine; a diquaternary ammonium salt; N,N'-dioleyl-N,N,N',N'-tetramethyl-1,2-ethanediamine (TmedEce), N,N'-dioleyl-N,N,N',N'-tetramethyl-1,3-propanediamine (PropEce), N,N'-dioleyl-N,N,N',N'-tetramethyl-1,6-hexanediamine (HexEce), and their corresponding N,N'-dicetyl saturated analogues (TmedEce, PropEce and HexEce), a diphosphatidylglycerol; a fatty acid ester; a monocationic transfection lipid; 1-deoxy-1-[dihexadecyl(methyl)ammonio]-D-xylitol; 1-deoxy-1-[methyl(ditetra-decyl)ammonio]-Darabinitol; 1-deoxy-1-[dihexadecyl(methyl)ammonio]-D-arabinitol; a 1-deoxy-1-[methyl(dioctadecyl)-ammonio]-darabinitol, glycerol ester; sphingolipids; cardolipin; a cerebroside; a ceramide, exosomes or lipids mixtures isolated from exosomes; and combinations thereof.

Helper lipids also include the neutral lipids cholesterol and other 3(30H-sterols, as well as derivatives thereof, phosphatidyl choline, or commercially available cationic lipid mixtures such as, for example, LIPOFECTIN® CELLFECTIN® (1:1.5 (M/M) formulation of N,N,N',N'',N'''-tetramethyl-N,N,N',N'',N'''-tetrapalmitylspermine (TMTPS) and dioleoyl phosphatidylethanolamine (DOPE), LIPOFECTACE®, GS 2888 CYTOFECTIN®, FUGENE 6®, EFFECTENE®, and LIPOFECTAMINE®, LIPOFECTAMINE 2000®, LIPOFECTAMINE PLUS®, LIPOTAXI®, POLYECT®, SUPERFECT®, TFXNT™, TRANSFAST™, TRANSFECTAM®, TRANSMESSENGER®, vectamidine (3-tetradecylamino-N-tert-butyl-N'-tetradecylpropionamidine (a.k.a. diC14-amidine), OLIGOFECTAMINE MessengerMAX, GeneIn™, TransfeX™, LipofectAmine 3000, Lipofectin®, DMRIE-C, CellFectin®, LipofectAce®, Fugene®, Fugene® HD, Tfx-100, Tfx-20®, Tfx-50®, DNA-In, Transfectin™, SilentFect™, Effectene®, ViaFect™, DC-chol, GenePorter®, DharmaFect 1®, DharmaFect 2®, DharmaFect 3®, DharmaFect 4®, Escort™ III, Escort™ IV, DOGS among others. Also contemplated are any mixtures of combination of the above listed helper lipids, exosomes, and lipids mixtures isolated from exosomes.

Examples of lipids examples isolated from exosomes are include, but are not limited to, Lyso-PC (non-limiting examples include C-18, C-16, C-14 and mixture), lyso-bisphosphatidic acid (non-limiting example include C-18, C-16 and C-14), sphingomyelin, ceramides (non-limiting examples include C-8 and C-24), disaturated PC (non-limiting examples include DSPC, DPPC, DMPC, and compounds having a Cn length (where n=8-25), diunsaturated PC-MIX (non-limiting examples include DOPC and DP(db) PC), phosphatidyl serine (PS), phosphatidyl inositol (PI), disaturated PE (non-limiting example include DSPE, DPPE, and DMPE), di-unsaturated PE-MIX (non-limiting example include DOPE and DP(db)PE), phosphatidyl glycerol (PG), (non-limiting examples include C-18C-22), cholesterol, and diglycerides, such as cardiolipin.

Also contemplated are any mixtures of combination of the above listed helper lipids, exosomes, and lipids mixtures isolated from exosomes.

The following patent documents, patent applications, or references are incorporated by reference herein in their entirety and in particular for their disclosure of transfection agents containing cationic and neutral helper lipids, which may be used in the transfection complexes disclosed herein: U.S. Pat. Nos. 6,075,012; 6,020,202; 5,578,475; 5,736,392; 6,051,429; 6,376,248; 5,334,761; 5,316,948; 5,674,908; 5,834,439; 6,110,916; 6,399,663; 6,716,882; 5,627,159; 7,915,230; 7,531,693; 8,034,977; 7,166,745; 5,994,109; 6,033884; 6,150,168; 6,177,554; 6,083,741 6,458,026; 7,598,421; 7,820,624; 7,256,043; 7,704,969; 8,026,341; 7,145,039; 7,531,693; and 8,785,200; and International Publications WO 2004/063342, WO 0027795, WO 2004/105697, WO 2007/130073, WO 2012/142622, and WO 2013/158127, The term "pegylated lipid" as used herein generally refers to a lipid that is covalently conjugated to one or more polyethylene glycol moieties. Pegylated lipids for lipoplex embodiments herein include phosphatidylethanolamine (PE) based pegylated lipids such as, for example, 1,2-dimyristoyl-sn-glycero-3-phosphoethanolamine-N-[methoxy(polyethylene glycol)-MW] where MW refers to average MW of the polyethylene glycol moiety. Such dimyristoyl-PEG-PE lipids are commonly designated 14:0 PEG (MW) PE. The average MW of the polyethylene glycol moiety can be 25, 350, 550, 750, 1000, 2000, 3000, 5000, 6000, 8000 or 12000, for example. The fatty acid chains of the phosphatidylethanolamine based pegylated lipids may include, for example, a 1,2-dioleoyl group such as for 18:1 PEG (MW) PE, a 1,2-dipalmitoyl group such as for 16:0 PEG (MW) PE, or a 1,2-distearoyl-group such as for 18:0 PEG (MW) PE. Further phosphatidylethanolamine (PE) based pegylated lipids include, for example, 1,2-distearoyl-sn-glycero-3-phosphoethanolamine-N-[MOD(polyethylene glycol)-MW], also referred to as DSPE-MOD PEG(MW) wherein MOD refers to a functional moiety such as an amine, biotin, carboxylic acid, folate, maleimide, PDP, or carboxyfluorescein moiety. The MW may be 2000 or 5000, for example. Pegylated lipids for the embodiments described herein also include ceramide based pegylated lipids such as, for example, N-octanoyl-sphingosine-1-{succinyl[methoxy (polyethylene glycol)MW]}, designated C8 PEG (MW) ceramide, where MW is 750, 2000, or 5000, for example. Alternatively, the fatty acid moiety may have an N-palmitoyl (C16) group such as for C16 PEG (MW) ceramide.

A "liposomal composition" generally is a formulation that includes one or more liposomes. In some instances, the term "liposomal composition" may be used interchangeably with the term "transfection complex". These formulations are typically colloids, but can be dried formulations as well. A liposome is a vesicular colloidal particle composed of self-assembled amphiphilic molecules. Surface ligands, plant virus movement proteins, or fragments thereof disclosed herein can be incorporated into liposomal compositions of one or more cationic lipids, or one or more anionic lipids either or one or more pH sensitive lipids alone or optionally in combination with one or more helper lipids (i.e., a neutral lipid, a cholesterol or cholesterol derivative, lysolipid. or cationic lipids) that are processed using standard methods to form a liposome-containing colloid suspension. Liposomal compositions disclosed herein are those containing one or more cationic lipids, one or more helper lipids, optionally, in combination with one or more neutral and/or helper lipids, exosomes, total lipid extract from exosomes, targeting moieties, fusion agents, cell penetration agents, lysomotropic agents which are treated by any of the standard methods known in the art without limitation to form liposomes. The liposomal compositions may optionally contain one or more fusion agents. The liposomal compositions may optionally contain one or more liposomal compositions can be distinguished one from another by particle size measurements. Different compositions will exhibit differences in particle size and uniformity of particle size, e.g., average particle size, and polydispersity. Different compositions will exhibit differences in the extent of the composition that is in the form of liposomes. In some non-limiting embodiments, liposomal compositions will exhibit particle size in the range 120 nm and 800 nm and will exhibit generally lower polydispersity. Lipoplex particle size (with siRNA or other cargo) may range from about 40 nm to 135 nm. In some embodiments, lipoplex particle size is 50 nm to 120 nm, 50 nm to 100 nm, 60 nm to 90 nm, 70 nm to 90 nm, or about 85 nm.

The term "Lipid aggregate" or "lipoplex" is a generic term that includes liposomes of all types, both unilamellar and multilamellar, as well as vesicles, micelles, exosomes, micro-vesicles and more amorphous aggregates. A cationic lipid aggregate is a lipid aggregate comprising a combination of one or more cationic compounds, optionally in combination with non-cationic lipids (including neutral lipids), exosomes, such that the lipid aggregate has a net positive charge. Surface ligands or plant virus movement proteins or fragments thereof disclosed herein can be incorporated into lipid aggregate, optionally with a helper lipid and further optionally with one or more pegylated lipids and/or one or more targeting moieties, one or more fusion agents, one or more cell penetration agents and one or more lysosomotropic agents, one or more exosomes, which can then form a lipid-bioactive agent complex when contacted with a suitable bioactive agent. The terms "lipid aggregate" or "lipoplex" are generally used herein to refer to a "naked" transfection complex, i.e., a transfection complex that generally lacks a payload of bioactive agent to be delivered to a cell or to a tissue in vitro or in vivo.

The term "exosome" refers to the small membrane vesicles secreted by most cells that contain cell specific payloads of proteins, lipids and, genetic material and other biomolecules that are transported to other cells in different location of the tissue. Exosomes can be considered liposomal particles. Exosomes or lipid mixtures obtained therefrom, can be used in combination with other transfection agents or helper lipid mixtures. Exosomes are also referred to as microvesicles, epididimosomes, argosomes, exosome-like vesicles, microparticles, promininosomes, prostasomes, dexosomes, texosomes, archeosomes and oncosomes In one example of lipid constituents of exosomes is Lyso-PC (non limiting examples of which C-18, C-16, C-14 and mixture), Lyso-bisphospahtidic acid (non limiting example of which is C-18, C-16 and C-14), Sphingomyelin, Ceramides (non limiting examples C-8-C-24), Disaturated PC (non limiting examples (DSPC, DPPC, DMPC and others where Cn (n=8-25) Diunsaturated PC-MIX (non limiting examples of which are DOPC, DP(db)PC) phosphatidyl serine (PS), phosphatidyl inositol (PI), Disaturated PE (non limiting example, DSPE, DPPE, DMPE), Di-unsaturated PE-MIX (non limiting example DOPE DP(db)PE), phosphatidyl glycerol (PG), (non limiting examples of which are C-18C-22, Cholesterol, Diglycerides such as cardiolipin The term "lipid-bioactive agent" generally refers to the noncovalent association between a lipid or lipid aggregate and a bioactive agent, such as a nucleic acid, nucleotide, amino acid, peptide, a polypeptide, protein, protein nucleic complex, nutrient, exosome and the like.

As used herein "nucleic acid" and its grammatical equivalents will include the full range of polymers of single or double stranded nucleotides and includes nucleic acids (including DNA, RNA, and DNA-RNA hybrid molecules, Linked Nucleic acids (LNA), Bridged Nucleic acid (BNA)) that are isolated from a natural source; that are prepared in vitro, using techniques such as PCR amplification or chemical synthesis; that are prepared in vivo, e.g., via recombinant DNA technology; or that are prepared or obtained by any known method. A nucleic acid typically refers to a polynucleotide molecule comprised of a linear strand of two or more nucleotides (deoxyribonucleotides and/or ribonucleotides) or variants, derivatives and/or analogs thereof. The exact size will depend on many factors, which in turn depends on the ultimate conditions of use, as is well known in the art. The nucleic acids of the present invention include without limitation primers, probes, oligonucleotides, vectors, constructs, plasmids, genes, transgenes, genomic DNA, cDNA, LNA, BNA, RNA, mRNA, tRNA, miRNA, RNAi, siRNA, shRNA, stRNA, guide-RNA, gBlock, PCR products, restriction fragments, oligonucleotides and the like.

As used herein, the term "nucleotide" includes any monomeric unit of DNA or RNA containing a sugar moiety (pentose), a phosphate, and a nitrogenous heterocyclic base and may also include mono-, di- and triphosphate forms of such nucleotides. The base is usually linked to the sugar moiety via the glycosidic carbon (at the 1' carbon of pentose) and that combination of base and sugar is called a "nucleoside." The base characterizes the nucleotide with the four customary bases of DNA being adenine (A), guanine (G), cytosine (C) and thymine (T). Inosine (I) is an example of a synthetic base that can be used to substitute for any of the four, naturally occurring bases (A, C, G, or T). The four RNA bases are A, G, C, and uracil (U). Accordingly, a nucleic acid may be a nucleotide sequence comprising a linear array of nucleotides connected by phosphodiester bonds between the 3' and 5' carbons of adjacent pentoses. Other modified nucleotides are known and may be sued in the practice of the invention. The term nucleotide includes ribonucleoside triphosphates ATP, UTP, ITP, CTG, GTP or derivatives such as but not limited to [αS] ATP, 7-deaza-GTP and 7-deaza-ATP, 5-methyCTP, pseudoUTP, 4-thio-UTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, 5-methydCTP, pseudodUTP, 4-thio-dUTP, LNA-Nucleosidetriphosphates and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. The term nucleotides as used here also refer to nucleotides that contain modifiable groups. Illustrated examples of nucleotides with modifiable group include, but are not limited to, allyamine-CTP, allyamine dCTP, allyamine UTP, allyamine dUTP. According to the present invention, a "nucleotide" may be unlabeled or detectably labeled by well-known techniques. Detectable labels include, for example, biotin, radioactive isotopes, fluorescent labels, chemiluminescent labels, bioluminescent labels and enzyme labels. Various labeling methods known in the art can be employed in the practice of this invention. Transfection complexes of this invention can be used to deliver nucleotides to living cells to allow incorporation of modified nucleotides in nucleic acids.

"RNA" or "RNA molecule" refers to any RNA molecule or functional portion thereof, of any size, self-replicating, and having any sequence, from any source, including RNA viral, prokaryotic, and eukaryotic organisms. The RNA molecule may be chemically modified and in any form, including, but not limited to, linear or circular, and single or double stranded. Non-limiting examples of RNA molecules include mRNA, rRNA, tRNA, miRNA, mtRNA, tmRNA, RNAi, siRNA, shRNA, guideRNA, and stRNA. In some embodiments, siRNA molecules useful in the practice of the invention include, for example, those described in U.S. Patent Publication Nos. 2004/0014956, 2004/0054155, 2006/0009409, 2009/0023216, and 2010/0136695; and as described in International Publications WO 2003/064626, and WO 03/064625, all of which are incorporated by reference herein. Further siRNA molecules useful in the practice of the invention include, for example, those described in International Publication WO 2009/039173, which application is incorporated by reference herein.

The terms "peptide", "polypeptide", or "protein," as used herein refer to a string of at least three amino acids linked together by peptide bonds. The terms "protein" and "peptide" may be used interchangeably, though it is generally understood that a "polypeptide" or "protein" is larger than a peptide. "Peptide" may refer to an individual peptide or a collection of peptides.

The terms "polynucleotide" or "oligonucleotide," as used herein, refer to a polymer of nucleotides. Typically, a polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). The term "lipid" refers to hydrophobic or amphiphilic organic compounds inclusive of fats, oils and triglycerides.

DISCLOSED ASPECTS AND EMBODIMENTS

Transfection complexes suitable for the delivery of one or more biologically active agents to a cell or a tissue in vitro or in vivo are provided for herein. The transfection complexes described herein include one or more cell surface ligands, plant virus movement proteins, or fragments thereof that enhance transfection in combination with a transfection agent as part of a transfection complex. In some embodiments, the transfection complexes disclosed herein optionally further comprise one or more components selected from the group consisting of one or more helper lipids, one or more pegylated lipids, one or more cationic lipids, one or more cationic polymers one or more targeting moieties, exosomes, total lipid isolated from exosomes, total lipid and protein isolated form exosomes, a combination thereof. In some embodiments, transfection complexes disclosed herein further comprise one or more components selected from the group consisting of peptide or non-peptide transfection enhancers, consisting of peptide or non-peptide surface ligand, cell penetration peptide or non-peptide cell penetration agent, fusogenic peptide or non-peptide fusion agents, peptide or non-peptide endosomal release agents, lysomolotropic agents, nuclear targeting agents (such as, e.g., a peptide containing one or more nuclear localization sequences), and a combination thereof.

Plant virus movement proteins are involved in moving the genome of plant viruses from cell to cell and from cell membrane to nucleus and back to the cell membrane and then into the neighboring cells using the plant host cell machinery in combination with the plant virus movement protein. All plant viruses have movement protein but no all have been studied. These virus movement proteins, or fragments of such have utility for moving DNA or RNA in eukaryotic cells from the cell cytoplasm to the nucleus or nucleus to cell membrane. The virus genera and virus families of Tobamovirus, Dianthovirus, Umbravirus, Bromovirus, Cucumovirus, Begomovirus, Potyvirus, Hordei-like virus, Potex-like virus, Begomoviruses, Geminiviridae have example of virus movement proteins that move nucleic acid to and from the cell membrane and to the nucleus if a DNA virus. Utilization of these plant proteins to enhance transfection of both DNA and RNA are disclosed.

In some embodiments, helper lipids suitable for use in the preparation and formation of transfection complexes disclosed herein include, though are not limited to a cholesterol, a cholesterol derivative, one or more sterols, including phytosterols, zoosterols and hopanoids, or any of the neutral or cationic lipids that are known to allow or to facilitate the introduction of exogenous bioactive molecules to the interior of a cell or of a tissue. The helper lipid or helper lipids may be derived form exosomes or complete exosomes. In some embodiments, more than one helper lipid is used in the formulation of the transfection complexes described herein. In some embodiments, the transfection complexes disclosed herein comprise no helper lipid.

Illustrative though non-limiting neutral or cationic lipids suitable for use as helper lipids in accordance with some of the embodiments set forth herein include saturated and unsaturated alkyl and alicyclic ethers and esters of amines, amides or derivatives thereof. In some embodiments, straight-chain or branched alkyl and alkene groups of cationic lipids contain from 1 to about 25 carbon atoms. In certain embodiments, straight-chain or branched alkyl or alkene groups have six or more carbon atoms. In some embodiments, straight-chain or branched alkyl or alkene groups have eight to about twenty carbon atoms. In other embodiments, alicyclic groups contain from about 6 to 30 carbon atoms, or, alternatively, eight to twenty carbon atoms. In some embodiments, the alicyclic groups include cholesterol and other steroid groups. In certain embodiments, cationic lipids are prepared with a variety of counter ions (anions) including among others: a halide (i.e., $Cl^-$, $Br^-$, $I^-$, $F^-$), acetate, trifluoroacetate, sulfate, nitrite, triflate, and nitrate Embodiments of pegylated lipids suitable for use in the preparation and formation of the transfection complexes disclosed herein are any lipid or mixture of lipids that are compatible with the formation of transfection complexes described herein, and with the administration thereof to an animal or to a human in vivo, or to tissues or cells in vitro. The pegylated lipids used with the presently described transfection complexes include, but are not limited to, a PEG polymer having a molecular weight between about 250 daltons and about 12,000, or in some embodiments, about 350 daltons and about 6,000 daltons, or, in some embodiments, between about 500 daltons and about 1,000 daltons, or, in some embodiments, between about 1,000 daltons and about 2,000 daltons, or, in some embodiments, between about 2,000 daltons and about 5,000 daltons.

In some embodiments, the presently disclosed transfection complexes include one or more biologically active agents to be delivered to a cell or to a target tissue in vitro or in vivo. Suitable biologically active agents include, but are not limited to, any molecule that is capable of forming a transfection complex with the presently described transfection reagents and that elicits a biological response when delivered to the interior of a cell or cells or to a tissue in vivo or in vitro. In some embodiments, biologically active agents contemplated for use in the presently described embodiments are cationic, neutral or anionic agents. In some embodiments, the biologically active agents suitable for formulation in the presently disclosed transfection complexes include a protein, DNA or RNA molecule, either alone or in combination with other protein, DNA or RNA molecules in various combinations, though are not limited to; nucleic acids (including but not limited to single or double stranded linear or circular DNA molecules including cDNA molecules, single or double stranded RNA molecules, mRNA, modified mRNA that has increase stability, small interfering RNA (siRNA) molecules, small hairpin RNA (shRNA) molecules, guideRNA (gRNA), Cas9 protein, Cas9 protein/guide RNA, Cas9DNA/guideRNA, Cas9mRNA/guideRNA, Cas9mRNA/gRNA/s sDNA/RecAprotein, Cas9mRNA/gRNA/s sDNA/recombination protein, Cas9protein/gRNA/ssDNA/RecAprotein, Cas9protein/gRNA/s sDNA/recombination protein, microRNA (miRNA) molecules, oligonucleotides, anti-sense oligonucleotides, sense oligonucleotides), polypeptides, antibodies, oligopeptides, therapeutic peptides or protein molecules, peptide nucleic acids (PNAs), cationic, anionic or neutral organic molecules or drugs, in addition to pharmaceutically acceptable salts thereof. In another embodiment, nutrients required for cell growth or nutrients that can be used to enhance protein expression can be delivered into cells by transfection complexes disclosed herein.

In certain non-limiting illustrative embodiments, the transfection complexes disclosed herein deliver nucleic acid molecules into cells or tissues in vitro or in vivo, including the delivery of RNA interference molecules (RNAi) or small interfering RNA molecules (siRNA, shRNA or miRNA) into cells for inhibition of gene expression.

In some embodiments, the cell surface ligands, the plant virus movement proteins, peptide fragments thereof, or the presently disclosed transfection complexes are used to deliver mRNA molecules or mixtures of mRNA and DNA molecules into a cell or a tissue in vivo or in vitro to promote the expression of a specific protein or proteins. mRNA reprogramming molecules or telomerase are non-limiting examples of mRNA molecules. Cas9 mRNA, and DNA molecules that code for gRNA, CRE mRNA and LoxP containing DNA molecules, SV40T antigen mRNA and DNA molecules with the SV40 origin of replication are non-limiting examples of mRNA and DNA pairs that have utility. Preformed transfection complexes that contain mRNA are non-limiting illustrative embodiments of transfection complexes disclose herein. Telomerase mRNA transfection complexes or Telomerase mRNA and SV40 Large T-antigen complexes as a media supplement are disclosed herein. In some embodiments, preformed transfection complexes containing mRNA are made and the DNA molecule is added to the complex at a later time.

In some embodiments, the cell surface ligands, plant virus movement proteins or peptide fragments thereof, or the presently disclosed transfection complexes are used to deliver DNA molecules (including cDNA molecules) into a cell or a tissue in vivo or in vitro to promote the expression of a specific protein or proteins or to synthesize specific RNA molecules, including but not limited to mRNA molecules or RNAi or miRNA or shRNA or sgRNA molecules are also provided.

In some embodiments, the cell surface ligands, plant virus movement proteins, or peptide fragments thereof presently disclosed, are used to deliver proteins or protein nucleic acid complexes into a cell or a tissue in vivo or in vitro to effect the function of the protein, as for example in gene editing. In some embodiments, the transfection complexes described herein contain, one or more surface ligands, one or more fusogenic peptides, one or more nuclear targeting peptide, one or more cationic lipid, or one or more neutral lipid. Non-limiting examples of proteins and protein nucleic acid complexes include, recombinases, CRISPR enzymes, Cre recombinase and Cre fusion proteins, transcription activator like effector nucleases (TALEN), genome editing proteins and CRISPR-Cas9 nuclease/guide RNA complex.

In some embodiments, proteins such as RNA polymerase, RNA binding proteins or peptides, and transcription factors are bound to nucleic acids and are delivered to cells with the transfection reagents disclosed herein. In certain embodiments, proteins are made anionic by the addition anionic peptides or anionic polymers designed to attach to the protein or an anionic amino acid is added to the C-terminus or N-terminus of the protein.

In some embodiments, the transfection complexes described herein may optionally include one or more fusogenic or cell-penetrating peptides. A fusogenic or cell-penetrating peptide is any peptide molecule that is capable of promoting the fusion of a lipid-containing complex to a cell membrane (either a plasma membrane or an endosomal membrane). A variety of fusogenic or cell-penetrating peptides are known in the art and it is well within the skill level of a practitioner to identify suitable fusogenic or cell-penetrating peptides and condition for the use thereof in the present invention without undue experimentation.

In some embodiments, the transfection complexes described herein optionally include one or more transfection helpers or targeting moieties in combination with the cell surface ligands, plant virus movement proteins, or peptide fragment thereof described herein. In some embodiments, the targeting moiety is a peptide, a modified peptide, an antibody, a modified antibody, a receptor molecule, a modified receptor molecule, a single or a double stranded nucleic acid molecule, a modified single or double stranded nucleic acid molecule, a peptide or nucleic acid aptamer, a modified peptide or nucleic acid aptamer, an organic molecule, a polysaccharide, an exosome, or any other molecule that is capable of targeting a transfection complex to specific tissue or cell type for targeted delivery of a biologically agent thereto, such as will be readily apparent to those having ordinary skill level in the art. In some embodiments, modification of a peptide, an antibody, a nucleic acid, an aptamer, and the like includes conjugating the peptide, antibody, nucleic acid, aptamer, and the like to a PEG moiety. Alternatively, said modification includes conjugating the peptide, antibody, nucleic acid, aptamer, and the like to a PEG-lipid moiety. A variety of targeting moieties are widely known to those skilled in the art, and all are contemplated for use with the presently described embodiments, without limitation.

In some embodiments, the transfection complexes disclosed herein are stable for up to one year and are either contacted with the cells or tissues to be transfected, or are administered to a subject immediately or shortly after being formed. In some embodiments, the transfection complexes disclosed herein are optionally stored for a period of time prior to being contacted with the cells or tissues, or being administered to a subject. The transfection complexes are stable and may be stored for a time period of at least 30 minutes, at least 45 minutes, at least 1 hour, at least 2 hours, at least 3 hours, at least 4 hours, at least 5 hours, at least 10 hours, at least 15 hours, at least 20 hours, at least 24 hours, at least 48 hours, at least 72 hours, at least 5 days, at least 7 days, at least 14 days, at least 28 days, at least 1 month, at least 2 months, at least 3 months, at least 4 months, at least 5 months, at least 6 months or at least 1 year at room temperature, or at a temperature greater than freezing, up to about room temperature. In some embodiments, the formulations described herein include one or more stabilizing agents, preservatives, buffers, and the like, that aid in the long-term stabilization and storage of bioactive formulation, such as will be readily understood by the skilled practitioner of the biological and pharmaceutical arts, and without requiring undue experimentation to achieve. It is also understood, that the storage period can be between any of the aforesaid time periods, for example between 31 minutes and 1 hour or between 1 hour and 24 hours.

In another aspect, disclosed herein are methods for the preparation of functional transfection complexes containing cell surface ligands, plant virus movement proteins, or peptides derived therefrom, the complexes being as described herein. In some embodiment the functional transfection complex may be used for the preparation of synthetic liposomes or exosomes that contain biologically active macromolecules. In some embodiments, the methods include the step of forming a liposomes or exosome composition containing one or more plant virus movement proteins or peptide fragments or from surface ligands described herein, optionally in combination with one or more helper lipids, stabilizing lipids, transfection helpers, exosomal lipids or lipid extracts, pegylated lipids, targeting moieties, fusion agents, cell penetration agent, lysosomotropic agent. In some embodiments, the methods include the step of forming a lipid-aggregate by encapsulating a biologically active agent in a composition containing one or more surface ligands, plant virus proteins, or peptide fragments thereof described herein, optionally in combination with one or more helper lipids, stabilizing lipids, transfection helpers, pegylated lipids, targeting moieties, fusion agents, lysosomotropic agent and/or exosomes. In some embodiments, the methods alternatively include: 1) mixing one or more surface ligands, plant virus movement proteins, or peptide fragments thereof, with one or more transfection compounds, which optionally include one or more helper lipids, exosomes, surface ligands, stabilizing lipids, transfection helpers, targeting moieties, fusion agents, lysosomaotropic agent, optionally with one or more pegylated lipids, or a salt thereof, in an, an aqueous, alcohol/aqueous, or alcohol solution wherein the alcohol concentration is <10%, <25%, <50%, or <99%; 2) mixing one or more surface ligands, plant virus movement proteins, or peptide fragments thereof, with one or more transfection compounds, which optionally include one or more helper lipids, exosomes, stabilizing lipids, transfection helpers, targeting moieties, surface ligands, fusion agents, cell penetration agents, lysosomotropic agent, and one or more pegylated lipids, or a salt thereof, in a molar percentage such that the one or more transfection compounds are present at 1%-90%; 3) mixing one or more surface ligands, plant virus movement protein, or peptide fragment thereof, with one or more transfection compounds, which optionally include one or more helper lipid, exosomes, stabilizing lipids, transfection helpers, targeting moieties, surface ligands, fusion agents, lysosomotropic agent, one or more pegylated lipids, or a salt thereof, in a molar percentage such that the Pegylated lipids are present at <50%; and 4) mixing one or more surface ligands, plant virus movement proteins, or peptides derived therefrom, with one or more transfection compounds, which optionally include one or more helper lipid, exosomes, stabilizing lipids, transfection helpers, targeting moieties, surface ligands fusion agents, cell penetration agents, lysosomotropic agent, one or more pegylated lipids, or a salt thereof, wherein the pegylated lipid has a polyethylene glycol molecular weight of about 2000-12000 and a fatty acid chain length of $C_6$-$C_{20}$ alkyl, or $C_{10}$-$C_{20}$ alkenyl; and complexing the lipid aggregate in an aqueous, alcohol/aqueous, or alcohol solution with the bioactive agent to form a transfection complex, wherein the alcohol concentration is <50%, preferably less than 40% if pegylated lipids are present. In some embodiments, the alcohol is ethanol. In some embodiments, the alcohol is a pharmaceutically acceptable alcohol such as an alcohol that is liquid at about room temperature, for example, ethanol, propylene glycol, 2-(2-ethoxyethoxy)ethanol (Transcutol™), benzyl alcohol, glycerol, polyethylene glycol 200, polyethylene glycol 300, polyethylene glycol 400 or a mixture thereof. In some embodiments, the alcohol for mixing is different than the alcohol for complexing. Formulations of lipid aggregates as provided above can be provided in 0% to 100% ethanol. In some embodiments, the helper lipid is a neutral lipid. The ratio of cationic to neutral lipid can vary from 100% to 0.1% cationic lipid.

In another embodiment preformed lipid aggregates, exosomes, cationic exosomes or liposomes containing cationic, anionic, and or neutral lipids are mixed with cell surface ligands, plant virus movement proteins, or peptides derived therefrom describe herein. In certain embodiments, the lipid aggregates, exosomes or liposomes are optionally formulated with one or more transfection enhancers such as helper lipids, stabilizing lipids, transfection helpers, pegylated lipids, other targeting moieties, cell surface ligands, fusion agents, cell penetration agents, and or lysosomotropic agents. In some embodiments, the cell surface ligands, plant virus movement proteins, or peptides derived therefrom as described herein are added to these formulations at any point prior to or after the bioactive agent is loaded into the transfection complex.

In another embodiment a mixture of cationic lipid, neutral lipids and or total lipid extract of exosomes are dissolved in organic solvent such as chloroform and mixed with aqueous solutions optionally containing buffers and one or more cell surface ligands, plant virus movement proteins, or peptides derived therefrom, and optionally one or more transfection enhancers, one or more fusion agents, one or more cell penetration agents, one or more nuclear localization agents and subjected to reveres evaporation to remove the organic solvent leaving behind a lipid aggregate or liposome in solution.

In another embodiment a mixture of cationic lipid, neutral lipids and or total lipid extract of exosomes are dissolved in organic solvent such as chloroform or ethanol and mixed with aqueous solutions optionally containing buffers and one or more plant virus movement proteins or peptides derived from plant virus movement proteins, and optionally one or more transfection enhancers, one or more fusion agents, one or more nuclear localization agents, one or more cell surface ligand and subjected to reveres evaporation to remove the organic solvent leaving behind a lipid aggregate or liposome in solution.

In another embodiment, a mixture of cationic lipids and, lipids (total lipid extract of exosomes, lipids from exosomes, neutral lipids) in a water, alcohol or in a alcohol water mixture is added to an alcohol solution or alcohol water solution containing buffers and plant virus movement proteins or peptides derived from plant virus movement proteins, and optionally one or more transfection enhancers, one or more exosomes, one or more fusion agents, one or more nuclear localization agents, one or more surface ligands and this solution is optionally micro fluidization, extruded or sonicated to form lipid aggregates or liposomes.

In another embodiment, a mixture of cationic lipids and neutral lipid in a water, alcohol or in an alcohol/water mixture is added to an aqueous solution containing buffers and one or more cell surface ligands, plant virus movement proteins, or peptides derived therefrom, and optionally one or more transfection enhancers, one or more exosomes, one or more fusion agents, one or more cell penetration agents, one or more nuclear localization agents one or more surface ligands and this solution is optionally micro fluidization, extruded or sonicated to form lipid aggregates or liposomes.

In another aspect, disclosed herein are methods for screening for a tissue-based delivery of a transfection complex or cell type. In some embodiments, the method comprises the step of preparing a plurality of transfection complexes, each transfection complex having at least one cell surface ligand, plant virus movement protein, or peptides derived therefrom, in combination with at least one nucleic acid that facilitates detection of delivery to a tissue or cell type. In some embodiments, the nucleic acid is an RNA molecule or a DNA molecule that encodes a protein that can be directly detected (such as, e.g., Green Fluorescent Protein (GFP), Red Fluorescent Protein, Luciferase, or the like), or encode a protein that effects expression of a protein that can be directly detected.

In an embodiment, a method for screening for a cell based or tissue-based delivery of at least one cell surface ligand, plant virus movement protein, or peptide derived therefrom, comprises the step of preparing a plurality of unique transfection complexes, each transfection complex having at least cell surface ligand, plant virus movement protein, or peptide derived therefrom in combination with an mRNA or a cDNA that encodes the detectable protein or a specific transcription factor. Each unique transfection complex is delivered either to cells in culture, intravenously, subcutaneously, or to a tissue to a subject. After a predetermined amount of time, cells in culture or tissues from the subject are harvested and the expression of the detectable protein in various tissues is detected by gross examination, histological examination or by molecular detection (PCR, Western blotting, or the like), or imaged in vivo using the IVIS® Imaging System (Caliper), to determine to which tissue or tissues the transfection complexes containing specific transfection compounds are delivered.

In an embodiment, a method for screening cells in culture or tissue-based delivery of a transfection complex comprises the step of preparing a plurality of unique transfection complexes, each transfection complex having at least one test cell surface ligand, plant virus movement protein, or peptide derived therefrom in combination with an mRNA or a cDNA that encodes a specific transcription factor. Each unique transfection complex may be delivered to cells in culture, intravenously, subcutaneously, or to a tissue to a transgenic animal that expresses a reporter gene (such as, e.g., luciferase) under the control of the specific transcription factor. After a predetermined amount of time, tissues from the transgenic animal may be harvested and the expression of reporter gene in various tissues may be detected by gross examination, histological examination or by molecular detection (PCR, Western blotting, or the like). If the reporter gene is luciferase, detection may be accomplished in-vivo using the IVIS® Imaging System (Caliper).

In some embodiments, cell surface ligand, plant virus movement protein, or peptide derived therefrom of the presently disclosed transfection complexes are used to deliver exosomes into a cell or a tissue in vivo or in vitro to effect the function of the biological cargo in the exosomes. In some embodiments, the transfection complex described herein comprise one or more fusogenic peptides, one or more cell penetration agents, one or more nuclear targeting peptide, one or more cationic lipid, one or more plant virus movement proteins or peptides derived from plant virus movement proteins, one or more surface ligands or one or more neutral lipids. In certain embodiments, the transfection complexes described herein comprise one or more of the cationic lipids described in Formula I.

In another aspect, disclosed herein are compositions and methods that provide improved efficiency for introducing molecules and macromolecules, such as nucleic acids, proteins, peptides, nutrients and pharmaceuticals into cells. Accordingly, provided herein are compositions comprising a nucleic acid molecule, a transfection agent and a transfection enhancer.

In some embodiments, the transfection enhancer is a surface ligand that comprises amino acid sequences derived from a cell binding adhesion proteins. Collagen, fibronectin, lamin, veronectin, cadherin, nidogen, fibrinogen, elastin, bone asialoprotein, osteopontin and tenascin-C are non-limiting examples of cell binding adhesion proteins. In some embodiments, the surface ligand is the above-listed full-length protein. In other embodiments, the surface ligand is a fragment of the above-listed protein having greater than 5 amino acids in length. In other embodiments, the length of the fragment of the above-listed protein is greater than 5 amino acids is greater than 10 amino acids, greater than 15 amino acids, greater than 20 amino acids, greater than 25 amino acids, greater than 30 amino acids, greater than 35 amino acids, or greater than 40 amino acids.

In some embodiments, cell surface ligand, plant virus movement protein, or peptide derived therefrom proteins and describe herein comprise a nucleic acid binding moiety functionally linked to the amino acid sequence of the cell surface ligand, plant virus movement protein, or peptide derived therefrom proteins. Suitable nucleic acid binding moieties include, but are not limited to, a polycationic peptide sequence, a polyamine, a peptide nucleic acid, spermine, spermidine, carboxyspermidine, carboxy spermine, spermine and spermidine analogs, nucleic acid intercalaters, and the like. In certain embodiments, the nucleic acid binding moiety is covalently linked to the transfection promoting cell surface ligand comprising adhesion protein amino acid sequences. In further embodiments, the transfection agent is a cationic lipid, such as those described below, a polyamine, a polycationic peptide sequence, a cationic dendrimer, or the like. In some embodiments, the cell surface ligand adhesion sequence or peptide derived from a plant movement protein is a multimer of itself or other adhesion sequences. In certain embodiments, the cell binding adhesion or peptide derived from a plant movement protein amino sequence is cyclized. In other embodiments, the surface ligands or peptide derived from a plant movement protein also contain other peptide sequence that enhance transfection efficiency, such as linkers, spacers, or nuclear targeting sequences.

In some embodiments, cell surface ligand, plant virus movement protein, or peptide derived therefrom described herein are attached directly to the binding molecule by covalent bonding, or are connected to the binding molecule via a spacer. The term "spacer," or "linker," which are used interchangeably herein, as used herein refers to a chemical structure that links two molecules to each other. In some embodiments, the spacer binds each molecule on a different part of the spacer molecule. In other embodiments, the spacer is a hydrophilic moiety and comprises about 6 to 30 carbon atoms. In other embodiments, the spacer comprises a polyether, for example $-CH_2-O-(CH_2-CH_2-O-)_iCH_2-$. In other embodiments, the spacer comprises a hydrophilic polymer, for example $[(gly)_i(ser)_j]_k$ (SEQ ID NO: 585). In these formulae i ranges from 1 to 6, j ranges from 1 to 6, and k ranges from 3 to 20. In some embodiments, the spacer is a peptide of sequence APYKAWK (SEQ ID NO:505). In other embodiments, the spacer is a sequence that is degraded in vivo by a peptidase.

In some embodiments, the cell surface ligand, plant virus movement protein, or peptide derived therefrom described herein are functionally linked to a lipid, such as a cationic or neutral lipid. In some of these embodiments, the linked moiety is used for delivery of macromolecules into cells. For example, a cell surface ligand, plant virus movement protein, or peptide derived therefrom, or a cell binding adhesion peptide sequences amino acid sequence is covalently linked to a lipid, such as a cationic lipid, a lysolipid, using methods known in the art.

In certain embodiments, the cell surface ligand, plant virus movement protein, or peptide derived therefrom sequences described herein also are functionally linked to an amino acid sequence that inserts itself into lipid membranes, such as membrane anchor peptides or proteins. In other embodiments, the cell surface ligand peptide sequences are linked to chemical compositions that associate with lipids.

In other embodiments, the transfection complexes or liposomal compositions with the cell surface ligand, plant virus movement protein, or peptide derived therefrom described herein also comprise other transfection enhancing agents, such as a nuclear localization protein or peptide, a fusogenic peptide or protein, a transport peptide or protein, a viral peptide or protein, or a lysomoltropic agent. In certain embodiments, the viral peptide is derived from a virus enveloped or non-enveloped virus, for example an influenza virus, a vesicular stomatitis virus, an adenovirus, an alphavirus, a Semliki Forest Virus, a hepatitis virus, a herpes virus, an HIV virus, or a simian virus. In some embodiments, the transfection enhancing agent is, for example, insulin, a transferrin, a epidermal growth factor, a fibroblast growth factor, a cell targeting antibody or fragment from an antibody, a lactoferrin, a fibronectin, an adenovirus penton base, Knob, a hexon protein, a vesicular stomatitis virus glycoprotein, a Semliki Forest Virus core protein, an influenza hemagglutinin, a hepatitis B core protein, an HIV Tat protein, a herpes simplex virus VP22 protein, a histone protein, an arginine rich cell permeability protein, a high mobility group protein, and invasin protein, an internalin protein, an endotoxin, a diptheria toxin, a shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bacteriacidal-permability-increasing protein, a nisin, a buforin, or fragments thereof. In other embodiments, the transfection enhancing agent is chloroquine, a lysosomotrophic compound or combinations thereof. In other embodiments exosomes or exosomal derived lipids or proteins are the transfection enhanceagent. In other embodiments, the transfection enhancer agent comprises multimers of the same or different peptides or proteins.

Suitable nuclear localization peptides or proteins included in transfection complexes or liposomal compositions include, but are not limited to, a sequence selected from the group consisting of SEQ ID NOs:1-41, as set forth in Table 1, below, or in the sequence listings.

Proteins such as histones, protamines, HMG proteins, and viral core proteins or coat proteins comprise nuclear localization proteins. In some embodiments, these proteins or fragments thereof are used to enhance transfection. In some embodiments, the nuclear localization peptide is optionally linked to a nucleic acid binding moiety, for example via a covalent linkage. Spacer sequences are optionally used between the DNA binding sequence and the nuclear localization sequence. In some embodiments, the nuclear localization sequences are linked to helper lipids or other peptides proteins or compounds that associate with lipid bilayers.

In some embodiments, the compositions described herein also comprise a fusion agent or combinations of fusion agents, which in some embodiments also function as an amphipathic peptide. Suitable fusion peptides include, but are not limited to, a sequence selected from the group consisting of SEQ ID NOs:42-92, as set forth in Table 1, below, or in the sequence listings.

In some embodiments, the fusion agent is optionally linked to a nucleic acid binding moiety, for example via a covalent linkage. The peptides KK, KKK, KKKK (SEQ ID NO:97), RR, RRR, RRRR (SEQ ID NO:105) can be linked to fusion agents of SEQ ID NOs:42-92. In certain embodiments, fusion peptides are linked to helper lipids, cationic lipids, or other peptides or proteins that associate with lipid bilayers. Spacer sequences are optionally used between the DNA binding sequence and the fusion agent sequence In certain embodiments, the compositions disclosed herein comprise a cell penetration agent or combinations of cell penetration agents. Suitable cell penetration agents include, but are not limited to, a sequence selected from the group consisting of SEQ ID NOs:93-96 as set forth in Table 1, below, or in the sequence listings.

In some embodiments, the cell penetration agents are optionally linked to a nucleic acid binding moiety, for example via a covalent linkage. In other embodiments, the cell penetration agents are linked to helper lipids or other peptides or proteins that associate with lipid bilayers.

In some embodiments, the nuclear localization sequences, the fusion agents, cell surface ligand or the cell penetration agents are linked to the GPI anchor peptides, the sequence FTLTGLLGTLVTMGLLT (SEQ ID NO:504) being a non limiting example.

In some embodiments, the nucleic acid binding moieties that are linked to different transfection enhancer and are part of transfection complexes have different binding affinity for nucleic acids depending on the needed functionality for attachment, condensation of nucleic acid, and the rate of release of nucleic acid from the nucleic acid binding moiety. Suitable nucleic acid binding moieties include, but are not limited to a polycationic peptide sequence, a polyamine, a peptide nucleic acid, spermine, spermidine, carboxyspermidine, carboxy spermine, spermine and spermidine analogs, nucleic acid intercalaters, and the like.

In some embodiments, the compositions described herein comprise combinations of different transfection enhancers with different nucleic acid binding moieties. Suitable nucleic acid binding peptides include, but are not limited to a sequence of SEQ ID NOs:97-149, as set forth in Table 1, below, or in the sequence listings.

In some embodiments, the nucleic acid binding moieties also serve as transfection enhancers when bound to nucleic acids, or alternatively serve as condensing agents. Suitable nucleic acid condensing peptides include, but are not limited to, a sequence selected from the group consisting of the peptides of SEQ ID NOs:97-149 as set forth in Table 1, below, or in the sequence listings. In some embodiments, multimers of these peptides are also synthesized and used as condensing agents. In some embodiments, nuclear localization sequences are also used as condensing agents if they have enough cationic charge.

Suitable nucleic acid binding moieties include, but are not limited to a polycationic peptide sequence, a polyamine, a peptide nucleic acid, spermine, spermidine, carboxyspermidine, carboxy spermine, spermine and spermidine analogs, nucleic acid intercalaters, and the like One skilled in the art will readily recognize that the surface ligand chosen depends on which receptor is being bound. Since different types of cells have different receptors, this provides a method of targeting nucleic acid, peptides, protein, and compounds to specific cell types, depending on which cell surface ligand is used. Thus, the preferred cell surface ligand or ligands may depend on the targeted cell type.

In some embodiments, the transfection enhancers that are used in combination with the cell surface ligand, plant virus movement protein, or peptide derived therefrom disclose herein include, but are not limited to, the peptides or proteins selected from the group consisting of a collagen, a fibronectin, a lamin, a veronectin, a cadherin, a nidogen, a fibrinogen, a elastin, a bone asialoprotein, a osteopontin, a tenascin-C, Avadin, insulin, a transferrin, a epidermal growth factor, a fibroblast growth factor, a cell targeting antibody, a lactoferrin, an enveloped virus, a non-enveloped virus, an adenovirus penton base, a knob protein, a hexon protein, a vesicular stomatitis virus glycoprotein, a Semliki Forest Virus core protein, an influenza hemagglutinin, a hepatitis B core protein, an HIV Tat protein, a herpes simplex virus VP22 protein, a histone protein, an arginine rich cell permeability protein, a high mobility group protein, invasin protein, internalin protein, an endotoxin, a non-toxic diptheria toxin, a non-toxic shigella toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bacteriacidal-permability-increasing protein, a nisin, a buforin, a fragment thereof, and a sequence selected from the group consisting of SEQ ID NOs:150-503, as set forth in Table 1, below, or in the sequence listings.

In some embodiments, the transfection enhancing agent is chloroquine, a lysosomotrophic compound or combinations thereof. In certain embodiments, the transfection enhancer agent comprises multimers of the same or different peptide enhancers, protein or protein fragments of transfection enhancers.

In some embodiments, the aforementioned peptides are optionally linked to a moiety selected from the group consisting of a nucleic acid binding moiety, a helper lipid, a cationic lipid, a cationic polymer, and a GPI anchor peptide.

In certain embodiments, the aforementioned peptides are optionally linked to a chemical moiety of Formula I,

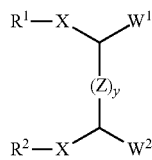

(I)

or a pharmaceutically acceptable salt thereof, where $W^1=W^2=CH_2-N(R^3R^4)$, $R^1=R^2=C_8-C_{22}$ alkyl, $X=O$; $R^3=CH_3$, $R^4=-C(=O-C(NH_2)-CH_2-(CH_2)n-NH_2$, $n=0-6$, $y=0$; or $W^1=W^2=CH_2-N(R^3R^4)$, $R^1=R^2=C_8-C_{22}$ alkyl, $X=O$; $R^3=CH_3$, $R^4=-C(=O-C(NH_2)-CH_2-(CH_2)n-OH$, $n=0-6$, $y=0$; or $W^1=W^2=CH_2-N(R^3R^4)$, $R^1=R^2=C_8-C_{22}$ alkyl, $X=O$; $R^3=CH_3$, $R^4=-C(=O-C(OH)-CH_2-(CH_2)n-NH_2$, $n=0-6$, $y=0$; or $W^1=W^2=CH_2-N(R^3R^4)$, $R^1=R^2=C_8-C_{22}$ alkyl, $X=O$; $R^3=CH_3$, $R^4=-C(=O)-C(NH-iso-butyl)-CH_2-(CH_2)n-O-iso-butyl$, $n=0-6$, $y=0$; or $W^1=W^2=CH_2-N(R^3R^4)$, $R^1=R^2=C_8-C_{22}$ alkyl, $X=O$; $R^3=CH_3$, $R^4=-C(=O-C(NH_2)-CH_2-(CH_2)n-C(=NH)-NH_2$, $n=0-6$, $y=0$; or $W^1=W^2=CH_2-N(R^3R^4)$, $R^1=R^2=C_8-C_{22}$ alkyl, $X=O$; $R^3=CH_3$, $R^4=-C(=O-C(NH_2)-CH_2-(CH_2)n-His$, $n=0-6$, $y=0$; or $W^1=W^2=CH_2-N(R^3R^4)$, $R^1=R^2=C_8-C_{22}$ alkyl, $X=O$; $R^3=CH_3$, $R^4=-C(=O-spermine$, $y=0$; or $W^1=W^2=CH_2-N(R^3R^4)$, $R^1=R^2=C_8-C_{22}$ alkyl, $X=O$; $R^3=CH_3$; $R^4=H$, $y=0$; or $W^1=W^2=CH_2-N(R^3R^4)$, $R^1=R^2=C_8-C_{22}$ alkyl, $X=O$; $R^3=CH_3$; $R^4=CH_2(CH_2)_m-NH_2$; $m=1-6$, $y=0$; or $W^1=W^2=CH_2-N(R^3R^4)$, $R^1=R^2=C_8-C_{22}$ alkyl, $X=O$; $R^3=CH_3$; $R^4=CH_2(CH_2)_m-NH-C(=O)-spermine$; $m=1-6$, $y=0$; or $W^1=W^2=CH_2-N(R^3R^4)$, $R^1=R^2=C_8-C_{22}$ alkyl, $X=O$; $R^3=CH_3$; $R^4=CH_2(CH_2)_m-NH-(C=O)-amino$ acid side chain; $m=1-6$, $y=0$; or $W^1=W^2=CH_2-N(R^3R^4)$, $R^1=R^2=C_8-C_{22}$ alkyl, $X=O$; $R^3=CH_3$; $R^4=(CH_2)_m(CH-OH)(CH_2)_m-NH_2$, $y=0$; or $W^1=W^2=CH_2-N(R^3R^4)$, $R^1=R^2=C_8-C_{22}$ alkyl, $X=O$; $R^3=CH_3$; $R^4=CH_2(CH_2)n-NH_2$, $y=0$; or $W^1=H$, $W^2=CH_2-N(R^3R^4)CH_2-R^5$; $R^3=R^4=CH_3$; $R^5=H$, $y=0$; or $W^1=H$; $W^2=CH_2-O-P(=O)(OMe)-O-CH_2CH_2-NH-C(=O)-spermine$, $y=0$; or $W^1=H$; $W^2=CH_2-O-P(=O)(OMe)-O-CH_2CH_2-NH-C(=O)-amino$ acid side chain, $y=0$; or $W^1=H$; $W^2=CH_2-O-P(=O)(OMe)-O-CH_2CH_2-N^+(CH_3)_3Cl$, $y=0$; or $W^1=H$; $W^2=CH_2-O-P(=O)(O^-)-O-CH_2CH_2-NH-C(=O)-spermine$, $y=0$; or $Z=(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)n-NH_2$, $n=0-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)n-OH$, $n=0-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(OH)-CH_2-(CH_2)_n-NH_2$, $n=0-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH-iso-butyl)-CH_2-(CH_2)_n-O-iso-butyl$, $n=0-6$, $y=1$; or $Z=(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-C(=NH)-NH_2$, $n=0-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-His$, $n=0-6$, $q=1-3$, $y=1$; or $Z=(CH_2)_q$ $W^1=W^2=CH_2-N(R^3R^4)$, $R^1=R^2=C_8-C_{22}$ alkyl, $X=O$; $R^3=CH_3$, $R^4=-C(=O)-spermine$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$; $R^4=H$, $q=1-3$, $y=1$; or $Z=(CH_2)_q$ $W^1=W^2=CH_2-N(R^3R^4)$, $R^1=R^2=C_8-C_{22}$ alkyl, $X=O$; $R^3=CH_3$; $R^4=CH_2(CH_2)_m-NH_2$; $m=1-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$; $R^4=CH_2(CH_2)_m-NH-C(=O)-spermine$; $m=1-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$; $R^4=CH_2(CH_2)_m-NH(C=O)-amino$ acid side chain; $m=1-6$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$; $R^4=(CH_2)_m(CH-OH)(CH_2)_m-NH_2$, $q=1-3$, $y=1$; or $Z=(CH_2)_q$, $W^1=W^2=CH_2-N(R^3R^4)$, $R^1=R^2=C_8-C_{22}$ alkyl, $X=O$; $R^3=CH_3$; $R^4=CH_2(CH_2)_n-NH_2$, $q=1-3$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)n-NH_2$, $n=0-6$, $q=1-3$, $y=1$; or $Z=(CH_2)_p-N(R^3)-(CH_2)_p$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)n-OH$, $n=0-6$, $q=1-3$, $y=1$; or $Z=(CH_2)_q-N(R^3)-(CH_2)_q$, $W1=W^2=CH_2-N(R^3R^4)$, $R^1=^2=C_8-C_{22}$ alkyl, $X=O$; $R^3=CH_3$, $R^4=-C(=O)-C(OH)-CH_2-(CH_2)n-NH_2$, $n=0-6$, $q=1-3$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH-iso-butyl)-CH_2-(CH_2)n-O-iso-butyl$, $n=0-6$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)n-C(=NH)-NH_2$, $n=0-6$, $q=1-3$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)n-His$, $n=0-6$, $q=1-3$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$, $R^4=-C(=O)-spermine$, $q=1-3$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$; $R^4=H$, $q=1-3$, $y=1$; or $Z=(CH_2)_q-N(R^3)-(CH_2)_q$, $W^1=W^2=CH_2-N(R^3R^4)$, $R^1=R^2=C_8-C_{22}$ alkyl, $X=O$; $R^3=CH_3$; $R^4=CH_2(CH_2)_m-NH_2$; $m=1-6$, $q=1-3$, $y=1$; or Z=(CH$_2$)$_q$—N(R$^3$)—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH—C(=O)-spermine; m=1-6, q=1-3, y=1; or Z=(CH$_2$)$_q$—N(R$^3$)—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH(C=O)-amino acid side chain; m=1-6, q=1-3, y=1; or Z=(CH$_2$)$_q$—N(R$^3$)—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=(CH$_2$)$_m$(CH—OH)(CH$_2$)$_m$—NH$_2$, q=1-3, y=1; or Z=(CH$_2$)$_q$—N(R$^3$)—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_n$—NH$_2$, q=1-3, y=1; or Z=(CH$_2$)$_q$—S—S—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$—NH$_2$, n=0-6, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$—OH, n=0-6, q=1-3, y=1; or Z=(CH$_2$)$_q$—S—S(CH$_2$)$_q$, W1 W$^2$=CH$_2$—N(R$^3$R$^4$), R$^1$=$^2$=C$_8$-C$_{22}$ alkyl, X=O; R$^3$=CH$_3$, R$^4$=—C(=O)—C(OH)—CH$_2$—(CH$_2$)$_n$—NH$_2$, n=0-6, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH-iso-buty)-CH$_2$—(CH$_2$)$_n$—O-iso-buty, n=0-6, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$—C(=NH)—NH$_2$, n=0-6, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$-His, n=0-6, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)-spermine, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=H, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=CH$_2$(CH$_2$)$_m$—NH$_2$; m=1-6, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=CH$_2$(CH$_2$)$_m$—NH—C(=O)-spermine; m=1-6, q=1-3, y=1; or Z=(CH$_2$)$_q$—S—S(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=CH$_2$(CH$_2$)$_m$—NH—C(=O)-amino acid side chain; m=1-6, q=1-3, y=1; or Z=(CH$_2$)$_q$—S—S—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=(CH$_2$)$_m$(CH—OH)(CH$_2$)$_m$—NH$_2$, q=1-3, y=1; or Z=(CH$_2$)$_q$—S—S—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_n$—NH$_2$, q=1-3, y=1; or Z=(CH$_2$)$_q$ W$^1$=W$^2$=CH$_2$—N(R$^3$R$^4$), R$^1$=R$^2$=C$_8$-C$_{22}$ alkyl, X=O; R$^3$=CH$_3$; R$^4$=COCH$_2$(OCH$_2$CH$_2$)$_m$—NH$_2$; m=1-6, q=1-3, y=0 or 1; or Z=(CH$_2$)$_q$—S—S—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=COCH$_2$(OCH$_2$CH$_2$)$_m$—NH$_2$; m=1-6, q=1-3, y=1; or Z=(CH$_2$)$_q$—N(R$^3$)—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=COCH$_2$(OCH$_2$CH$_2$)$_m$—NH$_2$; m=1-6, q=1-3, y=1; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)n-NH$_2$, n=0-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)n-OH, n=0-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(OH)—CH$_2$—(CH$_2$)n-NH$_2$, n=0-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH-iso-butyl)-CH$_2$—(CH$_2$)$_n$—O-iso-butyl, n=0-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)$_n$—C(=NH)—NH$_2$, n=0-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)n-His, n=0-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)-spermine, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=H, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH$_2$; m=1-6, y=0; or W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH—C(=O)-spermine; m=1-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH—(C=O)-amino acid side chain; m=1-6, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=(CH$_2$)$_m$(CH—OH)(CH$_2$)$_m$—NH$_2$, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)n-NH$_2$, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=H W$^2$=—CH$_2$—B—CH$_2$—N(R$^3$R$^4$)CH$_2$—R$^5$; R$^3$=R$^4$=CH$_3$; R$^5$=H, y=0 where B is selected from the group —O(CH$_2$)$_i$, —S(CH$_2$)$_i$, —S—S(CH$_2$)$_i$, —SO$_2$—(CH$_2$)$_i$, i=1-5; or W$^1$=H; W$^2$=CH$_2$—O—P(=O)(OMe)-O—CH$_2$CH$_2$—NH—C(=O)-spermine, y=0; or W$^1$=H; W$^2$=CH$_2$—O—P(=O)(OMe)-O—CH$_2$CH$_2$—NH—C(=O)-amino acid side chain, y=0; or W$^1$=H; W$^2$=CH$_2$—O—P(=O)(OMe)-O—CH$_2$CH$_2$—N$^+$(CH$_3$)$_3$Cl, y=0; or $W^1$=H; $W^2$=CH$_2$—O—P(=O)(O$^-$)—O—CH$_2$CH$_2$—NH—C(=O)-spermine, y=0; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)n-NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)n-OH, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, W1=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(OH)—CH$_2$—(CH$_2$)n-NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH-iso-butyl)-CH$_2$—(CH$_2$)$_n$—O-iso-butyl, n=0-6, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)$_n$—C(=NH)—NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)$_n$—His, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$ $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)-spermine, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=H, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$ $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_m$—NH$_2$; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_m$—NH—C(=O)-spermine; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_m$—NH—(C=O)-amino acid side chain; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=(CH$_2$)$_m$(CH—OH)(CH$_2$)$_m$—NH$_2$, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_n$—NH$_2$, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)n-NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_p$—N(R$^3$)—(CH$_2$)$_p$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)n-OH, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, W1=W$^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(OH)—CH$_2$—(CH$_2$)n-NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH-iso-butyl)-CH$_2$—(CH$_2$)n-O-iso-butyl, n=0-6, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)n-C(=NH)—NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)—C(NH$_2$)—CH$_2$—(CH$_2$)n-His, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$, $R^4$=—C(=O)-spermine, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=H, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_m$—NH$_2$; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_m$—NH—C(=O)-spermine; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=CH$_2$(CH$_2$)$_m$—NH—(C=O)-amino acid side chain; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$; $R^4$=(CH$_2$)$_m$(CH—OH)(CH$_2$)$_m$—NH$_2$, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, $W^1$=$W^2$=—CH2-B—CH$_2$—N(R$^3$R$^4$), $R^1$=$R^2$=C$_8$-C$_{22}$ alkyl, X=O; $R^3$=CH$_3$;

$R^4$=CH$_2$(CH$_2$)$_n$—NH$_2$, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5;

Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)$_n$—NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)$_n$—OH, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W1=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(OH)—CH$_2$—(CH$_2$)$_n$—NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH-iso-butyl)-CH$_2$—(CH$_2$)$_n$—O-iso-butyl, n=0-6, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)$_n$—C(=NH)—NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)—C(NH$_2$)—CH$_2$—(CH$_2$)$_n$-His, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$, R$^4$=—C(=O)-spermine, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=H, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH$_2$; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH—C(=O)-spermine; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH—(C=O)-amino acid side chain; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=(CH$_2$)$_m$(CH—OH)(CH$_2$)$_m$—NH$_2$, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_n$—NH$_2$, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$ W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=COCH$_2$(OCH$_2$CH$_2$)$_m$—NH$_2$; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—S—S—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=COCH$_2$(OCH$_2$CH$_2$)$_m$—NH$_2$; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—N(R$^3$)—(CH$_2$)$_q$, W$^1$=W$^2$=—CH2-B—CH$_2$—N(R$^3$R$^4$), R$^1$=R$^2$=C$_8$-C$_{22}$ alkyl, X=O; R$^3$=CH$_3$; R$^4$=COCH$_2$(OCH$_2$CH$_2$)$_m$—NH$_2$; m=1-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$—NH$_2$, n=0-6, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$—OH, n=0-6, q=1-3, y=1; or Z=(CH$_2$)$_q$—O—(CH$_2$)$_q$, W1 W$^2$=CH$_2$—N(R$^3$R$^4$), R$^1$=$^2$=C$_8$-C$_{22}$ alkyl, X=O; R$^3$=CH$_3$, R$^4$=—C(=O)—C(H)—CH$_2$—(CH$_2$)$_n$—NH$_2$, n=0-6, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH-iso-butyl)-CH$_2$—(CH$_2$)$_n$—O-iso-butyl, n=0-6, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$—C(=NH)—NH$_2$, n=0-6, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)—C(NH$_2$)—CH$_2$—(CH$_2$)$_n$-His, n=0-6, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$, R$^4$=—C(=O)-spermine, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=H, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=CH$_2$(CH$_2$)$_m$—NH$_2$; m=1-6, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=CH$_2$(CH$_2$)$_m$—NH—C(=O)-spermine; m=1-6, q=1-3, y=1; or Z=(CH$_2$)$_q$—O—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=CH$_2$(CH$_2$)$_m$—NH—(C=O)-amino acid side chain; m=1-6, q=1-3, y=1; or Z=(CH$_2$)$_q$—O—(CH$_2$)$_q$, W$^1$=W$^2$=CH$_2$—N(R$^3$R$^4$), R$^1$=R$^2$=C$_8$-C$_{22}$ alkyl, X=O; R$^3$=CH$_3$; R$^4$=(CH$_2$)$_m$(CH—OH)(CH$_2$)$_m$—NH$_2$, q=1-3, y=1; or Z=(CH$_2$)$_q$—O—(CH$_2$)$_q$, W$^1$=W$^2$=CH$_2$—N(R$^3$R$^4$), R$^1$=$^2$=C$_8$-C$_{22}$ alkyl, X=O; R$^3$=CH$_3$; R$^4$=CH$_2$(CH$_2$)$_n$—NH$_2$, q=1-3, y=1; or Z=(CH$_2$)$_q$—O—(CH$_2$)$_q$, W$^1$=W$^2$=—CH2-B—CH$_2$—N(R$^3$R$^4$), R$^1$=$^2$=C$_8$-C$_{22}$ alkyl, X=O; R$^3$=CH$_3$, R$^4$=—C(=O)—C(NH$_2$)$_n$—CH$_2$—(CH$_2$)$_n$—NH$_2$, n=0-6, q=1-3, y=1 where B is selected from the group —O(CH$_2$)$_i$, —S(CH$_2$)$_i$, —S—S(CH$_2$)$_i$, —SO$_2$—(CH$_2$)$_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-OH$, n=0-6, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W1=W^2=-CH2-B-CH_2-N(R^3R^4)$, $R^1=R^2=C_8-C_{22}$ alkyl, $X=O$; $R^3=CH_3$, $R^4=-C(=O)-C(OH)-CH_2-(CH_2)_n-NH_2$, n=0-6, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$, $R^4=-C(=O)-C(NH-iso-butyl)-CH_2-(CH_2)_n-O-iso-butyl$, n=0-6, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-C(=NH)-NH_2$, n=0-6, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n$-His, n=0-6, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$, $R^4=-C(=O)$-spermine, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$; $R^4=-H$, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$; $R^4=CH_2(CH_2)_m-NH_2$; m=1-6, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$; $R^4=CH_2(CH_2)_m-NH-C(=O)$-spermine; m=1-6, q=1-3, y=1 where B is selected from the group $-O(CH_2)_i$, $-S(CH_2)_i$, $-S-S(CH_2)_i$, $-SO_2-(CH_2)_i$, i=1-5; or $Z=(CH_2)_q-O-(CH_2)_q$, $W^1=W^2=-CH2-B-CH_2-N(R^3R^4)$, $R^1=R^2=C_8-C_{22}$ alkyl, $X=O$; $R^3=CH_3$; $R^4=CH_2(CH_2)_m-NH-(C=O)$-amino acid side chain; m=1-6, q=1-3, y=1 where B is selected from the group $-O(CH_2)_i$, $-S(CH_2)_i$, $-S-S(CH_2)_i$, $-SO_2-(CH_2)_i$, i=1-5.

In some embodiments, the compound of Formula I is a compound where:

$R^1=R^2=C_8-C_{22}$ alkyl, $X=O$, $W^1=H$; $W^2=CH_2-O-P(=O)(OMe)-O-CH_2CH_2-NH-C(=O)$-spermine, y=0;

$W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-C(=NH)-NH_2$, n=0-6, y=0;

$W^1=W^2=CH_2-N(R^3R^4)$, $R^2=C_8-C_{22}$ alkyl, $X=O$; $R^3=CH_3$, $R^4=-C(=O)$-spermine, y=0;

$W^1=W^2=CH_2-N(R^3R^4)$, $R^2=C_8-C_{22}$ alkyl, $X=O$; $R^3=CH_3$, $R^4=-C(=O)-C(NH_2)-CH_2-(CH_2)_n-NH_2$, n=0-6, y=0; or $W^1=W^2=CH_2-N(R^3R^4)$, $R^2=C_8-C_{22}$ alkyl, $X=O$; $R^3=CH_3$; $R^4=(CH_2)_m(CH-OH)(CH_2)_m-NH_2$, y=0.

In other embodiments, the compound of Formula I is a compound where:

$R^1=R^2=C_8-C_{22}$ alkyl, $X=O$, $W^1=H$; $W^2=CH_2-O-P(=O)(OMe)-O-CH_2CH_2-NH-C(=O)$-spermine, y=0; or $W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-C(=NH)-NH_2$, n=0-6, y=0.

In other embodiments, the compound of Formula I is a compound where:

$W^1=W^2=CH_2-N(R^3R^4)$, $R^2=C_8-C_{22}$ alkyl, $X=O$; $R^3=CH_3$, $R^4=-C(=O)-C(NH_2)-CH_2-(CH_2)n-NH_2$, n=0-6, y=0; or $W^1=W^2=CH_2-N(R^3R^4)$, $R^2=C_8-C_{22}$ alkyl, $X=O$; $R^3=CH_3$; $R^4=(CH_2)_m(CH-OH)(CH_2)_m-NH_2$, y=0.

In other embodiments, the compound of Formula I is a compound where:

$R^1=R^2=C_8-C_{22}$ alkyl, $X=O$, $W^1=H$; $W^2=CH_2-O-P(=O)(OMe)-O-CH_2CH_2-NH-C(=O)$-spermine, y=0;

$W^1=W^2=CH_2-N(R^3R^4)$, $R^1=R^2=C_8-C_{22}$ alkyl, $X=O$; $R^3=CH_3$, $R^4=-C(=O)-C(NH_2)-CH_2-(CH_2)_n-C(=NH)-NH_2$, n=0-6, y=0; or $W^1=W^2=CH_2-N(R^3R^4)$, $R^2=C_8-C_{22}$ alkyl, $X=O$; $R^3=CH_3$, $R^4=-C(=O)$-spermine, y=0.

In some embodiments, the transfection agent comprises at least one or more cationic lipid from Formula I and may optionally also contain one or more neutral lipids; DOPE, DPhPE, saturated and unsaturated DPPE, saturated and unsaturated DMPE, cholesterol, DOPC, Lyso-PE (1-acyl-2-hydroxy-sn-glycero-3-phosphoethanolamine), Lyso-PC (1-acyl-3-hydroxy-sn-glycero-3-phosphocholine), 3-alkyloxy-2-hydroxy-1-acetamidopropane, 4-alkyloxy-3-hydroxy-1-acetamidopropane, 5-alkyloxy-4-hydroxy-1-acetamidopropane or 6-alkyloxy-5-hydroxy-1-acetamidopropane. In some embodiments, the alkyloxy in the above list is selected from the group consisting of myristyloxy, myristeleyloxy lauryloxy, palmityloxy, palmitoleyloxy, oleyloxy and streayloxy. In some embodiments transfection agents contains Lyso-phosphatidylcholine, Sphingomyelin, Disaturated phosphatidylcholine, saturated and unsaturated Phosphatidylcholine, Disaturated phosphatidylethanolamine, Phosphatidylethanolamine saturated and unsaturated, Phosphatidylserine, phosphatidylinositol, Lyso-bis phosphatidic acid, Cholesterol, and Diglyceride. Helper Lipids may include, complete exosomes solutions, total extract of lipids isolated from exosomes.

In other embodiment, the transfection agent comprises at least one or more cationic lipid of Formula I. In certain embodiments, the transfection agent optionally comprises one or more of cationic lipid, while in other embodiments, the agent optionally comprises one or more neutral lipids or one or more exosomes, or lipid extract for exosomes. In certain embodiments, the transfection agent comprises both one or more cationic lipid and one or more neutral lipid.

In some embodiments, the cationic lipid is selected from the group consisting of GeneIn™ (MTI-GlobalStem), TransfeX™ (ATCC), LipofectAmine™ 2000, LipofectAmine 3000, LipofectAmine™, Lipofectin®, DMRIE-C, CellFectin® (Invitrogen), Oligofectamine® (Invitrogen), LipofectAce® (Invitrogen), Fugene® (Promega), Fugene® HD (Promega), Transfectam® (Promega), Tfx-10® (Promega), Tfx-20® (Promega), Tfx-50® (Promega), DNA-In (MTI-GlobalStem), Transfectin™ (BioRad, Hercules, Calif.), SilentFect™ (Bio-Rad), Effectene® (Qiagen, Valencia, Calif.), DC-chol (Avanti Polar Lipids), GenePorter® (Gene Therapy Systems, San Diego, Calif.), DharmaFect 1® (Dharmacon, Lafayette, Colo.), DharmaFect 2® (Dharmacon), DharmaFect 3® (Dharmacon), DharmaFect 4® (Dharmacon), Escort™ III (Sigma, St. Louis, Mo.), Escort™ IV (Sigma), ViaFect™ (Promega), DOTMA, DOTAP, DMRIE, DC-Chol, DDAB, DOSPA, DOSPER, DOGS, TMTPS, TMTOS, TMTLS, TMTMS, TMDOS, N-1-dimethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy)propane-1,3-diamine, N-1-dimethyl-N-1-(2,3-diamyristyloxypropyl)-2-(3-amino-2-hydroxypropyloxy)propane-1,3-diamine, N-1-dimethyl-N-1-(2,3-diapalmityloxypropyl)-2-(3-amino-2-hydroxypropyloxy)propane-1,3-diamine, L-spermine-5-carboxyl-3-(DL-,2-dipalmitoyl-dimethylaminopropyl-β-hydr-oxyethylamine, 3,5-(N,N-di-lysyl)-diaminobenzoyl-glycyl-3-(DL-1,2-dipalmitoyl-di-methylaminopropyl-β-hydroxyethylamine), L-Lysine-bis(O,O'-oleoyl-β-hydroxyethyl)-amide dihydrochloride, L-Lysine-bis-(O,O'-palmitoyl-β-hydroxyethyl)amide dihydrochloride, 1,4-bis[(3-(3-aminopropyl)-alkylamino)-2-hydroxypropyl)piperazine, L-Lysine-bis-(O,O'-myristoyl-β-hydroxyethyl)amide dihydrochloride, L-Omithine-bis-(O,O'-myristoyl-β-hydroxyethyl)amide dihydrochloride, L-Omithine-bis-(O,O'-oleoyl-β-hydroxyethyl)amide dihydrochloride, 1,4-bis[(3-(3-aminopropyl)-oleylamino)-2-hydroxypropyl]piperazine, L-Ornithine-bis-(O,O'-palmitoyl-(3-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino)propyl]piperaz-ine, L-Arginine-bis-(O,O'-oleoyl-β-hydroxyethyl)amide dihydrochloride, bis[(3-(3-aminopropyl)-myristylamino)2-hydroxypropyl]piperazine, L-Arginine-bis-(O,O'-palmitoyl-3-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl]piperazine, Glycine-bis-(O,O'-palmitoyl-β-hydroxyethyl)amide dihydro-chloride, Sarcosine-bis-(O,O'-palmitoyl-β-hydroxyethyl)amide dihydrochloride, L-Histidine-bis-(O,O'-palmitoyl-β-hydroxyethyl)amide dihydrochloride, cholesteryl-3β-carboxyl-amidoethylenetrimethylammonium iodide, 1,4-bis[(3-myristylamino)propyl]-piperazine, 1-dimethylamino-3-trimethylammonio-DL-2-propyl-cholesteryl carboxylate iodide, cholesteryl-3β-carboxyamido-ethyleneamine, cholesteryl-3β-oxysuccinamidoethyl-enet-rimethylammonium iodide, 1-dimethylamino-3-trimethylammonio-DL-2-propyl-cholesteryl-3β-oxysuccinate iodide, 2-[(2-trimethylammonio)-ethylmethylamino] ethyl-cholesteryl-3β-oxysuccinate iodide, 3β[N—(N',N'-dimethylaminoethane)carbamoyl]-cholesterol, and 3β-[N-(polyethyleneimine)-carbamoyl] cholesterol, 1,4-bis[(3-palmitylamino)propyl]piperazine, L-Omithylglycyl-N-(1-heptadecyloctadecyl)glycin-amide, $N^2,N^5$-Bis(3-aminopropyl)-L-ornithylglycyl-N-(1-heptadecyloctadecyl)glycin-amide, 1,4-bis[(3-(3-amino-2-hydroxy-propyl)-alkylamino)-2-hydroxypropyl]piperazine $N^2$—[$N^2$,$N^5$-Bis(3-aminopropyl)-L-ornithyl]-N,N-dioctadecyl-L-glutamine, $N^2$—[$N^2$,$N^5$-Bis(aminopropyl)-L-ornithyl]-N—N-dioctadecyl-L-α-glutamine, 1,4-bis[(3-(3-amino-2-hydroxypropyl)-oleylamino)2-hydroxypropyl]piperazine, $N^2$—[$N^2$,$N^5$-Bis(aminopropyl)-L-ornithyl]-N—N-dioctadecyl-L-α-asparagine, N—[$N^2$—[$N^2$,$N^5$-Bis[(1,1-dimethylethoxy)-carbonyl]-$N^2$,$N^5$-bis[3-[(1,1-dimethylethoxy)carbonyl]aminopropyl]-L-ornithyl-N-dioctadecyl-L-glutaminyl]-glutamic acid, $N^2$—[$N^2$,$N^5$-Bis(3-aminopropyl)-L-ornithyl]-N,N-diolyl-L-glutamine, $N^2$—[$N^2$,$N^5$-Bis(aminopropyl)-L-ornithyl]-N—N-dioleyl-L-α-glutamine, 4-bis[(3-(3-amino-2-hydroxypropyl)-myristylamino)-2-hydroxypropyl]piperaz-ine, $N^2$—[$N^2$,$N^5$-Bis(aminopropyl)-L-ornithyl]-N—N-dioleyl-L-α-asparagine, N—[$N^2$—[$N^2$,$N^5$-Bis[(1,1-dimethylethoxy)carbonyl]-$N^2$,$N^5$-bis[3-[(1,1-dimethylethoxy)carbonyl]-aminopropyl]-L-ornithyl-N—N-dioleyl-L-glutaminyl]-L-glutamic acid, 1,4-bis[(3-(3-aminopropyl)-oleylamino)propyl]piperazine, $N^2$—[$N^2$,$N^5$-Bis(3-aminopropyl)-L-ornithyl]-N,N-dipalmityl-L-glutamine, $N^2$—[$N^2$,$N^5$-Bis(aminopropyl)-L-ornithyl]-N—N-dipalmityl-L-α-glutamine, $N^2$—[$N^2$,$N^5$-Bis(aminopropyl)-L-ornithyl]-N—N-dipalmityl-L-α-asparagine, N—[$N^2$—[$N^2$,$N^5$-Bis[(1,1-dimethylethoxy)-carbonyl]-$N^2$,$N^5$-bis[3-[(1,1-dimethylethoxy)-carbonyl] aminopropyl]-L-ornithyl-N—N-dipalmityl-L-glutaminyl]-L-glutamic acid, $N^2$—[$N^2$,$N^5$-Bis(3-aminopropyl)-L-ornithyl]-N,N-dimyristyl-L-glutamine, $N^2$—[$N^2$,$N^5$-Bis-(aminopropyl)-L-ornithyl]-N—N-dimyristyl-L-α-glutamine, $N^2$—[$N^2$,$N^5$-Bis(aminopropyl)-L-ornithyl]-N—N-dimyristyl-L-α-asparagine, 1,4-bis[(3-(3-amino-2-hydroxypropyl)-palmitylamino)-2-hydroxypropyl]piperazine, N—[$N^2$—[$N^2$,$N^5$-Bis[(1,1-dimethylethoxy)-carbonyl]-$N^2$,$N^5$-bis[3-[(1,1-dimethylethoxy)carbonyl] aminopropyl]-L-ornithyl-N—N-dimyristyl-L-glutaminyl]-L-glutamic acid, 1,4-bis[(3-(3-aminopropyl)-myristylamino)-propyl]piperazine, $N^2$—[$N^2$,$N^5$-Bis(3-aminopropyl)-L-ornithyl]-N,N-dilaureyl-L-glutamine, $N^2$—[$N^2$,$N^5$-Bis(aminopropyl)-L-ornithyl]-N—N-dilaureyl-L-ca-glutamine, $N^2$—[$N^2$,$N^5$-Bis(aminopropyl)-L-ornithyl]-N—N-dilaureyl-L-α-asparagine, N—[$N^2$—[$N^2$,$N^5$-Bis[(1,1-dimethylethoxy)carbonyl]-$N^2$,$N^5$-bis[3-[(1,1-dimethylethoxy)carbonyl] amino-propyl]-L-ornithyl-N—N-dilaureyl-L-glutaminyl]-L-glutamic acid, 3-[N',N"-bis(2-tert-butyloxycarbonylaminoethyl)guanidino]-N,N-dioctadec-9-enylpropionamide, 3-[N',N"-bis(2-tertbutyloxycarbonylaminoethyl)guanidino]-N,N-dipalmitylpropionamide, 3-[N',N"-bis(2-tertbutyloxycarbonylaminoethyl)guanidino]-N,N-dimyristylpropionamide, 1,4-bis[(3-(3-aminopropyl)-palmitylamino)propyl]piperazine, 1,4-bis[(3-(3-amino-2-hydroxypropyl)-oleylamino)propyl]piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydoxypropyl)-myristylamino)propyl]piperazine, [(3-aminopropyl)-bis-(2-tetradecyloxyethyl)]methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylamino-propane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)->4-(3-amino-propyl-amino)-4-tetradecylcarbamoyl-butylcarbamic acid cholesteryl ester, (3-Amino-propyl)->4-(3-amino-propylamino-4-carbamoylbutylcarbamic acid cholesteryl ester, (3-Amino-propyl)->4-(3-amino-propylamino)-4-(2-dimethylamino-ethylcarbamoyl)-butylcarbamic acid cholesteryl ester, Spermine-5-carboxyglycine (N'-stearyl-N'-oleyl) amide tetratrifluoroacetic acid salt, Spermine-5-carboxyglycine (N'-stearyl-N'-elaidyl) amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino)-propyl]piperazine, N-(3-aminopropyl)-N,N'-bis-(dodecyloxyethyl)-piperazinium bromide, N-(3-aminopropyl)-N,N'-bis-(oleyloxyethyl)-piperazinium bromide, N-(3-aminopropyl)-N,N'-bis-(palmityloxyethyl)-piperazinium bromide, N-(3-aminopropyl)-N,N'-bis-(myristyloxyethyl)-piperazinium bromide, N-(3-aminopropyl)-N'-methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'-methyl-N,N'-(bis-2-palmityloxyethyl)-piperazinium bromide, N-(3-aminopropyl)-N'-methyl-N,N'-(bis-2-myristyloxyethyl)-piperazinium bromide, 1,4-bis[(3-(3-aminopropyl)-oleylamino)-2-hydroxy-propyl]piperazine, 1,4-bis[(3-(3-aminopropyl)-myristylamino)-2-hydroxy-propyl]piperazine, or 1,4-bis[(3-(3-aminopropyl)-palmitylamino)-2-hydroxy-propyl]piperazine, 3-alkyloxy-2-hydroxy-1-histidylamidopropane, 3-alkyloxy-2-hydroxy-1-aminopropane, 4-alkyloxy-3-hydroxy-1-histidylamidopropane, 4-alkyloxy-3-hydroxy-1-aminopropane, 5-alkyloxy-4-hydroxy-1-histidylamidopropane, 5-alkyloxy-4-hydroxy-1-aminopropane, 6-alkyloxy-5-hydroxy-1-histidylamidopropane, 6-alkyloxy-4-hydroxy-1-aminopropane; 2,3-dialkoxy-1,4-bis(N-methyl-N-carboxyspermineamido)-aminobutane, 2,3-dialkoxy-1,4-bis(N-methyl-N-histidinylamido)aminobutane, 2,3-dialkoxy-1,4-bis(N-methyl-N-arginylamido)aminobutane, 2,3-dialkoxy-1,4-bis(N-methyl-N-lysinylamido)aminobutane, 2,3-dialkoxy-1,4-bis(N-methyl-N'-ornithinyl-amido)aminobutane, 2,3-dialkoxy-1,4-bis(N-methyl-N-serinylamido)aminobutane, 2,3-dialkoxy-1,4-bis(N-methyl-N-homoerinylamido)aminobutane, 2,3-dialkoxy-1,4-bis(N-methyl-N-(diaminobutanyl)amido)aminobutane, 2,3-dialkoxy-1,4-bis(N-methyl-N-(di-aminopropyl)amido)aminobutane, 2,3-dialkoxy-1,4-bis(N-methyl-N-(2-hydroxylpropyl-amine))aminobutane, 2,3-dialkoxy-1,4-bis(N-methyl-N-(2-diaminopropyl))aminobutane, 2,3-dialkoxy-1,4- and bis(N-methyl-N-propylamine)aminobutane. The alkoxy in the above list may be myristyloxy, myristeleyloxy lauryloxy, palmityloxy, palmitoleyloxy, oleyloxy and streayloxy.

In some embodiments transfection agents contains lyso-phosphatidylcholine, sphingomyelin, disaturated phosphatidylcholine, saturated and unsaturated phosphatidylcholine, disaturated phosphatidylethanolamine, phosphatidylethanolamine saturated and unsaturated, phosphatidylserine, phosphatidylinositol, lyso-bis phosphatidic acid, cholesterol, and diglyceride. Helper Lipids may include, complete exosomes solutions, total extract of lipids isolated from exosomes. The Helper lipids can be formulated into exosome like lipid particles so that lyso-phosphatidylcholine is from 3.75 to 6.21% of total lipid content, a sphingomyelin, a sphingosin, or ceramide is from 8.26 to 12, 41% of total, phosphatidylcholine-disaturated is from 3.00 to 4.81% of total, Phosphatidylethanolamine-mix is from 12.00 to 19.22%, phosphatidylserine is from 5.17 to 6.89%, phosphatidylinositol is from 5.17 to 6.89%, Phosphatidylethanolamine disaturated is from 2.61 to 2.85%, Phosphatidylethanolamine mix is from 13.42 to 14.65%, cholesterol is from 13.01 to 16.61%, diglycerides are from 4.76 to 7.05% and cationic lipids can be the remaining % in such formulations. Cationic lipids can be substituted or used in combination with a sphingomyelin, a sphingosin, or ceramides. Depending on cell type the % composition of helper lipids and can be adjusted to optimize formulations of synthetic exosomes with various transfection enhancers.

When the composition contains a neutral lipid, that lipid a saturated or unsaturated, or mixed acyl phosphatidyl ethanol mine (PE) or phosphatidyl choline (PC), for example, DOPE, DPhPE, saturated and unsaturated DPPE, saturated and unsaturated DMPE, cholesterol, DOPC, Lyso-PE (1-acyl-2-hydroxy-sn-glycero-3-phosphoethanolamine), Lyso-PC (1-acyl-3-hydroxy-sn-glycero-3-phosphocholine), 3-alkyloxy-2-hydroxy-1-acetamidopropane, 4-alkyloxy-3-hydroxy-1-acetamidopropane, 5-alkyloxy-4-hydroxy-1-acetamidopropane or 6-alkyloxy-5-hydroxy-1-acetamidopropane. The alkyloxy in the above list may be myristyloxy, myristeleyloxy lauryloxy, palmityloxy, palmitoleyloxy, oleyloxy or streayloxy. In some embodiments, the transfection agent. may contain more than one of these neutral lipids or exosomes, lipids from exosomes or total lipid extracts from exosomes compositions.

In other embodiments the transfection agent comprises at least one polyamine moiety. Suitable polyamines include dense star dendrimers, PAMAM dendrimers, $NH_3$ core dendrimers, ethylenediamine core dendrimers, dendrimers of generation 5 or higher, dendrimers with substituted groups, dendrimers having one or more amino acids, grafted dendrimers, activated dendrimers, polyethylenimine, and polyethylenimine conjugates, polycationic peptides such as polylysine, polyornithine, polyhistidine, polyarginine In other embodiments, cell surface ligand containing adhesion peptide sequences is conjugated to a nucleic acid binding group. In some of these embodiments, the nucleic acid binding group is linked to a polyamine or peptide nucleic acid. The polyamine optionally comprises at least one spermine moiety.

Suitable cell surface ligands containing adhesion peptide sequences that are derived from cell adhesion proteins include, but are not limited to, a sequence selected from the group consisting of SEQ ID NOs:202-503, as set forth in Table 1, below, or in the sequence listings.

In some embodiments, the peptides of SEQ ID NOs:202-503 are optionally linked to a nucleic acid binding moiety, a helper lipid, a cationic lipid, a cationic polymer, a GPI anchor peptide or other chemical moieties that associate with transfection complexes.

In some embodiments, the peptides of SEQ ID NOs:202-500 are used with other surface ligands, such as antibodies, antibody fragments, single chain antibodies, aptemers, or peptides from phage display. In certain embodiments, these surface ligands are optionally attached to nucleic acid binding moieties, to lipids or lipid associating moieties.

In particular embodiments, the transfection agent comprises at least one cationic lipid, and optionally also contains in various combinations with one or more neutral and/or helper lipids, targeting moieties, cell penetration agent, fusion agents, and lysomotropic agents.

In some embodiments, the presently disclosed complexes comprise one more agents selected from the group consisting of fusogenic agents, nuclear localization sequences, cell penetration agent, transport peptides, receptor-ligand or cell adhesion peptides.

It is to be understood that while some peptides are disclosed herein in the context of one particular use, all of the peptides presently disclosed can be used in other uses as well. Thus, by way of example only, the peptides of SEQ ID NOs:1-41 are disclosed to be nuclear localization peptides. However, these peptides can be used as a nucleic acid binding peptide, a nucleic acid condensing peptide, a transfection enhancer.

In specific embodiments, the cell surface ligand containing adhesion peptide sequences is covalently linked to the transfection agents, the cationic lipid, the neutral lipid, helper lipid, a chemical group that associates with lipids or liposomes, and/or the polyamine.

In specific embodiments, the plant virus movement protein or peptide derived from plant virus movement proteins is covalently linked to the transfection agents, the cationic lipid, the neutral lipid, helper lipid, a chemical group that associates with lipids or liposomes, and/or the polyamine.

In other embodiments, the plant virus movement protein or peptide derived from plant virus movement proteins is conjugated to a nucleic acid binding group. In some of these embodiments, the nucleic acid binding group is linked to a polyamine or peptide nucleic acid. The polyamine optionally comprises at least one spermine moiety.

Suitable virus movement proteins and peptides derived from plant virus movement proteins sequences include, but are not limited to, a sequence selected from the group consisting of SEQ ID NOs:506-580, as set forth in Table 1, below, or in the sequence listings.

In some embodiments, the peptides of SEQ ID NOs:506-580 are optionally linked to a nucleic acid binding moiety, a helper lipid, a cationic lipid, a cationic polymer, a GPI anchor peptide or other chemical moieties that associate with transfection complexes.

In some embodiments, the peptides of SEQ ID NOs:506-580 are used with other surface ligands, such as antibodies, antibody fragments, single chain antibodies, aptamers, or peptides from phage display. In certain embodiments, these surface ligands are optionally attached to nucleic acid binding moieties, to lipids or lipid associating moieties.

In particular embodiments, the transfection agent comprises at least one cationic lipid, and optionally also contains in various combinations with one or more neutral and/or helper lipids, targeting moieties, surface ligand, fusion agents, and lysomotropic agents.

In some embodiments, the presently disclosed complexes comprise one more agents selected from the group consisting of fusogenic agents, cell penetration agents, nuclear localization sequences, transport peptides, plant movement protein or peptide derived from, receptor-ligand, surface ligand or cell adhesion peptides.

It is to be understood that while some peptides are disclosed herein in the context of one particular use, all of the peptides presently disclosed can be used in other uses as well. Thus, by way of example only, the peptides of SEQ ID NOs:1-41 are disclosed to be nuclear localization peptides. However, these peptides can be used as a nucleic acid binding peptide, a nucleic acid condensing peptide, a transfection enhancer.

In another aspect, disclosed herein are pharmaceutical compositions containing a complex as described herein, and a pharmaceutically acceptable carrier.

In another aspect, disclosed herein are methods of transfecting a cell, by contacting a cell with a complex as described herein. In some embodiments, the cell is selected from the group consisting of a primary cell culture, a passaged cell culture, suspension cell line and an attached cell line. Suitable cells include all human cell lines and all animal cell lines. In some embodiments, the cell is a blood derived cell or the cell is a stem cell, while in other embodiments, the cell is a neuron.

In one method, a nucleic acid, protein or, peptide, or pharmaceutical is contacted with a cell surface ligand containing adhesion peptide, the plant virus movement protein, or peptide derived therefrom, capable associating with nucleic acid, protein, peptide or pharmaceutical and the resulting mixture is added to a transfection agent then contacted to cells.

In one embodiment of the transfection methods, cell surface ligand containing adhesion peptide, the plant virus movement protein, or peptide derived therefrom, are contacted with a transfection agent capable of associating with a nucleic acid, a protein, a peptide or a pharmaceutical composition, followed by addition of a nucleic acid, a protein, peptide or pharmaceutical then contacted to cells.

In another method, cell surface ligand containing adhesion peptide, the plant virus movement protein, or peptide derived therefrom, linked to a nucleic acid binding moiety is contacted with transfection agent capable of associating with nucleic acid, protein, peptide or pharmaceutical followed by addition of a nucleic acid, protein, peptide or pharmaceutical then contacted to cells In another method, cell surface ligand containing adhesion peptide, the plant virus movement protein, or peptide derived therefrom, contacted with transfection agent followed by addition of a fusion agent and then contacted with a nucleic acid, protein, peptide or pharmaceutical then contacted to cells In another method, cell surface ligand containing adhesion peptide, the plant virus movement protein, or peptide derived therefrom, linked to a nucleic acid binding moiety is contacted with transfection agent followed by addition of a fusion agent and then contacted with a nucleic acid, protein, peptide or pharmaceutical then contacted to cells In another method cell surface ligand containing adhesion peptide, the plant virus movement protein, or peptide derived therefrom, is contacted with a fusion agent followed by addition of a transfection agent and then contacted with a nucleic acid, protein, peptide or pharmaceutical then contacted to cells.

In another method cell surface ligand containing adhesion peptide, the plant virus movement protein, or peptide derived therefrom, linked to a nucleic acid binding moiety is contacted with a fusion agent followed by addition of a transfection agent and then contacted with a nucleic acid, protein, peptide or pharmaceutical then contacted to cells.

In another method cell surface ligand containing adhesion peptide, the plant virus movement protein, or peptide derived therefrom, linked to a nucleic acid binding moiety is contacted with a transfection agent, then contacted with a nucleic acid, protein, peptide or pharmaceutical, then contacted with a fusion agent, and then contacted to cells.

In another method cell surface ligand containing adhesion peptide, the plant virus movement protein, or peptide derived therefrom, linked to a nucleic acid binding moiety is contacted with a transfection agent containing exosomes, or lipid extracts from exosomes, then contacted with a nucleic acid, protein, peptide or pharmaceutical, then contacted with a fusion agent, and then contacted to cells In another method an aqueous solution of transfection enhancers, that may optionally contain one or more a plant virus movement proteins or peptides derived from plant virus movement proteins linked to a nucleic acid binding moiety, that may optionally contain buffers, that may optionally contain one or more cell surface ligands, that may optionally contain one or more nuclear localization agents, that may optionally contain one or more cell penetration peptides, that may optionally containing one or more fusion peptides or proteins, all or some of these transfection enhancers may optionally be linked to nucleic acid binding domain is mixed with an ethanol or aqueous solution of lipids that may contain cationic lipids, helper lipids, exosomes or total lipid extracts of exosomes or various mixtures of such lipids or lipid particles The mixture is then contacted with nucleic acids, protein, peptides, exosomes, growth enhancers, and then cells.

In another method an ethanol solution of transfection enhancers, that may optionally contain one or more a plant virus movement proteins or peptides derived from plant virus movement proteins linked to a nucleic acid binding moiety, that may optionally contain buffers, that may optionally contain one or more cell surface ligands, that may optionally contain one or more nuclear localization agents, that may optionally contain one or more cell penetration peptides, that may optionally containing one or more fusion peptides or proteins, all or some of these transfection enhancers may optionally be linked to nucleic acid binding domain is mixed with an ethanol or aqueous solution of lipids that may contain cationic lipids, helper lipids, exosomes or total lipid extracts of exosomes or various mixtures of such lipids or lipid particles The mixture is then contacted with nucleic acids, protein, peptides, exosomes, growth enhancers, and then cells.

In another method an aqueous solution of transfection enhancers, that may optionally contain one or more a plant virus movement proteins or peptides derived from plant virus movement proteins linked to a nucleic acid binding moiety, that may optionally contain buffers, that may optionally containing one or more cell surface ligands, that may optionally one or more nuclear localization agents, that may optionally contain one or more cell penetration peptides, all or some of these transfection enhancers may optionally be linked to nucleic acid binding domain is mixed with an ethanol or aqueous solution of lipids that may contain cationic lipids, helper lipids, exosomes or total lipid extracts of exosomes or various mixtures of such lipids or lipid particles. This mixture is then contacted with one or more fusion peptides or proteins which may optionally be in a buffer. The mixture is then contacted with nucleic acids, protein, peptides, exosomes, growth enhancers, and then cells.

In another method, a transfection complex is contacted with a nucleic acid, protein or, peptide then contacted with cell surface ligand containing adhesion peptide, the plant virus movement protein, or peptide derived therefrom, and then contacted to cells.

Those skilled in the art understand that concentrations of the various components, such as cationic lipid, helper lipid, the plant virus protein or peptide derived therefrom, cell surface ligand, fusogenic reagent, nuclear ligand, cationic polymer, condensing agent, cell penetration, lysomotrophic agent, exosomes or exosome lipids or proteins from exosomes, peptides derived for exosomal proteins and transfection enhancers are optimized according to the cell to be transfected or the in vivo application. In some embodiments, the concentration of each component ranges from 0.001 to 20 mg/mL, depending on solubility and formulation solvent.

In some embodiments, the plant virus movement protein derived peptides disclosed herein are suitable for use in the disclosed transfection enhancers to enhance transfection into HeLa cells, HuVec cells, iPS cells, NL-1 cells, C2Cl2 cells, human fibroblast cells, stem cells, Jurkat cells, rat cortical neurons, THP-1 cells, and human skeletal muscle cells, among others.

In some embodiments, the peptide useful to enhance the transfection of HeLa cells is selected from the group consisting of SEQ ID NOs: 107, 205, 216, 218, 219, 220, 224, 226, 229, 230, 234, 236, 236, 237, 238, 239, 256, 268, 323, 326, 327, 328, 332, 335, 336, 338, 341, 342, 343, 344, 345, 347, 348, 349, 350, 351, 352, 353, 354, 355, 357, 358, 359, 360, 361, 363, 365, 367, 369, 371, 373, 375, 377, 379, 381, 383, 450, 452, 454, and 503 can be used in combination with the plant virus movement protein or peptide derived therefrom. In some of these embodiments, the peptide useful to enhance the transfection of HeLa cells is selected from the group consisting of SEQ ID NOs:205, 237, 268, 326, 328, 335, 336, 342, 347, 348, 352, 353, 355, 357, 358, 365, 367, 377, 379, 381, 450, 454, and 503 can be used in combination with the plant virus movement protein or peptide derived therefrom. In some embodiments, the peptide useful to enhance the transfection of HuVec cells is selected from the group consisting of SEQ ID NOs:205, 216, 218, 219, 220, 224, 226, 229, 230, 234, 236, 236, 237, 238, 239, 256, 268, 323, 326, 327, 328, 332, 335 336, 338, 341,342, 343,344, 345, 347, 348, 349, 350, 351,352, 353,354, 355, 357, 358, 359, 360, 361, 363, 365, 367, 369, 371, 373, 375, 377, 379, 381, 383, 450, 452, 454, and 503 can be used in combination with the cell surface ligand containing adhesion peptide, the plant virus movement protein, or peptide derived therefrom. In some of these embodiments, the peptide useful to enhance the transfection of HuVec cells is selected from the group consisting of SEQ ID NOs:236, 358, 373 can be used in combination with the cell surface ligand containing adhesion peptide, the plant virus movement protein, or peptide derived therefrom.

In some embodiments, the peptide useful to enhance the transfection of NL-1 iPS cells is selected from the group consisting of SEQ ID NOs:107, 205, 216, 218, 219, 220, 224, 226, 229, 230, 234, 236, 236, 237, 238, 239, 256, 268, 323, 326, 327, 328, 332, 335, 336, 338, 341, 342, 343, 344, 345, 347, 348, 349, 350, 351, 352, 353, 354, 355, 357, 358, 359, 360, 361, 363, 365, 367, 369, 371, 373, 375, 377, 379, 381, 383, 450, 452, 454, 503 can be used in combination with the cell surface ligand containing adhesion peptide, the plant virus movement protein, or peptide derived therefrom. In some of these embodiments, the peptide useful to enhance the transfection of NL-1 iPS cells is selected from the group consisting of SEQ ID NOs:216, 224, 226, 236, 236, 323, 327, 341, 343, 347, 348, 349, 350, 351, 354, 358, 360, 373, 383, 450, 454, 503 can be used in combination with the cell surface ligand containing adhesion peptide, the plant virus movement protein, or peptide derived therefrom.

In some embodiments, the peptide useful to enhance the transfection of C2Cl2 cells is selected from the group consisting of SEQ ID NOs:205, 216, 218, 219, 220, 224, 226, 229, 230, 234, 236, 236, 237, 238, 239, 256, 268, 323, 326, 327, 328, 332, 335, 336, 338, 341, 342, 343, 344, 345, 347, 348, 350, 351, 352, 353, 354, 355, 357, 358, 359, 360, 361, 363, 365, 367, 369, 371, 373, 375, 377, 379, 381, 383, 450, 452, 454, 501, 502, 503 can be used in combination with the cell surface ligand containing adhesion peptide, the plant virus movement protein, or peptide derived therefrom. In some of these embodiments, the peptide useful to enhance the transfection of C2Cl2 cells is selected from the group consisting of SEQ ID NOs:218, 230, 237, 239, 256, 323, 326, 328, 335, 336, 342, 343, 345, 347, 348, 352, 357, 359, 367, 375, 379, 381, 450, 452, 454, 501, 502, 503 can be used in combination with the cell surface ligand containing adhesion peptide, the plant virus movement protein, or peptide derived therefrom, In some embodiments, the peptide useful to enhance the transfection of human fibroblast cells is selected from the group consisting of SEQ ID NOs:205, 216, 218, 219, 220, 224, 226, 229, 230, 234, 236, 236, 237, 238, 239, 256, 268, 323, 326, 327, 328, 332, 335, 336, 338, 341, 342, 343, 344, 345, 347, 348, 349, 350, 351, 352, 353, 354, 355, 357, 358, 359, 360, 361, 363, 365, 367, 369, 371, 373, 375, 377, 379, 381, 383, 450, 452, 454, 501, 503 can be used in combination with cell surface ligand containing adhesion peptide, the plant virus movement protein, or peptide derived therefrom. In some of these embodiments, the peptide useful to enhance the transfection of human fibroblast cells is selected from the group consisting of SEQ ID NOs:205, 218, 219, 229, 230, 335, 336, 342, 344, 348, 349, 350, 351, 353, 355, 357, 361, 367, 369, 375, 379, 381, 450, 454, 501, 503 can be used in combination with the cell surface ligand containing adhesion peptide, the plant virus movement protein, or peptide derived therefrom.

In some embodiments, the peptide useful to enhance the transfection of Jurkat cells is selected from the group consisting of SEQ ID NOs:205, 216, 218, 219, 220, 224, 226, 229, 230, 234, 236, 236, 237, 238, 239, 256, 268, 323, 326, 327, 328, 332, 335, 336, 338, 341, 342, 343, 344, 345, 347, 348, 349, 350, 351, 352, 353, 354, 355, 357, 358, 359, 360, 361, 363, 365, 367, 369, 371, 373, 375, 377, 379, 381, 383, 450, 452, 454, 501, 503 can be used in combination with the cell surface ligand containing adhesion peptide, the plant virus movement protein, or peptide derived therefrom. In some of these embodiments, the peptide useful to enhance the transfection of Jurkat cells is selected from the group consisting of SEQ ID NOs:218, 349, 358 can be used in combination with the cell surface ligand containing adhesion peptide, the plant virus movement protein, or peptide derived therefrom.

In some embodiments, the peptide useful to enhance the transfection of rat cortical neuron cells is selected from the group consisting of SEQ ID NOs: 220, 236, 238, 323, 327, 336, 338, 341, 343, 347, 348, 350, 351, 352, 354, 367, 369, 373, 375, 377, 454 can be used in combination with the cell surface ligand containing adhesion peptide, the plant virus movement protein, or peptide derived therefrom.

In some embodiments, the peptide useful to enhance the transfection of THP-1 cells is selected from the group consisting of SEQ ID NOs:219, 229, 230, 239, 323, 328, 332, 341, 343, 350, 351, 357, 358, 375, 450, 454 can be used in combination with the cell surface ligand containing adhesion peptide, the plant virus movement protein, or peptide derived therefrom.

In some embodiments, the peptide useful to enhance the transfection of human skeletal muscle cells is selected from the group consisting of SEQ ID NOs: 218, 219, 230, 328, 336, 344, 350, 351, 353, 355, 365, 375 can be used in combination with the cell surface ligand containing adhesion peptide, the plant virus movement protein, or peptide derived therefrom.

In some embodiments combination of different surface ligands that have preference for a given cell types are mixed together to target multiple cell types in a single formulation.

In another aspect, disclosed herein are kits containing a transfection agent and a peptide or protein or a modified peptide or modified protein with cell surface ligand containing adhesion peptide, the plant virus movement protein, or peptide derived therefrom, as described herein. In some embodiments, the kit further comprises instructions for the preparation and the use of the transfection complexes. In certain embodiments, the kit further comprises separate compartments for the various components. In certain embodiments transfection agents may comprise various peptides selected from SEQ ID NOs 1-505 in combination with SEQ ID NOs 506-580 that are suitable for transfecting cells in vivo or in vitro.

EXAMPLES

Example 1: Surface Ligands

Cells were plated to so that on the day of transfection the cells were 70% confluent in 96 well tissue culture plates. A DOMTA/DOPE Lipid solution (1:1 molar ratio) at 2 mg/mL in water were mixed with an equal volume cell surface ligand containing adhesion peptide, the plant virus movement protein, or peptide derived therefrom, that had the nucleic acid binding moiety RRRRRRRRRRRR (SEQ ID NO: 109) or KKKKKKKKKKKKKKK (SEQ ID NO: 102) covalently linked to the N-terminus, or C-terminus of each peptide during peptide synthesis. Peptides were at 2 mg/mL in water. The DOTMA/DOPE and the solution containing the cell surface ligand containing adhesion peptide, the plant virus movement protein, or peptide derived therefrom, surface ligand peptide the was diluted 1 to 1 (v/v) in water. DOMTA/DOPE/PEPTIDE solutions were added to 0.1 mL of a plasmid DNA solution (EF1Alpha eGFP plasmid) at 10 µg/mL in OptiMEM.

All solutions were at room temperature. A volume of 0.2 mL of a 10 µg/mL solution of DNA was aliquoted into each well of a non-tissue cultured treated plate. 1-12 µL of transfection reagents were added to DNA solutions respectively. The transfection reagent and DNA solution was mixed by pipetting up and down twice. Transfection complexes were formed for 10 minutes. After 10 minutes, 0.01 or 0.02 mL of the transfection complex was added to cells. HuVEC, HeLa, human adult keratinocytes, human primary adult fibroblast, and A549 cells all respectively received 0.01 mL of the transfection complex. Human skeletal muscle cells, mouse C2Cl2 cells, and Jurkat, cells received 0.02 mL of the transfection complex. Cells were incubated for 42 hours at 37° C. at 5% $CO_2$. Plates were read on a fluorescent plate reader. Cells were also examined visually under a microscope to assess the extent of transfection (in terms of the percent of cells transfected) with a fluorescent microscope. Other modes of analysis, for example quantification with B-galactosidase or luciferase reports plasmids can also be used. If the plate reader did not show a sufficient signal to noise ratio, then plates were scored for cells transfected and those peptides that show increase over DOTMA alone were noted.

Not all surface ligands increased transfection efficiency even though they were suggested to be used to attach cell to tissue culture plates. Surface ligand that caused increase expression of GFP over the lipid DOTMA with no surface ligand were considered to enhance transfection or had higher % cells transfected were considered to enhance transfection. Peptides that gave greater than 2-fold enhancement are noted in bold and could be further optimized by adding different transfection enhancers or could be used with different cationic lipids or polymers.

Tables 2-7, below, provide the results of the transfection enhancements with the various cell types, while Table 8 lists the peptides that were determined by visual inspection to enhance the transfection of the denoted cell lines over the lipid DOTMA.

The following sequences increased transfection expression and the % cells transfected over the no peptide control on some examined cell types: SEQ ID NOs: 205, 216, 218, 219, 220, 226, 229, 230, 236, 237, 238, 239, 256, 268, 323, 326, 327, 328, 332, 336, 338, 341, 342, 343, 344, 345, 347, 348, 349, 350, 351, 352, 353, 354, 355, 357, 358, 359, 360, 361, 365, 367, 369, 373, 375, 377, 379, 381, 393, 450, 452, 454, 501, and 503.

Various DOTMA/peptide transfection reagents that showed enhanced transfection efficiency over DOTMA alone were further formulated with the fusogenic peptide (SEQ ID NO:72). The fusogenic peptide was added to the DOMTA/peptide formulation to achieve a final concentration of 0.1 mg/mL to see if transfection reagents were further enhanced by the addition of a fusogenic peptide and could provide higher transfection efficiency into HeLa cells and expression than the commercially available Lipofectamine 2000. The results are shown in Table 9.

The following Table 1 lists the peptide sequences that are referenced herein.

TABLE 1

| SEQ ID NO | Sequence |
|---|---|
| 1 | GYSTPPKKKRKVEDP |
| 2 | GYSTPPKTRRRP |
| 3 | GYSTPGRKKR |
| 4 | GYSTPRRNRRRRW |
| 5 | PDEVKRKKKPPTSYG |
| 6 | PRRRTKPPTSYG |
| 7 | RKKRGPTSYG |
| 8 | WRRRRNRRPTSYG |
| 9 | GYGPPKKKRKVEAPYKA |
| 10 | PAAKRVKLD |
| 11 | RQRRNELKRSP |
| 12 | KRPAATKKAGQAKKKK |
| 13 | VRKKRKTEEESPLKDKDAKKSKQE |
| 14 | RLRRDAGGRGGVYEHLGGAPRRRK |
| 15 | KRKGDEVDGVDECAKKSKK |
| 16 | NQSSNFGPMKGGNFGGRSSGPYGGGGQYFAKPRNQGGY |
| 17 | GGKRTADGSEFESPKKARKVEAYPKAW |
| 18 | GGKRTADGSEFESPKKKRAVEAYPKAW |
| 19 | GGKRTADGSEFESPKKKAKVEAYPKAW |
| 20 | GGKRTADGSEFESPKKKRKVEAPYKAWK |
| 21 | GGKRTADGSEFESPKKKRKVEYKAWK |
| 22 | GYGPAAKRVKLDEAYPKAWK |
| 23 | GGKRTADGSEFEPAAKRVKLDEAYPKAWK |
| 24 | GTGPKKKRKVGGGGYGPKKKRLVG |
| 25 | KRPAATKKAGQAKKKKLEAYPKAWK |
| 26 | ATKGTKRSYEQMETGE |
| 27 | GKWERKPIRCAS |
| 28 | GYGKRTADSQHSTPPKKKRKVEAPYKAWK |
| 29 | KRTADSQHSTPPKKKRKVEAPYKAWK |
| 30 | GYGPPKKKRKVEAPYKAWKWAKYPAMRRAHHRRRRASHRRRTTTGT |
| 31 | GYGPPKKKRKVEAPYKAWKRGARRYSKMKRRRRRVARRHRRRP |
| 32 | FWGYGYGPPKKKRKVEAPYKAWK |
| 33 | GKPSSDDEATADSQHSTPPKKKERKVED |
| 34 | GKPTADDQHSTPPKKKRKVED |
| 35 | GGKRTADGSEFESPKKARKVEAYPKAK |
| 36 | EKIRLRPGRKKRYRLKHL |
| 37 | PEGTRQARRNRRRRWRKR |
| 38 | PEGTRQPRRNRRRRWRKR |
| 39 | GVKRSYGAARGDDRRRPNVVAPYKAW |
| 40 | KSVPNRTRTYIKLKRLRFKGAPYKAW |
| 41 | EMRRRREEEGLQLRKQKREEQLFKRRN |
| 42 | FEAALAEALAEALA |
| 43 | Ac-LARLLPRLLARL-NHCH$_3$ |
| 44 | GLLEELLELLEELWEELLEG |
| 45 | GWEGLIEGIEGGWEGLIEG |
| 46 | GLFEALAEFIEGGWEGLIEG |
| 47 | GLFEALLELLESLWELLLEA |
| 48 | GGYCLEKWMIVASELKCFGNTA |
| 49 | GGYCLTRWMLIEAELKCFGNTAV |
| 50 | WEAALAEALAEALAEHLAEALAEALEALAA |
| 51 | GLFGAIAGFIENGWEGMIDGWYG |
| 52 | GIGAVLKVLTTGLPALISWIKRKRQQ |
| 53 | GRKKRRQRRRPPQ |
| 54 | RQIKIWFQNRRMKWKK |
| 55 | GWTLNSAGYLLGKINLKALAALAKKIL |
| 56 | WEAKLAKALAKALAKHLAKALAKALKACEA |
| 57 | GLFKALLKLLKSLWKLLLKA |
| 58 | GLFRALLRLLRSLWRLLLRA |
| 59 | GLFEALLELLESLYELLLEA |
| 60 | GLFEALEELWEA |
| 61 | GLFLLEEWLE |

TABLE 1-continued

| SEQ ID NO | Sequence |
|---|---|
| 62 | GLFLLEEWLEK |
| 63 | GLFEALLELLESLWELLLEAK |
| 64 | Suc-GLFKLLEEWLE |
| 65 | Suc-GLFKLLEEWLEK |
| 66 | GLFEAIAEFIEGGWEGLIEG |
| 67 | GLFKAIAKFIKGGWKGLIKG |
| 68 | IRFKKTKLIASIAMALC |
| 69 | ALAGTIIAGASLTFQVLDKVlEELGKVSRK |
| 70 | GLFEAIEGFIENGWEGMIDGWYG |
| 71 | GYICRRARGDNPDDRCT |
| 72 | GLFEAIAEFIEGGWEGLIEGCA |
| 73 | GLFHAIAHFIHGGWHGLIHGWWYG |
| 74 | RRRQRRKKRGGDIMGEWGNEIFGAIAGFLG |
| 75 | GLFEAIADFIENGWEGMIGGG |
| 76 | ALAGTIIAGASLTFQVLDKVlEELGKVSRKK |
| 77 | IRFKKTKLIASIAMA |
| 78 | GLWHLLLHLWRRLLRLLR |
| 79 | KKIMLLLMTLLLVSLPLAQEQ |
| 80 | GLFEALLELLESLWELLLEAWYG |
| 81 | RLLRLLLRLWRRLLRLLR |
| 82 | LLELELLELELLLELELLELELLLEL |
| 83 | GLFEALLELLESLWELLLEARRRRRRRR |
| 84 | GLFEALLELLESLWELLLEARRRRRR |
| 85 | GLFEALLELLESLWELLLEAKKKKKKKK |
| 86 | GLFEALLELLESLWELLLEAKKKKKK |
| 87 | GLFEALLELLESLWELLLEAKK |
| 88 | GLFEALLELLESLWELLLEAKKKK |
| 89 | GLFEALLELLESLWELLLEAEE |
| 90 | GLFEALLELLESLWELLLEAEEEE |
| 91 | GLFEALLELLESLWELLLEAEEEEEE |
| 92 | GLFEALLELLESLWELLL |
| 93 | PLSSIFSRIGDPRGARRYAKMKRRRRRVARRHRRRP |
| 94 | GPFHYFQFLFPPV |
| 95 | GSSSWWQRWWPPW |
| 96 | RRRQRRKKR |
| 97 | KKKK |
| 98 | KKKKKK |
| 99 | KKKKKKKK |
| 100 | KKKKKKKKKK |
| 101 | KKKKKKKKKKKK |
| 102 | KKKKKKKKKKKKKKK |
| 103 | KKKKKKKKKKKKKKKKKK |
| 104 | KKKKKKKKKKKKKKKKKKKKK |
| 105 | RRRR |
| 106 | RRRRRR |
| 107 | RRRRRRRR |
| 108 | RRRRRRRRRR |
| 109 | RRRRRRRRRRRR |
| 110 | RRRRRRRRRRRRRRR |
| 111 | RRRRRRRRRRRRRRRRRR |
| 112 | RRRRRRRRRRRRRRRRRRRRR |
| 113 | YKA |
| 114 | KKKKKKKKWKGGGGACYGLPHLFCG |
| 115 | YKAKKKKKKKKWK |
| 116 | KTPKKAKKPKTPKKAKKP |
| 117 | KKAKKPAATRKSSKNPKKPKTVKPKKVAK |
| 118 | RGARRYSKMKRRRRVARRHRRRP |
| 119 | TRQARRNRRRRWRERQRGSGSG |
| 120 | KRPRGRPKGSKKNWRRRKRRASRRSPRRR |
| 121 | KRGRGRPRKQPPKEPSEVPTPKRPRGRPKGSKNK |
| 122 | KEKYEKDIAAYRAKGKPAAKKGVVKAEKSKKKK |
| 123 | YKAKKKKKKKKKWK |
| 124 | KKKKKKGGC |
| 125 | YRARRRRRRRRWR |
| 126 | YRARRRRRRRRRWR |
| 127 | KGDPKKPRGKMSSYAFFVQTCREEHKKKHPDASVNFSEFSKK |
| 128 | KKQLKKQLKKQLKQWK |
| 129 | KKSPKKSPKKSPKKSK |
| 130 | KLSKLEKKSKLEK |
| 131 | KLSKLEKKLSKLEKKSKLEK |
| 132 | KSLKKSLKKSLKKSK |
| 133 | KIRRRGKNKVAARTCRQRRTDR |
| 134 | KIRRRGKNKVAAQNCRKRKLET |
| 135 | KRRIRREKNKMAAAKCRNRRRELT |
| 136 | KDRSNLLERHTR |
| 137 | KRPAATKKAGQAKKKL |

TABLE 1-continued

| SEQ ID NO | Sequence |
|---|---|
| 138 | RRRRRREEEE |
| 139 | RRRRRREEEEE |
| 140 | RRRRRREEEEEEE |
| 141 | RRRRRRRREEEE |
| 142 | RRRRRRRREEEEE |
| 143 | RRRRRRRREEEEEEE |
| 144 | RRRRRRRRRRREEEE |
| 145 | RRRRRRRRRRREEEEEE |
| 146 | RRRRRRRRRRREEEEEEE |
| 147 | KLSKLEKK |
| 148 | SKLEK |
| 149 | KLSKLEKKLSKLEKK |
| 150 | PKKKRKVGGGRGDSP |
| 151 | LPHKSMPCG |
| 152 | GACLQHKSMPCG |
| 153 | YGLPHLFCG |
| 154 | SERSMNFCG |
| 155 | DHYSLYEDLERGTDK |
| 156 | ISLPRTSGAQRASTTR |
| 157 | EKLQTKYGLPHKVEFCG |
| 158 | TRISESQAKPGD |
| 159 | LVFFDY |
| 160 | WGGNGPTTFDCSGYTKYVFAK |
| 161 | INIGTTGWGDHYSLY |
| 162 | YDNIHG |
| 163 | AGWGKFLVGFGRV |
| 164 | SIGYPLP |
| 165 | TTHWGFTL |
| 166 | HLQIQPYPQISG |
| 167 | KLNIVSVNG |
| 168 | RGH |
| 169 | DNRIRLQAKAA |
| 170 | KIKMVISWKG |
| 171 | LPWYSYLYAVSA |
| 172 | WNLPWYYSVSPT |
| 173 | WNL |
| 174 | PWYYSVSPT |
| 175 | SSWESYKSGGGTRL |
| 176 | RDWSSQHPGRCNGETHLK |
| 177 | SLPTLTL |
| 178 | VICTGGDYSFALPVGQWPVMT |
| 179 | DKPSYQFGGHNSVDFEEDTLPKV |
| 180 | RARRRKRASATQLYQTCKASGTCPPD |
| 181 | SGDYSFALPVGQWPWMTG |
| 182 | CTGGDYSFALPVGQWPW |
| 183 | FYYDYDFFFDYWGQG |
| 184 | HLRRLRRRLLREAEG |
| 185 | DYYCAAWDDSLNGYSVF |
| 186 | YYCLQSMEDPYTFGG |
| 187 | YYCARSDGNYGYYYALDYDY |
| 188 | AARSPSYYRYDY |
| 189 | GPYYAMDYD |
| 190 | YYCQQRSSYPYTEGGAYPKAWK |
| 191 | YYCQRYDSDWSFGQGTKL |
| 192 | YYCARSGYYAMDYWGQGT |
| 193 | RVRRGACRGDCLG |
| 194 | RVRRGACRYDCLG |
| 195 | YYCAKGTHWGFWSGYFDYWGQGT |
| 196 | GRENYHGCTTHWGFTLC |
| 197 | VQATQSNQHTPRGGGSK |
| 198 | DPRAPGS |
| 199 | YYCQQRSSYPYTFGG |
| 200 | AARSPSYYRYDYGPYYAMDYD |
| 201 | GPKLTGILISILSLFVES |
| 202 | KYILRWRPKNS |
| 203 | IKVAV |
| 204 | WTPPRAQITGYRLTVGLTRR |
| 205 | AASIKVAVSADR |
| 206 | KLDAPT |
| 207 | NRWHSIYITRFG |
| 208 | PHSRN |
| 209 | SSFHFDGSGYAM |
| 210 | RGDS |
| 211 | IAFQRN |
| 212 | GRGDSP |
| 213 | TWYKIAFQRRK |

TABLE 1-continued

| SEQ ID NO | Sequence |
|---|---|
| 214 | EDGIHEL |
| 215 | SLVRNRRVITIQ |
| 216 | YRVRVTPKEKTGPMKE |
| 217 | LQVQLSR |
| 218 | SPPRRARVT |
| 219 | RKRLQVQLSIRT |
| 220 | ATETTITIS |
| 221 | NAPFPKLSWTIQ |
| 222 | VSPPRRARVTDATETTITISWRTKTETITGG |
| 223 | WTIQTTVDRGLL |
| 224 | KPDVRSYTITG |
| 225 | DTINNGRDHMILI |
| 226 | ANGQTPIQRYIK |
| 227 | MILISIGKSQKRM |
| 228 | PRARITGYIIKYEKPGSPPREVVPRPRPGV |
| 229 | PPFLMLLKGSTR |
| 230 | WQPPRARI |
| 231 | NQRLASFSNAQQS |
| 232 | WQPPRARITGYIIKYEKPG |
| 233 | ISNVFVQRMSQSPEVLD |
| 234 | YEKPGSPPREVVPRPRPGV |
| 235 | KARSFNVQLLQD |
| 236 | KNNQKSEPLIGRKKT |
| 237 | KNSFMALYLSKG |
| 238 | EILDVPST |
| 239 | KNSFMALYLSKGRLVFALG |
| 240 | IDAPS |
| 241 | RDSFVALYLSEGHVIFAGLG |
| 242 | VVIDASTAIDAPSNL |
| 243 | KPRLQFSLDIQT |
| 244 | LDVPS |
| 245 | DGQWHSVTVSIK |
| 246 | REDV |
| 247 | FVLYLGSKNAKK |
| 248 | PHSRNRGDSP |
| 249 | LAIKNDNLVYVY |
| 250 | LWVTVRSQQRGLF |
| 251 | AYFSIVKIERVG |
| 252 | GTNNWWQSPSIQN |
| 253 | DVISLYNFKHIY |
| 254 | WVTVTLDLRQVFQ |
| 255 | FFDGSSYAVVRD |
| 256 | RQVFQVAYIIIKA |
| 257 | LHVFYDFGFGFSNG |
| 258 | LTRYKITPRRGPPT |
| 259 | LKKAQINDAKYREISIIYHN |
| 260 | LLEFTSARYIRL |
| 261 | RAYFNGQSFIAS |
| 262 | YIRLRLQRIRTL |
| 263 | SRLRGKNPTKGK |
| 264 | RRYYYSIKDISV |
| 265 | LHKKGKNSSKPK |
| 266 | SINNTAVNQRLT |
| 267 | RLKTRSSHGMIF |
| 268 | GGFLKYTVSYDI |
| 269 | GEKSQFSIRLKT |
| 270 | RDQLMTVLANVT |
| 271 | TLFLAHGRLVFM |
| 272 | ANVTHLLIRANY |
| 273 | LVFMFNVGHKKL |
| 274 | AGTFALRGDNPQG |
| 275 | TLFLAHGRLVFMFNVGHKKL |
| 276 | VLIKGGRARKHV |
| 277 | DFMTLFLAHGRLVFMGNVG |
| 278 | LSNIDYLIKAS |
| 279 | HKKLKIRSQEKY |
| 280 | LQQSRIANISME |
| 281 | GAAWKIKGPIYL |
| 282 | NLLLLLVKANLK |
| 283 | VIRDSNVVQLDV |
| 284 | HRDELLLWARKI |
| 285 | GLIYYVAHQNQM |
| 286 | KRRARDLVHRAE |
| 287 | DYATLQLQEGRLHFMFDLG |
| 288 | SQFQESVDNITK |
| 289 | KKGSYNNIVVHV |

TABLE 1-continued

| SEQ ID NO | Sequence |
|---|---|
| 290 | PGGMREKGRKAR |
| 291 | ADNLLFYLGSAK |
| 292 | MEMQANLLLDRL |
| 293 | GSAKFIDFLAIE |
| 294 | LSEIKLLISAR |
| 295 | KVSFLWWVGSGV |
| 296 | RDFTKATNIRLRFLR |
| 297 | SYWYRIEASRTG |
| 298 | ISTVMFKFRTFS |
| 299 | YFDGTGFAKAVG |
| 300 | KQANISIVDIDSN |
| 301 | NGQWHKVTAKKI |
| 302 | FSTRNESGIILL |
| 303 | AKKIKNRLELVV |
| 304 | RRQTTQAYYAIF |
| 305 | GFPGGLNQFGLTTN |
| 306 | YAIFLNKGRLEV |
| 307 | NQFGLTTNIRFRG |
| 308 | KNRLTIELEVRT |
| 309 | IRSLKLTKGTGKP |
| 310 | GLLFYMARINHA |
| 311 | AKALELRGVQPVS |
| 312 | VQLRNGFPYFSY |
| 313 | GQLFHVAYILIKF |
| 314 | HKIKIVRVKQEG |
| 315 | NVLSLYNFKTTF |
| 316 | DFGTVQLRNGFPFFSYDLG |
| 317 | SQRIYQFAKLNYT |
| 318 | NIRLRFLRTNTL |
| 319 | EVNVTLDLGQVFH |
| 320 | GKNTGDHFVLYM |
| 321 | GQVFHVAYVLIKF |
| 322 | VVSLYNFEQTFML |
| 323 | HQQDLGTAGSCLRKFSTMFLF |
| 324 | RFDQELRLVSYN |
| 325 | HQQDLGTAGSCLRKFSTMFLFCNI |
| 326 | RLVSYSGVLFFLK |
| 327 | VAEIDGIEL |
| 328 | NWRHISYITRFG |
| 329 | GIIFFL |
| 330 | KRLQVQLRSIRT |
| 331 | ASKAIQVFLLGG |
| 332 | TWYKIAFQRNRK |
| 333 | VLVRVERATVFS |
| 334 | QVFQVAYIIIKA |
| 335 | TVFSVDQDNMLE |
| 336 | GEFYFDLRLKGDK |
| 337 | RLRGPQRVFDLH |
| 338 | GTPGPQGIA |
| 339 | FDLHQNMGSVN |
| 340 | GQRDVV |
| 341 | LRAHAVDVNG |
| 342 | TAGSCLRKFSTM |
| 343 | LFSHAVSSNG |
| 344 | KGHRGF |
| 345 | TAGSCLRKFSTMFLF |
| 346 | TAGSCLRKFSTMFLFCNI |
| 347 | DLGTAGSCLRKFSTM |
| 348 | HQQDLGTAGSCLRKFSTM |
| 349 | RNIAEIIKDI |
| 350 | SIGFRGDGQTC |
| 351 | LNRQELFPFG |
| 352 | RIQNLLKITNLRIKFVK |
| 353 | KKQRFRHRNRKGYRSQ |
| 354 | SINNTAVMQRLT |
| 355 | FRHRNRKGY |
| 356 | RYRVRVTPKEKTGPMKE |
| 357 | SETTVKYIFRLHE |
| 358 | GHRGPTGRPGKRGKQGQKGDS |
| 359 | KAFDITYVRLKF |
| 360 | GDLGRPGRKGRPGPP |
| 361 | YIGSR |
| 362 | RGEFYFDLRLKGDK |
| 363 | LAGSCLARFSTM |
| 364 | LALFLSNGHFVA |
| 365 | ISRCQVCMKKRH |

TABLE 1-continued

| SEQ ID NO | Sequence |
|---|---|
| 366 | PGRWHKVSVRWE |
| 367 | TDIPPCPHGWISLWK |
| 368 | VRWGMQQIQLVV |
| 369 | TAIPSCPEGTVPLYS |
| 370 | KMPYVSLELEMR |
| 371 | GPAGKDGEAGAQG |
| 372 | VLLQANDGAGEF |
| 373 | GLPGER |
| 374 | DGRWHRVAVIMG |
| 375 | LAGSCLPVFSTL |
| 376 | APVNVTASVQIQ |
| 377 | TAGSCLRRFSTM |
| 378 | KQGKALTQRHAK |
| 379 | TAGSCLRKF |
| 380 | RYVVLPR |
| 381 | TAGSCL |
| 382 | SPYTFIDSLVLMPY |
| 383 | TAG |
| 384 | PDSGR |
| 385 | QQNLGSVNVSTG |
| 386 | SRATAQKVSRRS |
| 387 | DPGYIGSR |
| 388 | GSLSSHLEFVGI |
| 389 | VILQQSAADIAR |
| 390 | RNRLHLSMLVRP |
| 391 | KDISEKVAVYST |
| 392 | APMSGRSPSLVLK |
| 393 | LGTIPG |
| 394 | AFGVLALWGTRV |
| 395 | TDIRVTLNRLNTF |
| 396 | IENVVTTFAPNR |
| 397 | AFSTLEGRPSAY |
| 398 | LEAEFHFTHLIM |
| 399 | TSAEAYNLLLRT |
| 400 | HLIMTFKTFRPA |
| 401 | LNRRYEQARNIS |
| 402 | KTWGVYRYFAYD |
| 403 | SLLSQLNNLLDQ |
| 404 | TNLRIKFVKLHT |
| 405 | RDIAEIIKDI |
| 406 | KRLVTGQR |
| 407 | SHAVSS |
| 408 | GPGVVVVERQYI |
| 409 | ADTPPV |
| 410 | NEPKVLKSYYYAI |
| 411 | LRAHAVDING |
| 412 | YYAISDFAVGGR |
| 413 | DSITKYFQMSLE |
| 414 | LPFFNDRPWRRAT |
| 415 | YTALIIATDN |
| 416 | FDPELYRSTGHGGH |
| 417 | VITVKDINDN |
| 418 | TNAVGYSVYDIS |
| 419 | GLDRESYPYY |
| 420 | APVKFLGNQVLSY |
| 421 | MKVSATDADD |
| 422 | SFSFRVDRRDTR |
| 423 | PQVTRGDVFTMP |
| 424 | TWSKVGGHLRPGIVQSG |
| 425 | KEAEREVTDLLR |
| 426 | RGDV |
| 427 | AAEPLKNIGILF |
| 428 | FALWDAIIGEL |
| 429 | VGVAPG |
| 430 | LWPLLAVLAAVA |
| 431 | PGVGV |
| 432 | VFDNFVLK |
| 433 | TSIKIRGTYSER |
| 434 | TTSWSQCSKS |
| 435 | DPETGV |
| 436 | KRSR |
| 437 | QGADTPPVGV |
| 438 | SVVYGLR |
| 439 | PLDREAIAKY |
| 440 | DGRGDSVAYG |
| 441 | HAVDI |

TABLE 1-continued

| SEQ ID NO | Sequence |
|---|---|
| 442 | LALERKDHSG |
| 443 | DQNDN |
| 444 | YSMKKTTMKIIPFNRLTIG |
| 445 | QDPELPDKNM |
| 446 | RGDF |
| 447 | LVVQAADLQG |
| 448 | GVYYQGGTYSKAS |
| 449 | NDDGGQFVVT |
| 450 | TAGSCLRKFSCL |
| 451 | YILHVAVTN |
| 452 | CNYYSNSYSFWLASLNPER |
| 453 | TYRIWRDTAN |
| 454 | TGLSCLQRFTTM |
| 455 | GFTCECSIGFRGDGQTCYGIVFWSEV |
| 456 | HHLGGAKQAGDV |
| 457 | SCLPGFSGDGRACRDVDECGH |
| 458 | MAPRPSLAKKQRFRHRNRKGYRSQRGHSRG |
| 459 | KKQKFRHRNRKGYRSQ |
| 460 | KKQKFKHRNRKGYRS |
| 461 | KKQKFRRRNRKGYRSH |
| 462 | TAIPPCPHGWISLWK |
| 463 | KKQKSRHRSRKRYRS |
| 464 | KKQKSRRRSRKGYRS |
| 465 | ISRCTVC |
| 466 | ISRCQVCMKRRH |
| 467 | VSRCTVC |
| 468 | TDIPPCPQGWISLWK |
| 469 | TVKAGELEKIISRCQVMKKRH |
| 470 | TDIPSCPHGWISLWK |
| 471 | TDIPPCPAGWISLWK |
| 472 | TEIPPCPQGWISLWK |
| 473 | TDVPPCPQGWISLWK |
| 474 | RLVSYNGILFFLK |
| 475 | RLVSYSGVIFFLK |
| 476 | RLVSYNGILFFL |
| 477 | RLVSYSGIIFFLK |
| 478 | RFEQELRLVSYSGVLFFLKQ |
| 479 | RLVSYNGIIFFLK |
| 480 | DPAFKIEDPYSPRIQNLLKITNLRIKFVKL |
| 481 | TKRFEQELRLVSYSGVLFFL |
| 482 | GGRLKYSVAF |
| 483 | GGFLRYTVSYDI |
| 484 | GGFLKYTVSYDV |
| 485 | LGNKLTAFGGFLKYTVSYDIPV |
| 486 | GGYLKYTVSYDI |
| 487 | GEIFFDMRLKGDK |
| 488 | GEIYFDLRLKGDK |
| 489 | GEIYLDMRLKGDK |
| 490 | IGQPGAKGEPGEFYFDLRLKGDKGDPGFPG |
| 491 | GEVFFDMRLKGDK |
| 492 | LAGSCLPIFSTL |
| 493 | AHNQDLGLAGSCLARFSTMPFLYCNPGDIC |
| 494 | QEKAHNQDLGLAGSCLPVFSTLPFAYCNIH |
| 495 | LAGSCLPVFSTM |
| 496 | GNKRAHGQDLGTAGSCLRRFSTMPFMFCNI |
| 497 | RAHGQDLGTAGSCLRRFSTMP |
| 498 | RKRLQVQLNIRT |
| 499 | HLVLPLQQSDVRKRLQVQLSIRTFASSGLI |
| 500 | RKRLSVQLRIRT |
| 501 | DLGTAGSCLRRFSTM |
| 502 | RNIAEIIKDI |
| 503 | TAGSCLRKFSTMRRRRRRRRRRRR |
| 504 | FTLTGLLGTLVTMGLLT |
| 505 | APYKAWK |
| 506 | STSKTNRGDDSNWSKRVTNNKPS |
| 507 | STSKRKRGDDSNWSKRVTKKKPS |
| 508 | STSKRKRGDDSNWSKRVSKKKPS |
| 509 | STSKRKRGDDANWSKRVTKKKPS |
| 510 | PLAGSKRKRADEVAWSKRGTKKKPER |
| 511 | PLAGSKRKRADEVAWSKRGTKKKPERTSAARAGPSRRIR |
| 512 | STSKRKRGDDANWSKRTTKKKPSS |
| 513 | STSKRKRGDDANWSKRTTKKKPSSAGLKRAGSKADRPSL |
| 514 | PTTAGKRKRSDDAAWSKRARPKAGRT |
| 515 | PTTAGKRKRSDDAAWSKRARPKAGRTSAARPGTSVRRIR |
| 516 | SSSLGKRKRSDEGAWSKGKSKKKAMR |
| 517 | SSSLGKRKRSDEGAWSKGKSKKKAMRGSSSRRPGPVRGP |

TABLE 1-continued

| SEQ ID NO | Sequence |
|---|---|
| 518 | PTTAGKRKRTDDAAWSKRARPKAGR |
| 519 | PTTAGKRKRTDDAAWSKRARPKAGRTSAARPGTAVRRVR |
| 520 | PATAGKRKRSDDAAWSKRARPKAGRTSAAR |
| 521 | PATAGKRKRSDDAAWSKRARPKAGRTSAARPGTSVRRIR |
| 522 | SSSLGKRKRSNGGDWSKRSAKKKPA |
| 523 | SSSLGKRKRSNGGDWSKRSAKKKPAGTPSRRAGPGRGPR |
| 524 | SSSLGKRKRSDEGAWSKGKSKKKAMR |
| 525 | SSSLGKRKRSDEGAWSKGKSKKKAMRGSSSRRPGPVRGP |
| 526 | STSKRKRGDDANWNKRPTKKKPSS |
| 527 | STSKRKRGDDANWNKRPTKKKPSSAGLKKAGSKAERPSL |
| 528 | SGALKRKRSDEVAWSRRRPVKKPV |
| 529 | SGALKRKRSDEVAWSRRRPVKKPVRRAPPPRAGPSVRRG |
| 530 | SGALKRKRSDEVAWSRRKPAKKPAR |
| 531 | SGALKRKRSDEVAWSRRKPAKKPARQPPPPRAGPSVRRG |
| 532 | AGALKRKRSDEVAWSRRKPAKKPAR |
| 533 | AGALKRKRSDEVAWSRRKPAKKPARAPPPRAGPSVRRGL |
| 534 | STSKRKRGDDSNWSKRVTKKKPSSAGLKRAGSKADRPSLQIQTLQHAGTTMITVPSGGVCDLINTYARGSDEGNRHTSETLTYKIAIDYHFVADAAACRYSNTGTGVMWLVYDTTPGGQAPTPQTIFSYPDTLKAWPATWKVSRELCHRFVVKRRWLFNMETDGRIGSDIPPSNASWKPCKRNIYFHKFTSGLGVRTQWKNVTDGGVGAIQRGALYMVIAPGNGLTFTAHGQTRLYFKSVGNQ |
| 535 | DPQNALYYQPRVPTAAPTSGGVPWSRVGEVAILSFVALICFYLLYLWVLRDLILVLKARQGRSTEELIFGGQAVDRSNPIPNIPAPPSQGNPGPFVPGTG |
| 536 | GSQLVPPPSAFNYIESQRDEFQLSHDLTEIVLQFPSTASQITARLSRSCMKIDHCVIEYRQQVPINASGTVIVEIHDKRMTDNESLQASWTFPIRCNIDLHYFSSSFFSLKDPIPWKLYYRVSDSNVHQMTHFAKFKGKLKLSSAKHSVDIPFRAPTVKILAKQFSEKDIDFWHVGYGKWERRLVKSASSSRFGLRGPIEINPGESWATKSAIVTPNRNADLDIEEELLPYRELNRLGTNILDPGESASIVGIQRSQSNITMSMSQLNELVRSTVHECIKTSCIPSTPKSLS |
| 537 | RTGVKRSYGAARGDDRRRPNVV |
| 538 | SYVKTVPNRTRTYIKLRVR |
| 539 | MYSTSNRRGRSQTQRGSHVRRTGVKRSYGAARGDDRRRPNVVSKTQVEPRMTIQRVQENQFGPEFVLSQNSALSTFVTYPSYVKTVPNRTRTYIKLKRVRFKGTLKIERGQGDTIMDGPSSNIEGVFSMVIVVDRKPHVSQSGRLHTFDELFGARIHCHGNLSVVPALKDRYYIRHVTKRVVSLEKDTLLIDLHGTTQLSNKRYNCWASFSDLERDCNGVYGNITKNALLVYYCWLSDAQSKASTYVSFELDYLG |
| 540 | $R_{12}$-VDYGKWERKPIRCASMSR |
| 541 | $R_{12}$-GKWERKPIRCAS |
| 542 | $K_{16}$-GKWERKPIRCAS |
| 543 | $R_{12}$-VDFSHVDYGKWERKPIRCASMSRLGLRG |
| 544 | GVKRSYGAARGDDRRRPNVVAPYKAW-$R_{12}$ |
| 545 | KSVPNRTRTYIKLKRLRFKGAPYKAW-$R_{12}$ |
| 546 | RTGVKRSYGAARGDDRRRPNVV-$R_{12}$ |
| 547 | SYVKTVPNRTRTYIKGGGGG-$R_{12}$ |
| 548 | VDIPFRAPTIKILSKQFTEDDIDFWHVGYGKWERKLVRPASLSGRRGLRR |
| 549 | IDFWHVGYGKWERKLVRPASLSGRRGLRR |
| 550 | IDFWSVEKGETRRRLLNPTPHAHSPRPIAHR |
| 551 | IDFSHVGYGKWERKMIRSASISRLGLHN |
| 552 | VDFSHVGYGKWERKLIRSASTVKYGLPS |
| 553 | IDFSHVDYGKVERKLVKCESSSRLGLHS |
| 554 | IDFWSVGRKAQQRKLVQGPSLIGSRSMRY |
| 555 | IDFWSVGSKPQTRRLVDGSRLIGHSSRSLRV |
| 556 | IDFWSVERGETRRRLLNPTPSAGSNRALSKR |
| 557 | VDFWSVGKPKPIRRLIQNDPGTDYDTGPKYR |
| 558 | VDFWSVEKPKPIRRLLNPGPNQGPYPNTGHR |
| 559 | VDFSHVDYGKWERKLIRSASTSRYGLRS |
| 560 | VDFSHVDYGKWERKTLRSRSLSRIGLTG |
| 561 | IDFWHVGYGKWERRLVKSASSSRFGIRG |
| 562 | VDFFHVDYGRWERKHIRCASMSRVGLRG |
| 563 | GTFQHVDYGKWERKPIRCQSMSRVGYRR |
| 564 | VGYGKWERKLVRPASLS |
| 565 | VEKGETRRRLLNPTPHA |
| 566 | VGYGKWERKLIRSASTV |
| 567 | VEKPKPIRRLLNPGPNQ |
| 568 | VDYGKWERKLIRSASTS |
| 569 | VDYGKWERKTLRSRSLS |
| 570 | VGYGKWERRLVKSASSS |
| 571 | VDYGRWERKHIRCASMS |
| 572 | VERPKPIRRLLTPTPGC |
| 573 | PFRAPTIKILSKQFTEDDIDFWHVGYGKWERKLVRPASLSGRRGLRR |
| 574 | PFRAPTVKILSKQFTDKDIDFSHVGYGKWERKMIRSASISRLGL |
| 575 | DIAFRAPTVKILSKQFTDRDVDFSHVGYGKWERKLIRSASTVKYGL |
| 576 | DIRFKPPTINILSKDYTADCVDFWSVEKPKPIRRLLNPGPNQGPYPNTG |
| 577 | DIPFRAPTVKIHSKQFSHRDVDFSHVDYGKWERKTLRSRSLSRIGL |
| 578 | DIPFRAPTVKILAKQFSEKDIDFWHVGYGKWERRLVKSASSSRFGI |

TABLE 1-continued

| SEQ ID NO | Sequence |
|---|---|
| 579 | DIPFRAPTVKILSKQFTDKDVDFFHVDYGRWERKHIRCASMSRVGL |
| 580 | DIKYKPPTIKILSKDYTADCVDFWSVERPKPIRRLLTPTPGCG |
| 581 | ARTKQTARKSTGGKAPRKQLATKAARKSAPATGGVKKPHRYRPGTVA |
| 582 | SGRGKGGKGLGKGGAKRHRKVLRDNIQGITKPAI |

TABLE 2

Relative Fluorescence of Transfection of HeLa Cells

| SEQ ID NO | RF* |
|---|---|
| DOTMA | 7551 |
| 107 | 75 |
| 205 | 26368 |
| 216 | 6181 |
| 218 | 11179 |
| 219 | 13721 |
| 220 | 9398 |
| 224 | 5559 |
| 226 | 7340 |
| 229 | 8816 |
| 230 | 8944 |
| 234 | 3867 |
| 236 | 7202 |
| 236 | 5042 |
| 237 | 21288 |
| 238 | 6067 |
| 239 | 2717 |
| 256 | 2243 |
| 268 | 25885 |
| 323 | 14067 |
| 326 | 18946 |
| 327 | 5345 |
| 328 | 32528 |
| 332 | 9198 |
| 335 | 26954 |
| 336 | 25262 |
| 338 | 6241 |
| 341 | 4108 |
| 342 | 33666 |
| 343 | 5910 |
| 344 | 14415 |
| 345 | 8493 |
| 347 | 22527 |
| 348 | 22289 |
| 349 | 4433 |
| 350 | 13313 |
| 351 | 12279 |
| 352 | 32126 |
| 353 | 29119 |
| 354 | 4403 |
| 355 | 32628 |
| 357 | 22679 |
| 358 | 15132 |
| 359 | 3136 |
| 360 | 8516 |
| 361 | 3698 |
| 363 | 2590 |
| 365 | 36093 |
| 367 | 39008 |
| 369 | 14444 |
| 371 | 5180 |
| 373 | 8992 |
| 375 | 41076 |
| 377 | 15091 |
| 379 | 27424 |
| 381 | 22652 |
| 383 | 8012 |
| 450 | 21045 |
| 452 | 13888 |
| 454 | 34550 |
| 503 | 25368 |

*RF = Relative Fluorescence

TABLE 3

Relative Fluorescence of Transfection of HuVec Cells

| SEQ ID NO | RF* |
|---|---|
| DOTMA | 12230 |
| 205 | 8309 |
| 216 | 14693 |
| 218 | 14827 |
| 219 | 6237 |
| 220 | 8737 |
| 224 | 15945 |
| 226 | 20864 |
| 229 | 5452 |
| 230 | 9067 |
| 234 | 13956 |
| 235 | 26940 |
| 236 | 14418 |
| 237 | 2302 |
| 238 | 11083 |
| 239 | 1404 |
| 256 | 3030 |
| 268 | 5403 |
| 323 | 12815 |
| 326 | 4932 |
| 327 | 21018 |
| 328 | 3614 |
| 332 | 4221 |
| 335 | 6350 |
| 336 | 5366 |
| 338 | 12000 |
| 341 | 15906 |
| 342 | 12804 |
| 343 | 16239 |
| 344 | 11867 |
| 345 | 2939 |
| 347 | 20728 |
| 348 | 21214 |
| 349 | 22907 |
| 350 | 13163 |
| 351 | 15379 |
| 352 | 3130 |
| 353 | 8772 |
| 354 | 19284 |
| 355 | 14810 |
| 357 | 6009 |
| 358 | 25398 |
| 359 | 3024 |
| 360 | 24042 |
| 361 | 6017 |
| 363 | 1383 |
| 365 | 14764 |
| 367 | 13354 |
| 369 | 6536 |
| 371 | 10669 |
| 373 | 28811 |
| 375 | 5542 |
| 377 | 9326 |
| 379 | 14573 |
| 381 | 17542 |
| 383 | 20267 |

TABLE 3-continued

Relative Fluorescence of Transfection of HuVec Cells

| SEQ ID NO | RF* |
|---|---|
| 450 | 20911 |
| 452 | 1841 |
| 454 | 13336 |
| 503 | 12123 |

*RF = Relative Fluorescence

TABLE 4

Relative Fluorescence of Transfection of NL-1 iPS Cells

| SEQ ID NO | RF* |
|---|---|
| DOTMA | 8965 |
| 107 | 1441 |
| 205 | 13140 |
| 216 | 19626 |
| 218 | 17049 |
| 219 | 5770 |
| 220 | 15892 |
| 224 | 25209 |
| 226 | 24920 |
| 229 | 13491 |
| 230 | 14524 |
| 234 | 14410 |
| 236 | 43542 |
| 236 | 22256 |
| 237 | 8632 |
| 238 | 15856 |
| 239 | 4129 |
| 256 | 1825 |
| 268 | 15697 |
| 323 | 21694 |
| 326 | 9239 |
| 327 | 31383 |
| 328 | 8611 |
| 332 | 8725 |
| 335 | 14424 |
| 336 | 14875 |
| 338 | 17288 |
| 341 | 20446 |
| 342 | 11493 |
| 343 | 21726 |
| 344 | 10895 |
| 345 | 7836 |
| 347 | 21865 |
| 348 | 21645 |
| 349 | 33103 |
| 350 | 19132 |
| 351 | 24646 |
| 352 | 11628 |
| 353 | 9248 |
| 354 | 24043 |
| 355 | 7910 |
| 357 | 15624 |
| 358 | 21956 |
| 359 | 5548 |
| 360 | 27572 |
| 361 | 9363 |
| 363 | 4189 |
| 365 | 6364 |
| 367 | 17545 |
| 369 | 13124 |
| 371 | 17587 |
| 373 | 36290 |
| 375 | 5196 |
| 377 | 5474 |
| 379 | 6894 |
| 381 | 9644 |

TABLE 4-continued

Relative Fluorescence of Transfection of NL-1 iPS Cells

| SEQ ID NO | RF* |
|---|---|
| 383 | 21983 |
| 450 | 29856 |
| 452 | 10349 |
| 454 | 18100 |
| 503 | 19014 |

*RF = Relative Fluorescence

TABLE 5

Relative Fluorescence of Transfection of C2C12 Cells

| SEQ ID NO | RF* |
|---|---|
| DOTMA | 1289 |
| 205 | 2102 |
| 216 | 1001 |
| 218 | 3706 |
| 219 | 1346 |
| 220 | 1470 |
| 224 | 1469 |
| 226 | 1664 |
| 229 | 1164 |
| 230 | 2606 |
| 234 | 681 |
| 236 | 958 |
| 236 | 2142 |
| 237 | 6491 |
| 238 | 1550 |
| 239 | 10620 |
| 256 | 3207 |
| 268 | 2568 |
| 323 | 7698 |
| 326 | 8553 |
| 327 | 2043 |
| 328 | 5507 |
| 332 | 537 |
| 335 | 4689 |
| 336 | 9647 |
| 338 | 2290 |
| 341 | 2141 |
| 342 | 9496 |
| 343 | 3218 |
| 344 | 1678 |
| 345 | 6569 |
| 347 | 4457 |
| 348 | 8625 |
| 350 | 2631 |
| 351 | 3530 |
| 352 | 3324 |
| 353 | 4291 |
| 354 | 1912 |
| 355 | 1900 |
| 357 | 4506 |
| 358 | 2271 |
| 359 | 5693 |
| 360 | 2090 |
| 361 | 585 |
| 363 | 1080 |
| 365 | 5390 |
| 367 | 16207 |
| 369 | 3322 |
| 371 | 983 |
| 373 | 3037 |
| 375 | 5633 |
| 377 | 1710 |
| 379 | 3189 |
| 381 | 8834 |
| 383 | 1876 |
| 450 | 3795 |
| 452 | 21798 |

TABLE 5-continued

Relative Fluorescence of Transfection of C2C12 Cells

| SEQ ID NO | RF* |
|---|---|
| 454 | 9280 |
| 501 | 5913 |
| 502 | 2589 |
| 503 | 3973 |

*RF = Relative Fluorescence

TABLE 6

Relative Fluorescence of Transfection of Human Fibroblast Cells

| SEQ ID NO | RF* |
|---|---|
| DOTMA | 3397 |
| 205 | 8550 |
| 216 | 3117 |
| 218 | 11230 |
| 219 | 7389 |
| 220 | 4516 |
| 224 | 5995 |
| 226 | 3431 |
| 229 | 6811 |
| 230 | 11771 |
| 234 | 4145 |
| 236 | 3630 |
| 236 | 3000 |
| 237 | 2184 |
| 238 | 3348 |
| 239 | 4084 |
| 256 | 2656 |
| 268 | 4568 |
| 323 | 4826 |
| 326 | 3070 |
| 327 | 4662 |
| 328 | 5641 |
| 332 | 5178 |
| 335 | 8534 |
| 336 | 10449 |
| 338 | 5625 |
| 341 | 2284 |
| 342 | 9525 |
| 343 | 4590 |
| 344 | 12704 |
| 345 | 2816 |
| 347 | 9255 |
| 348 | 11802 |
| 349 | 8810 |
| 350 | 7105 |
| 351 | 8061 |
| 352 | 3059 |
| 353 | 8653 |
| 354 | 4998 |
| 355 | 6821 |
| 357 | 7167 |
| 358 | 5665 |
| 359 | 3206 |
| 360 | 5347 |
| 361 | 7014 |
| 363 | 3008 |
| 365 | 5219 |
| 367 | 10036 |
| 369 | 7590 |
| 371 | 4584 |
| 373 | 4872 |
| 375 | 7305 |
| 377 | 6638 |
| 379 | 8520 |
| 381 | 9953 |
| 383 | 5896 |
| 450 | 6996 |
| 452 | 2779 |

TABLE 6-continued

Relative Fluorescence of Transfection of Human Fibroblast Cells

| SEQ ID NO | RF* |
|---|---|
| 454 | 7568 |
| 501 | 9473 |
| 503 | 13085 |

*RF = Relative Fluorescence

TABLE 7

Relative Fluorescence of Transfection of Jurkat Cells

| SEQ ID NO | RF* |
|---|---|
| DOTMA | 9084 |
| 205 | 2298 |
| 216 | 3570 |
| 218 | 21451 |
| 219 | 10762 |
| 220 | 6428 |
| 224 | 13170 |
| 226 | 12976 |
| 229 | 8079 |
| 230 | 10229 |
| 234 | 5441 |
| 236 | 11006 |
| 236 | 4593 |
| 237 | 1501 |
| 238 | 6278 |
| 239 | 2343 |
| 256 | 3322 |
| 268 | 3236 |
| 323 | 2900 |
| 326 | 3018 |
| 327 | 14546 |
| 328 | 4770 |
| 332 | 3052 |
| 335 | 4567 |
| 336 | 4813 |
| 338 | 4475 |
| 341 | 18042 |
| 342 | 12825 |
| 343 | 23499 |
| 344 | 10160 |
| 345 | 2462 |
| 347 | 17720 |
| 348 | 15585 |
| 349 | 23167 |
| 350 | 9184 |
| 351 | 9730 |
| 352 | 3150 |
| 353 | 11107 |
| 354 | 16705 |
| 355 | 8132 |
| 357 | 2256 |
| 358 | 18820 |
| 359 | 1880 |
| 360 | 16607 |
| 361 | 7006 |
| 363 | 2432 |
| 365 | 5298 |
| 367 | 4365 |
| 369 | 11085 |
| 371 | 6093 |
| 373 | 12628 |
| 375 | 4272 |
| 377 | 6785 |
| 379 | 7711 |
| 381 | 10806 |
| 383 | 14910 |
| 450 | 8779 |
| 452 | 2554 |
| 454 | 8224 |
| 501 | 12350 |
| 503 | 9411 |

*RF = Relative Fluorescence

TABLE 8

Visual Confirmation of Transfection of Cells

| Cell Line | SEQ ID NOs |
|---|---|
| Rat Cortical Neurons | 220, 236, 238, 323, 327, 336, 338, 341, 343, 347, 348, 350, 351, 352, 354, 367, 369, 373, 375, 377, 454 |
| THP-1 | 219, 229, 230, 239, 323, 328, 332, 341, 343, 350, 351, 357, 358, 375, 450, 454 |
| Human Skeletal Muscle | 218, 219, 230, 328, 336, 344, 350, 351, 353, 355, 365, 375 |

TABLE 9

Relative Fluorescence DOTMA/SEQ ID NO: 72/Peptide as Compared with Lipofectamine 2000 for the Transfection of HeLa Cells

| Transfection Agent | RF* | | | |
|---|---|---|---|---|
| | 0.1† | 0.2† | 0.3† | 0.4† |
| Lipo# | 12694 | 22154 | 21542 | 19286 |
| DOTMA/72§ | 10178 | 11133 | 8021 | 7032 |
| SEQ ID NO‡ | | | | |
| 218 | 12686 | 13103 | 10151 | 10081 |
| 219 | 12135 | 13841 | 13531 | 11712 |
| 236 | 5993 | 8846 | 8492 | 7316 |
| 237 | 8986 | 9753 | 8015 | 8288 |
| 268 | 10162 | 9934 | 10792 | 9519 |
| 323 | 15537 | 16620 | 10839 | 9244 |
| 326 | 6887 | 9487 | 10330 | 9227 |
| 328 | 11037 | 12229 | 10801 | 10951 |
| 335 | 12866 | 12458 | 11547 | 9753 |
| 336 | 14442 | 16702 | 13434 | 11334 |
| 341 | 6406 | 7469 | 8020 | 7546 |
| 342 | 41299 | 36040 | 28841 | 18351 |
| 343 | 6961 | 8626 | 8577 | 8160 |
| 344 | 13315 | 16387 | 12564 | 12511 |
| 347 | 23188 | 21493 | 16814 | 14140 |
| 348 | 17413 | 18615 | 16164 | 15054 |
| 350 | 24092 | 23238 | 19802 | 22255 |
| 351 | 7678 | 11499 | 10575 | 8791 |
| 353 | 36315 | 44772 | 36882 | 25802 |
| 355 | 18362 | 27990 | 22367 | 18289 |
| 357 | 7718 | 11798 | 9229 | 9107 |
| 358 | 12331 | 12683 | 13686 | 11097 |
| 360 | 9946 | 11168 | 10381 | 8995 |
| 365 | 26620 | 43775 | 36054 | 21540 |
| 367 | 10427 | 21411 | 23001 | 17529 |
| 369 | 8737 | 16706 | 14880 | 12645 |
| 375 | 22457 | 30891 | 34887 | 29024 |
| 377 | 39115 | 40072 | 32914 | 22457 |
| 379 | 50018 | 47049 | 39036 | 26448 |
| 381 | 34187 | 37463 | 27007 | 20088 |
| 450 | 11962 | 17346 | 12553 | 10241 |
| 452 | 6276 | 12671 | 12047 | 10918 |
| 454 | 34033 | 37099 | 27412 | 16023 |
| 501 | 23571 | 23993 | 20410 | 14749 |
| 503 | 12827 | 20006 | 17101 | 16206 |

*RF = Relative Fluorescence
†Volume of DOTMA/SEQ ID NO: 72/Peptide in μL in well of a 96 well plate
Lipofectamine 2000
§DOTMA and SEQ ID NO: 72 with no additional peptide
‡Peptide mixed with DOTMA/SEQ ID NO: 72

Example 2: Plant Movement Proteins

Cells were plated to so that on the day of transfection the cells were 70% confluent in 96 well tissue culture plates. A DOMTA/DOPE Lipid solution (1:1 molar ratio) at 2 mg/mL in water were mixed with an equal volume of plant virus movement protein derived peptides that had the nucleic acid binding moiety RRRRRRRRRRRRR (SEQ ID NO:109) or KKKKKKKKKKKKKKK (SEQ ID NO: 102) covalently linked to the N-terminus, or C-terminus of each peptide during peptide synthesis. Peptides were at 2 mg/mL in water. The DOTMA/DOPE and the plant virus movement peptide solution the was diluted 1 to 1 (v/v) in water. DOMTA/DOPE/PEPTIDE solutions were added to 0.1 mL of a plasmid DNA solution (EFlAlpha eGFP plasmid) at 10 μg/mL in OptiMEM.

All solutions were at room temperature. A volume of 0.2 mL of a 10 μg/mL solution of DNA was aliquoted into each well of a non-tissue cultured treated plate. 1-6 μL of transfection reagents were added to DNA solutions respectively. The transfection reagent and DNA solution was mixed by pipetting up and down twice. Transfection complexes were formed for 10 minutes. After 10 minutes, 0.01 or 0.02 mL of the transfection complex was added to cells. HuVEC, HeLa, human adult keratinocytes, human primary adult fibroblast, and A549 cells all respectively received 0.01 mL of the transfection complex. Human skeletal muscle cells, mouse C2Cl2 cells, and Jurkat, cells received 0.02 mL of the transfection complex. Cells were incubated for 42 hours at 37° C. at 5% $CO_2$. Plates were read on a fluorescent plate reader. Cells were also examined visually under a microscope to assess the extent of transfection (in terms of the percent of cells transfected) with a fluorescent microscope. Other modes of analysis, for example quantification with B-galactosidase or luciferase reports plasmids can also be used. If the plate reader did not show a sufficient signal to noise ratio, then plates were scored for cells transfected and those peptides that show increase over DOTMA alone were noted.

TABLE 10

Relative Fluorescence of Transfection of Hela Cells

| Transfection Agent SEQ ID NO | | | | | | |
|---|---|---|---|---|---|---|
| 543 | 12174 | 42502 | 38779 | 28451 | 13793 | 7705 |
| 545 | 11056 | 28529 | 28943 | 14693 | 13009 | 10902 |
| 544 | 10683 | 19151 | 19877 | 16908 | 12759 | 8938 |
| 540 | 6422 | 35653 | 27970 | 18620 | 13917 | 10336 |
| 541 | 17145 | 36476 | 37105 | 23644 | 20473 | 15523 |
| 542 | 9010 | 32901 | 47293 | 42152 | 35631 | 18856 |
| DOTMA 1 μg/ml | 4424 | 4782 | 5377 | 6992 | 9694 | 11720 |
| 109 | 4157 | 5578 | 6606 | 8520 | 8007 | 7803 |
| 547 | 5899 | 9491 | 10275 | 11241 | 8829 | 7989 |
| 546 | 15190 | 15022 | 12772 | 11535 | 8117 | 7181 |
| Blank | 3912 | 3941 | 3860 | 3805 | 3990 | 3871 |

TABLE 11

Relative Fluorescence of Transfection of Human Primary Fibroblast Cells

| Transfection Agent | Rf | | | | | |
|---|---|---|---|---|---|---|
| SEQ ID NO | 1 μl | 1.5 μl | 2 μl | 3 μl | 4 μl | 6 μl |
| Blank | 26467 | 26415 | 26510 | 26317 | 26738 | 26620 |
| 543 | 30416 | 45401 | 39786 | 33091 | 28648 | 28698 |
| 545 | 34309 | 48184 | 37497 | 29067 | 28928 | 29256 |
| 544 | 31368 | 39311 | 37634 | 32892 | 31428 | 28367 |
| 540 | 29368 | 40610 | 35505 | 33853 | 33063 | 30219 |
| 541 | 35030 | 44894 | 42097 | 31837 | 29537 | 28921 |
| 542 | 30818 | 43609 | 46966 | 36343 | 33706 | 31787 |
| DOTMA 1 μg/ml | 28527 | 28021 | 28035 | 28646 | 29613 | 34911 |
| 109 | 28368 | 30373 | 29858 | 29895 | 30941 | 29386 |

TABLE 11-continued

Relative Fluorescence of Transfection of Human Primary Fibroblast Cells

| Transfection Agent SEQ ID NO | Rf | | | | | |
|---|---|---|---|---|---|---|
| | 1 µl | 1.5 µl | 2 µl | 3 µl | 4 µl | 6 µl |
| 547 | 29141 | 33704 | 35175 | 35563 | 33951 | 30539 |
| 546 | 31980 | 39259 | 41747 | 35020 | 32220 | 29476 |
| Blank | 26822 | 26658 | 26624 | 25988 | 27112 | 26703 |

TABLE 12

Relative Fluorescence of Transfection of HuVEC Cells

| Transfection Agent SEQ ID NO | Rf | | | | | |
|---|---|---|---|---|---|---|
| | 1 µl | 1.5 µl | 2 µl | 3 µl | 4 µl | 6 µl |
| Blank | 23420 | 23592 | 23275 | 23437 | 23969 | 23973 |
| 543 | 26622 | 36742 | 42802 | 40584 | 32754 | 25492 |
| 545 | 26545 | 36649 | 46890 | 34047 | 30893 | 27133 |
| 544 | 25788 | 28622 | 31245 | 34718 | 31159 | 28639 |
| 540 | 24771 | 34062 | 44744 | 44087 | 45137 | 30023 |
| 541 | 27405 | 46446 | OVER | 40401 | 31568 | 28125 |
| 542 | 24827 | 33896 | 42546 | 43231 | 35294 | 29326 |
| DOTMA 1 µg/ml | 24590 | 24571 | 24811 | 24463 | 26972 | 29850 |
| 109 | 24603 | 25735 | 25421 | 26641 | 26529 | 25907 |
| 547 | 24554 | 26172 | 28255 | 32494 | 31180 | 26775 |
| 546 | 25990 | 32762 | 37899 | 35528 | 31614 | 27690 |
| Blank | 24151 | 23427 | 23055 | 23320 | 23689 | 24147 |

Example 3: Formulation 1

Formulation 1 comprised a combination of cationic lipids, neutral lipids, and peptides, as described above. Specifically, the cationic lipids used in Formulation 1 included DPePE-Sp-OMe and DPB-Arg. These cationic lipids are compounds of Formula 1, where:

DPePE-Sp-OMe=$R^1$=$R^2$=$C_{16}H_{31}$, X=O, $W^1$=H; $W^2$=$CH_2$—O—P(=O)(OMe)-O—$CH_2CH_2$—NH—C(=O)-spermine, y=0;

DPB-Arg=$W^1$=$W^2$=$CH_2$—N($R^3R^4$), $R^1$=$R^2$=$C_{16}H_{31}$, X=O; $R^3$=$CH_3$, $R^4$=C(=O)—C(NH$_2$)—$CH_2$—($CH_2$)n-C(=NH)—$NH_2$, n=0-6, y=0.

The neutral lipids included dioleoylphosphatidylethanolamine (DOPE), diphytanoylphosphatidylethanolamine (DPhPE), and 3-oleyloxy-2-hydroxy-1-acetamidopropane (HOAP).

The cationic lipid and the neutral lipid are combined in ethanol in the ratio of 1:8 (cationic lipid:neutral lipid). Formulation 1 was obtained by mixing the lipid with water and the peptide in the ratio of 0.2:1:1 (lipid mix:water:peptide mix). Specifically, the following peptides were used to prepare Formulation 1:

Peptide A: SEQ ID NO:507 covalently linked to SEQ ID NO:109 (4.1 mg/mL in HEPES);
Peptide B: SEQ ID NO:540 (4.1 mg/mL in HEPES);
Peptide C: SEQ ID NO:350 covalently linked to SEQ ID NO:109 (4.1 mg/mL in HEPES);
Peptide D: SEQ ID NO:47 (1 mg/mL in TRIS).

For Formulation 1, the lipid component comprised lipids in the molar ratio of 0.50:0.50:2.666:2.666:2.666 (DPePe-Sp-OMe:DPB-Arg:DOPE:DPhPE:HOAP). This translates to a cationic lipid:neutral lipid ratio of 1:8. The mixture of peptides in the formulation were present in the ratio of 1:2:2:0.5 by volume (Peptide A:Peptide B:Peptide C:Peptide D).

Example 4: Transfection

Human Adult Dermal Fibroblast was obtained from ScienCell Research Laboratories (Carlsbad, Calif.) and grown according to manufacturer's instructions. Human Adult Keratinocytes were obtained from ThermoFisher Scientific and grown according to manufactures instructions in Keratinocyte-SFM. Cells were plated to obtain approximately 70% confluency the day of transfection in 96-well tissue culture treated plates. Green Fluorescent Protein expression plasmid was used in these experiments. Transfection complexes for Lipofectamine 3000 were prepared according to manufacturer's instructions. All solutions used to form transfection complexes were at room temperature for transfection. Into each well of a non-tissue culture treated plate containing 0.05 mL of OptIMEM were aliquoted 1.0, 1.5, 2.0, 3.0, 4.0 and 6.0 µL of the Formulation 1 transfection reagent. A volume of 0.05 mL of a 20 µg/mL solution of DNA in OptiMEM was aliquoted into each well of a non-tissue culture treated plate that contained transfection reagent aliquots. The transfection reagent and DNA solution were mixed by pipetting up and down twice. Transfection complexes were formed for 10 minutes at room temperature. After 10 minutes, 0.01 mL of the transfection complex was added to cells. Cells were incubated for 42 hours at 37° C. at 5% $CO_2$. Plates were read on a fluorescent plate reader. The results are shown in Tables 13 and 14. Cells were also examined visually under a microscope to assess the extent of transfection (regarding the percent of cells transfected) with a fluorescent microscope. Other modes of analysis, for example, quantification with B-galactosidase or luciferase reports plasmids, can also be used.

TABLE 13

Relative Fluorescence of Transfection of Human Primary Adult Fibroblasts

| Volume of Transfection Reagent/well | Formulation 1 | Lipofectamine 3000 | Blank |
|---|---|---|---|
| 0.1 µL | 21851 | 9648 | 9373 |
| 0.15 µL | 21359 | 10041 | 9017 |
| 0.2 µL | 26793 | 12509 | 9135 |
| 0.3 µL | 35137 | 15193 | 9088 |
| 0.4 µL | 42224 | 16971 | 9200 |
| 0.6 µL | 42154 | 18095 | 9345 |

TABLE 14

Relative Fluorescence of Transfection of Human Primary Adult Keratinocytes

| Volume of Transfection Reagent/well | Formulation 1 | Lipofectamine 3000 | Blank |
|---|---|---|---|
| 0.1 µL | 41003 | 15028 | 13843 |
| 0.15 µL | 36375 | 15981 | 13820 |
| 0.2 µL | 33300 | 15538 | 13674 |
| 0.3 µL | 23132 | 14780 | 13412 |
| 0.4 µL | 19578 | 15176 | 13987 |
| 0.6 µL | 17126 | 14934 | 13704 |

What is claimed is:

1. A transfection complex comprising a combination of a cationic lipid, a neutral lipid, and a peptide, wherein:

the cationic lipid is a compound of Formula 1,

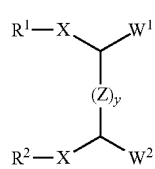

(I)

wherein:

$Z=(CH_2)_q$, $(CH_2)_q-N(R^3)-(CH_2)_q$, $(CH_2)_q-S-S-(CH_2)_q$, or $(CH_2)_q-O-(CH_2)_q$, wherein q=1-3 and $R^3=CH_3$; and i) $R^1=R^2=C_{16}H_{31}$, X=O, $W^1$=H; $W^2=CH_2-O-P(=O)(OMe)-O-CH_2CH_2-NH-C(=O)$-spermine, y=0 (DPePE-Sp-OMe); or ii) $W^1=W^2=CH_2-N(R^3R^4)$, $R^1=R^2=C_{16}H_{31}$, X=O; $R^3=CH_3$, $R^4=-C(=O)-C(NH_2)-CH_2-(CH_2)_n-C(=NH)-NH_2$, n=0-6, y=0 (DPB-Arg); and the neutral lipid is selected from dioleoylphosphatidylethanolamine (DOPE), diphytanoylphosphatidylethanolamine (DPhPE), and 3-oleyloxy-2-hydroxy-1-acetamidopropane (HOAP); and the peptide is selected from:

a) SEQ ID NO:507 covalently linked to SEQ ID NO:109 (Peptide A);

b) SEQ ID NO:540 (Peptide B); and c) SEQ ID NO:350 covalently linked to SEQ ID NO:109 (Peptide C).

2. The transfection complex of claim 1, wherein the cationic lipid and the neutral lipid are combined in ethanol such that the ration of cationic lipid:neutral lipid is between 0.1%-100% and 100%-0.1%.

3. The transfection complex of claim 1, wherein the cationic lipid and the neutral lipid are combined in ethanol in the ratio of 1:8 (cationic lipid:neutral lipid).

4. The transfection complex of claim 1, wherein the lipid component comprises lipids in the molar ratio of 0.50:0.50:2.666:2.666:2.666 (DPePe-Sp-OMe:DPB-Arg: DOPE:DPh-PE:HOAP).

5. The transfection complex of claim 1, wherein the complex comprises a mixture of Peptide A, Peptide B and Peptide C and further comprises the peptide of SEQ ID NO:47 (Peptide D) and wherein the mixture of peptides in the formulation is present in the ratio of 1:2:2:0.5 by volume (Peptide A:Peptide B:Peptide C:Peptide D).

* * * * *